US009186343B2

(12) United States Patent
Barker

(10) Patent No.: US 9,186,343 B2
(45) Date of Patent: Nov. 17, 2015

(54) NANOVESO™: TREATMENT, BIOMARKERS AND DIAGNOSTIC TESTS FOR LIVER DISEASES AND COMORBID DISEASES

(75) Inventor: David K. Barker, Black Mountain, NC (US)

(73) Assignee: Nanoveson, LLC, Black Mountain, NC (US)

(*) Notice: Subject to any disclaimer, the term of this patent is extended or adjusted under 35 U.S.C. 154(b) by 1158 days.

(21) Appl. No.: 12/317,627

(22) Filed: Dec. 24, 2008

(65) Prior Publication Data

US 2009/0181109 A1 Jul. 16, 2009

Related U.S. Application Data

(60) Provisional application No. 61/009,092, filed on Dec. 26, 2007, provisional application No. 61/124,940, filed on Apr. 21, 2008, provisional application No. 61/192,331, filed on Sep. 17, 2008.

(51) Int. Cl.
| | |
|---|---|
| *A61K 9/127* | (2006.01) |
| *A61K 31/201* | (2006.01) |
| *A61K 31/20* | (2006.01) |
| *A61K 31/202* | (2006.01) |
| *A61K 31/23* | (2006.01) |
| *A61K 33/12* | (2006.01) |
| *A61K 45/06* | (2006.01) |

(52) U.S. Cl.
CPC .............. *A61K 31/201* (2013.01); *A61K 31/20* (2013.01); *A61K 31/202* (2013.01); *A61K 31/23* (2013.01); *A61K 33/12* (2013.01); *A61K 45/06* (2013.01)

(58) Field of Classification Search
None
See application file for complete search history.

(56) References Cited

U.S. PATENT DOCUMENTS

| 2004/0171582 | A1* | 9/2004 | Nakade et al. ............ 514/54 |
| 2006/0211762 | A1* | 9/2006 | Rongen et al. ............ 514/423 |
| 2007/0004670 | A1* | 1/2007 | Wurtman et al. ............ 514/49 |
| 2009/0281039 | A1* | 11/2009 | Malkki ............ 514/12 |

OTHER PUBLICATIONS

Shao-Ji Yang, Hepatobiliary Pancreat. Dis Int, vol. 3, No. 1, Feb. 15, 2004, pp. 10-11.*
Mutation research—(480-481 (2001) 219-229.*
Browning, Jeffrey D. et al., "Prevalence of Hepatic Steatosis in an Urban Population in the United States: Impact of Ethnicity", *Hepatology*, vol. 40, No. 6, (2004) p. 1387-1395.
Adams, L.A. and Angulot P., "Recent concept in non-alcoholic fatty liver disease", Diabetes Uk, *Diabetic Medicine*, vol. 22, (2005) p. 1129-1133.
New Technologies for Liver Disease STTR (R41/R42) http://grants.nih.gov/grants/guide/pa-files/PA-06-396.html.
Patton, George M. et al. "Evidence that hepatic triglyceride provide acylglycerides for synthesis of bile phosphatidylcholines" *Am. J. Physiol.* 267 (*Gastrointest. Liver Physiol.*30): (1994) p. 1028-1034.
Boucrot, Philippe "Is There an Entero-Hepatic Circulation of the Bile Phospholipids?" *Lipids*, vol. 7, No. 5, ( 1972), p. 285-288.
Bellentani, Stefano et al., "Prevalence of and Risk Factors for Hepatic Steatosis in Northern Italy", *Ann Intern Med.* 2000; 132: p. 112-117.
Samuel, Varman T., et al., "Mechanism of Hepatic Insulin Resistance in Non-alcoholic Fatty Liver Disease" *The Journal of Biological Chemistry*, vol. 279, No. 31, Issue of Jul. 30, 2004, p. 32345-32353.
Schattenberg, Jörn M., et al., "Hepatocyte CYP2E1 Overexpression and Steatohepatitis Lead to Impaired Hepatic Insulin Signaling" *The Journal of Biological Chemistry*, vol. 280, No. 11, Issue of Mar. 18, 2005, p. 9887-9894.
Malagelada, Juan-R, et al., "Pancreatic, Gallbladder, and Intestinal Response to Intraluminal Magnesium Salts in Man" *Digestive Diseases*, vol. 23, No. 6 (Jun. 1978), p. 481-485.
Elin, RJ., "Magnesium metabolism in health and disease" *Dis-Mon.* Apr. 1988; 34(4), p. 161-218 (Abstract).
Turecky L, et al., "Serum magnesium levels in patients with alcoholic and non-alcoholic fatty liver" *Bratisl Lek Listy* (2006); 107 (3), p. 58-61.
Nadler, JL., et al., "Magnesium deficiency produces insulin resistance and increased thromboxane synthesis" *Hypertension* (1993); 21; p. 1024-1029.
Braulin, William et al., "Bile acid binding to sevelamer HCI" *Kidney International*, vol. 62 (2002), p. 611-619.
Shamburek, Robert D. and Schwartz, Charles C., "Selective composition of biliary phosphatidylcholines is affected by secretion rate but not by bile acid hydrophobicity" *Journal of Lipid Research*, vol. 34 (1993), p. 1833-1842.
Westergaard, Henrik and Dietschy, John M., "The Mechanism Whereby Bile Acid Micelles Increase the Rate of Fatty Acid and Cholesterol Uptake into the Intestinal Mucosal Cell", *The Journal of Clinical Investigation*, vol. 58 (Jul. 1976), p. 97-108.
Chen, Alice and Innis, Sheila, "Assessment of Phospholipid Malabsorption by Quantification of Fecal Phospholipid" *Journal of Pediatric Gastroenterology and Nutrition*, vol. 39 (Jul. 2004), p. 85-91.
Hismiogullari, Adnan Adil, et al., "Biliary lipid secretion" *Turk J Gastroenterol* 2007, 18 (2), p. 65-70.
Chen, Alice et al., "Phosphatidylcholine and lysophosphatidylcholine excretion is increased in children with cystic fibrosis and is associated with plasma homocysteine, S-adenosylhomocysteine, and S-adenosylmethionine [1-3]" *Am J. Clin. Nutr.* 2005; 81, p. 686-91.
Zhou, Li and Nilsson, Ake "Sources of eicosanoid precursor fatty acid pools in tissues" *Journal of Lipid Research*, vol. 42 (2001), p. 1521-1542.
The Lancet vol. 365, No. 9468 Apr. 16, 2005.
Trauner, Michael, et al., "Molecular Pathogenesis of Cholestasis" *Mechanisms of Disease*, vol. 339, No. 17 (Oct. 22, 1998) p. 1217-1227.

(Continued)

*Primary Examiner* — Snigdha Maewall
(74) *Attorney, Agent, or Firm* — Olive Law Group PLLC; Nathan P. Letts

(57) ABSTRACT

A method of treatment of liver diseases and comorbid diseases is disclosed wherein an oral dose of lipids in an amount effective to trigger the release of cholecystokinin (CCK) into the duodenum to generate a major release of bile phospholipids from remodeled stores of triglycerides (TAG) in the liver, is administered to a patient in need thereof, thereby causing the formation of sequestered and aggregated mixed micelles and vesicles (SAMMVs) in the intestines of the patient which are then eliminated via the bowels of the patient.

19 Claims, 20 Drawing Sheets

(56) References Cited

OTHER PUBLICATIONS

Barton, P., et al., "Biliary Sludge After Liver Transplantation:2. Treatment with Interventional Techniques Versus Surgery and/or Oral Chemolysis" *AJR* (1995); 164, p. 865-869.

Ko, Cynthia W., et al., "Bilary Sludge" *Annals of Internal Medicine*, vol. 130, No. 4 (Part 1), (Feb. 16, 1999), p. 301-311.

Hofmann, Alan F. and Mysels, Karol J. "Bile acid solubility and precipitation in vitro and in vivo: the role of conjugation, pH, and Ca2+ ions" *Journal of Lipid Research* vol. 33 (1992), p. 617-626.

Kim, W. Ray, et al., "Adaptation of the Mayo Primary Biliary Cirrhosis Natural History of Model for Application in Liver Transplant Candidates" *Liver Transplantation*, vol. 6, No. 4 (Jul. 2000), p. 489-494.

Ricci, Paola, et al., "A Prognostic Model for the Outcome of Liver Transplantation in Patient With Cholestatic Liver Disease" *Hepatology* vol. 25, No. 3, (1997), p. 672-677.

Bambha, Kiran et al., "Incidence, Clinical Spectrum, and Outcomes of Primary Sclerosing Cholangitis in a United States Community" *Gastroenterology* (2003), 125, p. 1364-1369.

Gross, Cynthia R., et al., "Quality of Life Before and After Liver Transplantation for Cholestatic Liver Disease" *Hepatology*, vol. 29, No. 2, (1999), p. 356-364.

Kim, W. Ray, et al., "A Revised Natural History Model for Primary Sclerosing Cholangitis" *Mayo Clin Proc.* (2000); 75, p. 688-694.

Textor, Stephen C., et al., "Urinary endothelin and renal vascoconstriction with cyclosporine or FK506 after liver transplantation" *Kidney International*, vol. 47 (1995), p. 1426-1433.

Schurtenberger, Peter, et al., "Dynamic Laser Light Scattering Studies of the Micelle to Vesicle Transition in Model and Native Bile" *Hepatology*, vol. 4, No. 5 (1984), p. 143S-147S.

Carey, Martin C. "Bile Acids and Bile Salts: Ionization and Solubility Properties" *Hepatology*, vol. 4, No. 5 (1984), p. 66S-71S.

Carey, Martin C. "Lipid Digestion and Absorption", *Ann. Rev. Physiol.* (1983); 45, p. 651-77.

Crawford, Aleta R., et al., "Hepatic Secretion of Phospholipid Vesicles in the Mouse Critically Depends on mdr2 or MDR3 P-Glycoprotein Expression", *J. Clin. Invest.*, vol. 100, No. 10, (Nov. 1997), p. 2562-2567.

Hofmann, Alan F. "The Continuing Importance of Bile Acids in Liver and Intestinal Disease" *Arch Intern Med.* (1999), vol. 159, p. 2647-2658.

Hofmann, Alan F. "Bile Acids: The Good, the Bad, and the Ugly", *New Physiol. Sci.*, vol. 14, (1999), p. 24-29.

Quist, RG, et al., "Activation of mast cells by bile acids", *Gastroenterology*, vol. 101, Issue 2 (Aug. 1991), p. 446-456 (Abstract).

Malagelada, Juan-R, et al., "Regulation of Pancreatic and Gallbladder Functions by Intraluminal Fatty Acids and Bile Acids in Man", *The Journal of Clinical Investigations*, vol. 58 (Aug. 1976), p. 493-499.

Bennett, Susanne "Intestinal Absorptive Capacity and Site of Absorption of Fat Under Steady State Conditions in the Unanesthetized Rat" *Journal of Lipid Research*, vol. 12 (1971), p. 210-218.

Crawford, James M., M.D., Ph.D., and Li, Melissa K., M.D., "The Pathology of Cholestasis" *Seminars in Liver Disease*, vol. 24, No. 1, (2004) p. 21-42.

Hoekstra, Menno, et al., "Microarray analysis indicates an important role for FABP5 and putative novel fatty acid binding proteins in the primary response of liver parenchymal cells from LDL receptor deficient mice to a Western-type diet", *Journal of Lipid Research* (2006), p. 1-40.

Shimano, Hitoshi, et al., "Sterol Regulatory Element-binding Protein-1 as a Key Transcription Factor for Nutritional Induction of Lipogenic Enzyme Genes", *The Journal of Biological Chemistry*, vol. 274, No. 50, Issue of Dec. 10, 1999, pp. 35832-35839.

Mizuarai, Shinji, et al, "Identification of Dicarboxylate Carrier Slc25a10 as Malate Transporter in de Novo Fatty Acid Synthesis" *Journal of Biological Chemistry*, vol. 280, No. 37 (Sep. 16, 2005), p. 32434-32441.

Werner, Anniek et al, "Treatment of EFA deficiency with dietary triglycerides or phospholipids in a murine model of extrahepatic cholestasis" *Am J. Physiol Gastrointest Liver Physiol* 286 (2004), p. G822-G832.

Phan, Cam T., and Tso, Patrick "Intestinal Lipid Absorption and Transport" *Frontiers in Bioscience*, vol. 6 (Mar. 1, 2001), p. 299-319.

Graham, Annette et al., "Factors regulating the secretion of lysophosphatidylcholine by rat hepatocytes compared with the synthesis and secretion of phosphatidylcholine and triacylglycerol" *Biochem J.* (1988) vol. 253, p. 687-692.

Chen, Xiaoxin et al. "Aberrant arachidonic acid metabolism in esophageal adenocarcinogenesis, and the effects of sulindac, nordihydroguaiaretic acid, and α-difluoromethylomithine on tumorigenesis in a rat surgical model" *Carcinogenesis* vol. 23, No. 12, pp. 2095-2102, 2002.

Connolly, JM and Rose, DP "Regulation of tumor angiogenesis by dietary fatty acids and eicosanoids" *Nutr Cancer* (2000); 37(2), p. 119-127 (Abstract).

Marks F. et al., "A causal relationship between unscheduled eicosanoid signaling and tumor development cancer chemoprevention by inhibitors of arachidonic acid metabolism" *Toxicology*, (Nov. 16, 2000); vol. 153(1-3), p. 11-26 (Abstract).

Butcher, Russell D., et al., "Arachidonic Acid, a Growth Signal in Murine P815 Mastocytoma Cells" *Cancer Research* vol. 53 (Jul. 15, 1993), p. 3405-3410.

Ballatori, Nazzareno and Wang, Wei, "Endogenous Glutathione Conjugates: Occurrence and Biological Functions" *Pharmacological Reviews*, vol. 50, No. 3 (1998 ), p. 335-355.

Zeldin, Darryl C. "Epoxygenase Pathways of Arachidonic Acid Metabolism", *The Journal of Biological Chemistry*, vol. 276, No. 39, Issue of Sep. 28, 2001, p. 36059-36062.

Park, Sonhee C., et al., "Effect of Male Sex and Obesity on Platelet Arachidonic Acid in Spontaneous Hypertensive Heart Failure Rats", *Experimental Biology and Medicine* 229 (2004), p. 657-664.

Roman, Richard J., "P-450 Metabolites of Arachidonic Acid in the Control of Cardiovascular Function", Physiological Review vol. 82 (2002), p. 131-185.

Takase, Bonpei, et al., "Arachidonic Acid Metabolites in Acute Myocardial Infarction", The Journal of Vascular Diseases, vol. 47, No. 7, (Jul. 1996), p. 649-661.

Bogatcheva, Natalia V., et al., "Arachidonic acid cascade in endothelial pathiobiology", Microvascular Research 69 (2005); p. 107-127.

Sheng, Rubin, MD., et al., "Biliary Stones and Sludge in Liver Transplant Patients: A 13-year Experience", Radiology vol. 198 (1996), p. 243-247.

Campbell, William L., MD, et al., "Intrahepatic Biliary Strictures after Liver Transplantation", Abdominal and Gastrointestinal Radiology, vol. 191 (1994), p. 735-740.

Boyle-Roden, Elizabeth and Walzem, Rosemary L. "Integral apolipoproteins increase surface-located triacylglycerol in intact native apoB-100-containing lipoproteins", Journal of Lipid Research, vol. 46 (2005), pp. 1624-1632.

Heerklotz, H. and Seelig, J. "Correlation of Membrane/Water Partition of Coefficients of Detergents with the Critical Micelle Concentration", Biophysical Journal, vol. (May 2000), p. 2435-2440.

Motomura, K., et al., "Thermaodynamic consideration of the mixed micelle of surfactants" Colloid & Polymer Science vol. 262, (1984), p. 948-955.

Heerklotz, Heiko, et al., "The Enthalpy of Acy Chain Packing and the Apparent Water-Accessible Apolar Surface Area of Phospholipids", Biophysical Journal, vol. 80, (Jan. 2001), p. 271-279.

Spink, Charles H., et al., "Micelle-Vesicle Transition in Phospholipid-Bile Salt Mixtures. A Study by Precision Scanning Calorimetry", Biochemistry, vol. 30, (1991), p. 5104-5112.

Wickham, Martin, et al., "Modification of a phospholipids stabilized emulsion interface by bile salt: effect on pancreatic lipase activity", Journal of Lipid Research, vol. 39, (1998), p. 623-632.

Huber, Michael, et al., "Metabolism of cysteinyl leukotrienes in monkey and man", Eur. J. Biochem, vol. 194 (1990), p. 309-315.

(56) References Cited

OTHER PUBLICATIONS

Hughes-Fulford, Millie, et al., "Arachidonic Acid Activates Phosphatidylinositol 3-Kinase Signaling and Induces Gene Expression in Prostate Cancer", Cancer Research, vol. 66 (3) (2006), p. 1427-1433.

Ghosh, Jagadananda and Myers, Charles E. "Inhibition of arachidonate 5-lipoxygenase triggers massive apoptosis in human prostate cancer cells", Proc. Natl. Acad. Sci. USA, vol. 95, (Oct. 1998), p. 13182-13187.

Simopoulos, Artemis P., et al., "Essential fatty acids in health and chronic disease", Am J Clin Nutr, vol. 70 (suppl), (1999), p. 560S-9S.

Waddington, E., et al., "Identification and Quantitation of Unique Fatty Acid Oxidation Products in Human Atherosclerotic Plaque Using High-Performance Liquid Chromatography", Analytical Biochemical, vol. 292, No. 2, (May 2001), p. 234-244(11).

Cai, Hua and Harrison, David G., "Endothelial Dysfunction in Cardiovascular Diseases: The Role of Oxidant Stress", Circulation Research, vol. 87, (2000), p. 840-844.

Elinder, Liselotte Schafer, "Expression of Phospholipase $A_2$ Isoforms in Human Normal and Atherosclerotic Arterial Wall", Arteriosclerosis, Thrombosis, and Vascular Biology, vol. 17 (1997), p. 2257-2263.

Booker, Michael L., et al., "Distribution of phosphatidylcholine molecular species between mixed micelles and phospholipids cholesterol vesicles in human gallbladder bile: dependence on acyl chain length and unsaturation", Journal of Lipid Research, vol. 33 (1992), p. 1485-1492.

Olmsted, C.A., "Studies on the Role of Phospholipids in the Triglyceride Cycle: III. Liver and Plasma Phospholipid Exchange in Depancreatized Dogs", Lipids, vol. 6, No. 6 (Jun. 1971 ), p. 394-400.

Eberhart, Charles E. and Raymond Dubois N., "Eicosanoids and the Gastrointestinal Tract", Gastroenterology, vol. 109 (1995), p. 285-301.

O'Byrne, Paul M., "Leukotrienes in the pathogenesis of asthma", Chest, vol. 111 (1997), p. 27-34.

Grossman, Jay, MD, FCCP, "One Airway, One Disease", Chest, vol. 111 (1997), p. 11-16.

Calabrese, C., et al., "Arachidonic acid metabolism in inflammatory cells of patients with bronchial asthma", Allergy, Suppl. 61 (2000), p. 27-30.

Black, P.N. and Sharpe, S., "Dietary fat and asthma: is there a connection?", Eur. Respir J., vol. 10 (1997), p. 6-12.

Halpern, Z., et al., "Effect of phospholipids and their molecular species on cholesterol solubility and nucleation in human and model biles", Gut, vol. 34 (1993), p. 110-115.

Lewis, Myra J., et al., "Cystic Fibrosis", Am J Clin Pathol vol. 120 (Suppl. 1) (2003), p. S3-S13.

Coleman, Roger. "Biochemistry of bile secretion" Biochem. J. (1987) 244, 249-261.

Rigler, M.W., et al., "Visualization by freeze fracture, in vitro and in vivo, of the products of fat digestion", Journal of Lipid Research, vol. 27 (1986), p. 836-857.

Korgel, Brian A., et al., "Vesicle Size Distributions Measured by Flow Field-Flow Fractionation Coupled with Multiangle Light Scattering", Biophysical Journal, vol. 74 (Jun. 1998), p. 3264-3272).

European Commission, Health & Consumer Protection Directorate General, "Opinion of the Scientific Committee on Food on the Tolerable Upper Intake Level of Magnesium", (Oct. 11, 2001), p. 1-16.

Beare-Rogers, J. et al. "Lexicon of Lipid Nutrition" Pure Appl. Chem. vol. 73, No. 4, (2001) pp. 685-744.

Halpern, Zamir, et al., "Vesicle aggregation in model systems of supersaturated bile: relation to crystal nucleation and lipid composition of the vesicular phase", Journal of Lipid Research, vol. 27 (1986), p. 295-306.

Gantz, Donald L., et al., "Cryoelectron Microscopy of a Nucleating Model Bile in Vitreous Ice: Formation of Primordial Vesicles", Biophysical Journal, vol. 76 (Mar. 1999), p. 1436-1451.

Chen, Irene A. and Szostak, Jack W. "A Kinetic Study of Growth of Fatty Acid Vesicles", Biophysical Journal, vol. 87 (Aug. 2004), p. 988-998.

Wilschut, Jan, et al., "Calcium/Magnesium Specificity in Membrane Fusion: Kinetics of Aggregation and Fusion of Phosphatidylserine Vesicles and the Role of Bilayer Curvature", Biochemistry, vol. 20, No. 11 (1981), p. 3126-3133.

Leventis, Rania, et al., "Divalent Cation Induced Fusion and Lipid Lateral Segregation in Phosphatidylcholine-Phosphatidic Acid Vesicles", Biochemistry, vol. 25 (1986) p. 6978-6987.

Creutz, Carl E. "cis-Unsaturated Fatty Acids Induce the Fusion of Chromaffin Granules Aggregated by Synexin", The Journal of Cell Biology, vol. 91 (Oct. 1981), p. 247-256.

Bloch-Shilderman, Eugenia, et al., "Pardaxin Stimulation of Phospholipases $A_2$ and Their Involvement in Exocytosis PC-12 Cells", The Journal of Pharmacology and Experimental Therapeutics, vol. 301, No. 3, (2002) p. 953-962.

Abu-Raya, Saleh, et al., "Characterization of Pardaxin-Induced Dopamine Release from Pheochromocytoma Cells: Role of Calcium and Eicosanoids", The Journal of Pharmacology and Experimental Therapeutics, vol. 288, No. 2 (1999), p. 399-406.

Mayorga, Luis S., et al., "Inhibition of endosome fusion by phospholipase A2 (PLA2) inhibitors points to a role for PLA2 in endocytosis", Proc. Natl. Acad. Sci. USA, vol. 90 (Nov. 1993), p. 10255-10259.

McIntosh, Thomas J., et al., "Membrane Fusion Promoters and Inhibitors Have Contrasting Effects on Lipid Bilayer Structure and Undulations", Biophysical Journal, vol. 76 (Apr. 1999) p. 2090-2098.

Creutz, Carl E., et al., "Identification and Purification of an Adrenal Medullary Protein (Synexin) That Causes Calcium-dependent Aggregation of Isolated Chromaffin Granules", The Journal of Biological Chemistry, vol. 253, No. 8, Issue of Apr. 25, 1978, p. 2858-2866.

Creutz, Carl E. et al., "Self-association of Synexin in the Presence of Calcium", The Journal of Biological Chemistry, vol. 254, No. 2, Issue of Jan. 25, 1979, p. 553-558.

Pol, Albert, et al., "Identification of cytoskeleton-associated proteins in isolated rat liver endosomes", Biochem J. (1997) vol. 327, p. 741-746.

Meers, Paul, et al, "Synexin Enhances the Aggregation Rate but Not the Fusion Rate of Liposomes", Biochemistry, vol. 27, p. 4430-4439.

Katayanagi, Kazuyoshi, et al., "Generation of Monoclonal Antibodies to Murine Bile Duct Epithelial Cells: Identification of Annexin V as a New Marker of Small Intrahepatic Bile Ducts", Hepatology, vol. 29, No. 4 (1999), p. 1019-1025.

Renaud, Guy, et al., "Hepatic metabolism of colloidal gold-low-density lipoprotein complexes in the rat: Evidence for bulk excretion of lysosomal contents into bile" Hepatology, vol. 9, Issue 3 (Dec. 2005), p. 380-392. Abstract.

Sancho-Bru, Pau, et al., "Norepinephrine induces calcium spikes and proinflammatory actions in human hepatic stellate cells", Am J Physiol Gastrointest Liver Physiol, vol. 291 (2006), p. G877-G884.

Shibata, O., et al., "Free and conjugated catecholamines in gastric and bile juice during surgical operations", Masui, vol. 39 (8) (Aug. 1990), p. 978-983.

Calvo, Maria, et al., "Cellubrevin Is Present in the Basolateral Endocytic Compartment of Hepatocytes and Follows the Transcytotic after IgA Internalization", The Journal of Biological Chemistry, vol. 275, No. 11, Issue of Mar. 17, 2000, p. 7910-7917.

Clapham, David E. and Kim, Donghee, "Potassium Channels in Cardiac Cells Activated by Arachidonic Acid and Phospholipids", Science, vol. 244, (Jun. 9, 1989), p. 1174-1176.

Capdevila, Jorge H., et al., "Cytochrome P450 and arachidonic acid bioactivation: molecular and functional properties of the arachidonate monooxygenase", Journal of Lipid Research, vol. 41 (2000), p. 163-181.

Baraona, Enrique and Lieber, Charles S., "Effects of ethanol on lipid metabolism", Journal of Lipid Research, vol. 20 (1979), p. 289-315.

Feigelson, Eugene B., et al., "The Role of Plasma Free Fatty Acids in Development of Fatty Liver", J Clin Invest. Dec. 1961; 40(12): 2171-2179.

Kelavkar, Uddhav P., et al., "Concordant Induction of 15-lipoxygenase-1 and mutant p53 expression in human prostate adenocarcinoma: correlation with Gleason staging", Carcinogenesis, vol. 21, No. 10 (2000), p. 1777-1787.

(56) References Cited

OTHER PUBLICATIONS

Larsson, Susanna C. et al., "Dietary long-chain n-3 fatty acids for the prevention of cancer: a review of potential mechanisms[1-3]", *Am J Clin Nutr* (2004), vol. 79, p. 935-945.

Kobayashi, Naoko, et al., "Effect of Altering Dietary ω-6/ω-3 Fatty Acid Ratios on Prostate Cancer Membrane Composition, Cycloxygenase-2, and Prostaglandin E2", *Clin Cancer Res* (Aug. 1, 2006) vol. 12(15), p. 4662-4670.

Hardman, Elaine W "(n-3) Fatty Acids and Caner Therapy", *Journal of Nutrition* vol. 134 (2004), p. 3427S-3430S.

Baracos, Vickie E., et al., "n-3 Polyunsaturated fatty acids throughout the cancer trajectory: influence on disease incidence, progression, response to therapy and cancer-associated cachexia", *Nutrition Research Reviews*, vol. 17, (2004), 177-192.

Roco, Mihail C. "Nanotechnology: convergence with modern biology and medicine", *Current Opinion in Biotechnology*, vol. 14 (2003), p. 337-346.

Cullis, P.R. and De Kruijff, B. "Lipid Polymorphism and the Functional Roles of Lipids in Biological Membranes", *Biochimica et Biophysica Acta*, vol. 559 (1979), p. 399-420.

Eckhardt, Erik R.M., et al., "Asymmetric distribution of phosphatidylcholine and sphingomyelin between micellar and vesicular phases: potential implications for canalicular bile formation" *Journal of Lipid Research*, vol. 40 (1999), p. 2022-2033.

Roberst, Michael S., et al., "Enterohepatic Circulation", *Clin. Pharmacokinet*, vol. 41(10), (2002), p. 752-790.

Younossi, Z.M., "Review article: current management of non-alcoholic fatty liver disease and non-alcoholic steatohepatitis", *Aliment Pharmacol Ther*, vol. 28 (2008), p. 2-12.

Green, Richard M., M.D., "NASH—Hepatic Metabolism and Not Simply the Metabolic Syndrome", *Hepatology*, vol. 38, No. 1 (2003), p. 14-17.

Kantartzis, Konstantinos, et al., "Causes and Metabolic Consequences of Fatty Liver", *Endocrine Reviews* (2008), Abstract.

Ahmed, Aijaz, M.D., et al., "Management of Gallstones and Their Complications", *American Family Physician* (Mar. 15, 2000), p. 1-11.

Sundaram, Shikha S., et al., "Steatohepatitis develops rapidly in transgenic mice overexpressing *Abcb11* and fed a methionine-choline-deficient diet", *Am J. Physiol Gastrointest Liver Physiol*, vol. 288 (2005), p. G1321-1327.

Lombardi, B., et al., "Choline-deficiency fatty liver: impaired release of hepatic triglycerides", *Journal of Lipid Research*, vol. 9 (1968), p. 437-446.

Borensztajn, Jayme, et al., "Mechanisms of steatosis in mice fed a lipogenic methionine choline deficient (MCD) diet", *Journal of Lipid Research*, vol. 49, 1068-1076, May 2008.

Burke, John E. and Dennis, Edward A., "Phospholipase $A_2$ Structure/Function, Mechanism and Signaling", *Journal of Lipid Research* (2008), p. 1-8.

Fitzpatrick, F.A. and Soberman, Roy, "Regulated formation of eicosanoids", *The Journal of Clinical Investigation*, vol. 107, No. 11 (2001), p. 1347-1351.

Dreamer, D., et al., "Prebiotic Molecular Selection and Organization", Carnegie Institute of Washington. Reporting Period: 2006 (Jul. 2005-Jun. 2006). http://nai.nasa.gov/team/index.cfm?page=proiect reports&year=8&teamID=14&proiected=1829.

Moritz, Andreas "The Amazing Liver & Gallbladder Flush," Ener-Chi Wellness Press, U.S.A., pp. v-xv, 106-122, 154-156, and 164-192 (2005).

Halpern, Z., et al., "Effect of Phospholipids and Their Molecular Species on Cholesterol Solubility and Nucleation in Human and Model Biles", Gut.,1993; vol. 34, pp. 110-115.

Rahman, K., et al., "Biliary Lipid Secretion", Turk. J. Gastroenterol., 2007; vol. 18, Issue 2, pp. 65-70.

Patton, G. M., et al., "Evidence that Hepatic Triglycerides Provide Acylglycerides for Synthesis of Bile Phosphatidylcholines", Am. J. Physiol., 1994, 267(6 Pt 1): G1028-34.

\* cited by examiner

TABLE I
Compounds Tested for Fusogenic Activity *

| Compound | Concentration (μg/ml) | ΔTurbidity‡ in 5 min (%) | Vesicle formation§ |
|---|---|---|---|
| 1. Arachidonic acid | 1 | 22 | 0 |
| [all cis 5,8,11,14 eicosatetraenoic acid (20:4)] | 2 | 31 | + |
|  | 4 | 81 | ++++ |
| 2. Linolenic acid | 4 | 49 | ++ |
| [all cis 9,12,15 octadecatrienoic acid (18:3)] |  |  |  |
| 3. Linoleic acid | 4 | 47 | ++ |
| [all cis 9,12 octadecadienoic acid (18:2)] |  |  |  |
| 4. Oleic acid | 4 | 44 | ++ |
| [cis 9 octadecenoic acid (18:1)] | 10 | 78 | ++++ |
| 5. Palmitoleic acid | 4 | 41.3 | ++ |
| [cis 9 hexadecenoic acid (16:1)] |  |  |  |
| 6. cis-Vaccenic acid | 4 | 34 | + |
| [cis 11 octadecenoic acid (18:1)] |  |  |  |
| 7. Erucic acid | 4 | 25.5 | + |
| [cis 13 docosenoic acid (22:1)] |  |  |  |
| 8. Petroselenic Acid | 4 | 0 | 0 |
| [cis 6 octadecenoic acid (18:1)] | 10 | 4 | 0 |
| 9. Elaidic Acid | 4 | 0 | 0 |
| [trans 9 octadecenoic acid (18:1)] | 10 | 0 | 0 |
| 10. Methyl arachidonate | 4 | 0 | 0 |
| 11. Methyl oleate | 4 | 0 | 0 |
| 12. Glycerol mono-oleate | 4 | 0 | 0 |
| 13. Lauric acid | 4 | 0 | 0 |
| 14. Myristic acid | 5 | 0 | 0 |
| 15. Palmitic acid | 4 | 0 | 0 |
| [hexadecanoic acid (16:0)] |  |  |  |
| 16. Stearic acid | 5 | 0 | 0 |
| [octadecanoic acid (18:0)] |  |  |  |
| 17. Stearyl amine | 4 | 0 | 0 |
| 18. Retinol | 4 | 0 | 0 |
| 19. α-Tocopherol | 4 | 0 | 0 |
| 20. Prostaglandin $E_2$ | 4 | 0 | 0 |
| 21. Lysolecithin | 4 | 0 | 0 |
| (from egg yolk) | 10 | 51 | 0 |
| 22. SDS | 4 | 12 | 0 |
| 23. Benzalkonium chloride | 4 | 0 | 0 |
|  | 8 | 0 | 0 |

\* Compounds were added to ~80 μg/ml of granule protein after aggregation by synexin for 15 min.
‡ Change in turbidity of the granule suspension induced by the compound after 5 min. Similar to the analysis in Fig. 2, the change is given as a percentage of the $A_{540}$ of the suspension before aggregation. The values given were reproducible to within five percentage units for a single preparation of granules or synexin. The relative order of effectiveness for different compounds was the same for all preparations of granules and synexin.
§ Degree of vesicle formation seen in the phase microscope: ++++, extensive fusion, one or more large vesicles have developed from every clump; ++, moderate fusion, most clumps have developed vesicles but these are smaller, leaving a large part of the clump unfused; +, limited fusion, vesicles are difficult to find, occurring in <5% of the clumps; 0, no fusion, not a single vesicle can be seen.

Fig. 10

Nanoveson Therapy - Potential Phospholipid "Remodeled TAG" Removal
Treating Fatty Liver

|  | Sample #1 | Sample #2 |
|---|---|---|
| SAMMV Sample Analysis | | |
| Total Phospholipid (PL) | | |
| mg of PL in 1 gram SAMMV | 8 | 19 |
| percent of PL to total SAMMV | 0.80% | 1.90% |
| grams of actual SAMMV sample sent to lab | 6.78 | 2.60 |
| total grams of SAMMVs from the Nanoveson Therapy treatment | 50 | 5 |

Potential PL Removal by Nanoveson Therapy
(Total PL release by SAMMV output using actual Sample #1 and #2 ratios)

| Range of Grams of SAMMVs by single therapy treatment | 1 | 10 | 25 | 50 | 75 | 100 | 200 |
|---|---|---|---|---|---|---|---|
| Sample #1 | | | | | | | |
| mg of PL in SAMMVs released per therapy | 8 | 80 | 200 | 400 | 600 | 800 | 1600 |
| 12.8 multiple of PL in AQ to PL in SAMMVs per therapy | 102 | 1024 | 2560 | 5120 | 7680 | 10240 | 20480 |
| total mg of PL in SAMMVs + AQ released per therapy | 110 | 1104 | 2760 | 5520 | 8280 | 11040 | 22080 |
| Sample #2 | | | | | | | |
| mg of PL in SAMMVs released per therapy | 19 | 190 | 475 | 950 | 1425 | 1900 | 3800 |
| 12.8 multiple of PL in AQ to PL in SAMMVs per therapy | 243 | 2432 | 6080 | 12160 | 18240 | 24320 | 48640 |
| total mg PL in SAMMVs + AQ released per therapy | 262 | 2622 | 6555 | 13110 | 19665 | 26220 | 52440 |

NANOVESO™: TREATMENT, BIOMARKERS AND DIAGNOSTIC TESTS FOR LIVER DISEASES AND COMORBID DISEASES

FIELD OF THE INVENTION

Lipid polymorphism represents an important area of current academic and life sciences research in the fields of biophysics, biochemistry and organic chemistry, exploring the remodeling of one form of lipid into another, e.g. triglycerides remodeled into phospholipids, and subsequent lipid fusion and aggregation into functional lipid structures such as micelles and vesicles based on lipid concentrations, temperature and pH (163,164), for critical roles in biological system. Nanotechnology is converging with modern biology and medicine and has been classified into two categories: 'wet' nanotechnology (inducing living biosystems) and 'dry' nanotechnology (162). Those skilled in the art will recognize that the invention is applicable to the nanotechnology category of 'wet' living biosystems in the area of membrane lipids. Nanobiotechnology is defined as a field that applies the nanoscale principles and techniques to understand and transform biosystems (162). Together, lipid polymorphism and membrane lipid nanobiotechnology offer the promise of a new approach to the diagnosis, treatment and prevention of liver disease, and major comorbid diseases. The triggering of lipid remodeling "polymorphism" and therapeutically manipulating the self-organizing properties of lipid membrane fusion and aggregation in a biosystem "nanobiotechnology" are fundamental to the novel and attractive mechanism of action of the invention. The majority of lipid metabolism occurs in the liver. The entire gastrointestinal tract and the liver, biliary system, gallbladder and pancreas are all involved in lipid digestion, uptake, synthesis and excretion and enterohepatic circulation (165), and therefore play a role in the novel utility of the invention. Liver disease is a contraindication for many blockbuster pharmaceutical products. The proposed method of treatment holds promise as a treatment option for indicated conditions when "contraindication" due to liver disease prevents the use of established therapy. The invention also holds promise as primary and combination therapy for major disease indications. The self-organization and incorporation of biomarkers for utilization in diagnostic tests is an inherent and important aspect of the invention.

BACKGROUND OF THE INVENTION

It is estimated that as many as 60 million or ~33% of the U.S. adult population, and increasing, suffer from excessive liver deposits of triglyceride (TAG) producing non-alcoholic fatty liver disease (NAFLD) (1,2) and there is growing recognition of the comorbidity of NAFLD with other major chronic diseases (2). There is mounting research evidence uncovering the link between fatty liver, including NAFLD, and insulin resistance, heart disease and other metabolic diseases (2,166,167,168). The incidence of adolescent NAFLD is also significant and rising. There are currently no FDA approved treatment options for fatty liver. The leading contenders are, Metformin, contraindicated for liver disease, and Actos; both have FDA black box warning status. The National Institutes of Health (NIH) has announced grant request for proposals (RFPs) for development of technologies and products to treat liver disease, including NAFLD, and for development of biomarkers and diagnostic tools for liver disease (3). There is a rapidly growing recognition on the part of medical practitioners and life science researchers of the need for therapy options and biomarkers for fatty liver and related diseases (166). Pursuit of FDA approvals and commercialization of a liquid oral combination drug therapy for the treatment of NAFLD, with potential to also treat other forms of fatty liver disease including alcoholic liver disease (ALD) is intended with the invention. Clinical trials have the potential to confirm biomarkers with lipid and metabolite content and ratio panels effective for NAFLD and other disease diagnosis and prognosis, including inflammatory diseases. Due to the expectation that the invention has the ability to reduce liver, plasma and tissue arachidonic acid (AA) levels, the invention may also prove efficacious for treatment and prevention of inflammatory diseases such as gastrointestinal disease, arthritis, heart disease and cancer.

SUMMARY OF THE INVENTION

The invention is directed in part to a method of treatment, comprising administering to a patient in need thereof an oral dose of lipids in an amount effective to trigger the release of cholecystokinin (CCK) into the duodenum to generate a major release of bile phospholipids from remodeled stores of triglycerides (TAG) in the liver, thereby causing the formation of sequestered and aggregated mixed micelles and vesicles (SAMMVs) in the intestines of the patient which are then eliminated via the bowels of the patient.

The invention is further directed to a method of treatment, comprising administering to a human patient an oral dose of lipids in an amount effective to require the liver to produce an amount of bile effective to trigger the release of catecholamines, annexins and AA metabolites from hepatic cells into bile, which facilitate the fusion and aggregation of micelles and vesicles and therefore SAMMV formation in the intestines.

In certain embodiments, the lipids comprise monounsaturated and n-3 and n-6 polyunsaturated fatty acids in the form of dietary triglyceride (TAG). In certain preferred embodiments, the same fatty acids that trigger the biliary phospholipids release act in conjunction with the phospholipids to form SAMMVs which effectively sequester and bind the biliary phospholipids and other biomolecules for excretion.

In certain embodiments, the lipids comprise the addition of phospholipids and/or free fatty acids to force the formation of SAMMVs that otherwise would not form due to the lack of TAG deposits in the liver, or another cause that produces an inability of the patient's liver to produce sufficient phospholipids to form SAMMVs, for the purpose of forcing SAMMV formation in the intestines for therapy implications and the collection of biomarkers for diagnostic tests.

In certain embodiments, the method of treatment further comprises orally administering to said patient a cathartic to empty the intestines prior to the administration of said oral dose of lipids. Preferably, the dose of cathartic is sufficient to initiate the release of limited amounts of the polypeptide hormone cholecystokinin (CCK) and thereby trigger the release of some bile. The cathartic may be, e.g., a dose of magnesium to empty the intestines prior to the administration of said oral dose of lipids.

The invention is further directed to a method of treatment, comprising the administering to a human patient an oral dose of magnesium in an amount effective to serve as a cathardic and contribute to the fusion and aggregation of vesicles and therefore the formation of SAMMVs due to kinetic and/or thermal energy properties, binding properties, and pH drop produced by the effective dose of magnesium.

In certain embodiments, the oral dose of lipids comprises a standardized 300 ml (10 oz.) solution of lipids, fatty acids, in the form of dietary triglyceride and other ingredients. One or more emulsifiers may be included as well, to create an effective emulsion of the oral dose of lipids.

In further embodiments, the method further comprises administering to said patient after said oral dose of lipids a fluid replenishment drink comprising water, sodium bicarbonate, salt, sugars and optional flavor(s) in an amount effective to prevent dehydration in the day(s) following therapy.

In yet further embodiments, the method further comprises administering to said patient an effective dose of malic acid to improve the malate supply to the liver for the tricarboxylic acid cycle and Acetyl-CoA synthesis of triglycerides (TAG) into phospholipids during therapy.

In yet further embodiments, the method further comprises administering to said patient an effective dose of choline to improve the conversion of triglycerides (TAG) into phospholipids during therapy and to prevent any potential deficiency of choline due to the large demand for choline by Nanoveson™ therapy.

In certain embodiments, the method further comprises the patient self-administering an enema, in the event that the dose of magnesium did not completely evacuate the patient's intestines.

The invention is further directed to a method of treatment, comprising administering to a human patient an oral dose of lipids in an amount effective to require the liver to utilize some stores of phosphatidic acid (PA) for the creation of phospholipids demanded for the emulsification of the oral dose of lipids, thereby making phosphatidic acid unavailable for the synthesis of triglycerides (TAG) in the liver.

In certain preferred embodiments, the patient abstains from ingesting any lipids for about 24 hours prior to administration of an effective dose of a cathartic.

In certain preferred embodiments, the treatment takes place in just over 24 hours from the beginning of the lipid abstinence to the final doses and elimination of the SAMMVs.

In certain embodiments, the method is repeated, e.g., 12 or more times, to reduce the amount of TAG in the liver to a point where no SAMMVs are formed.

The invention is further directed to a method of treatment, comprising implementing therapy by having the patient begin the day by abstaining from ingesting any heavy meals; administering a first dose of a cathartic at about dinner time; administering a second dose of a cathartic about 2 hours after said first dose; and administering an oral dose of lipids in an amount effective to trigger cholecystokinin (CCK) release in the duodenum to generate a major release of bile phospholipids from remodeled stores of triglycerides (TAG) in the liver, thereby causing the formation of sequestered and aggregated mixed micelles and vesicles (SAMMVs) which are then eliminated via the bowels of the patient.

In the method, the liver remodels stores of triglycerides (TAG) and phosphatidic acid to produce phospholipids (lecithin) for bile due to excessively high demand for bile. The bile phospholipids are excreted into the biliary canaliculus to form bile, and into the duodenum to mix with oral dose of lipids. Mixed micelles and vesicles containing medium and long-chain fatty acids in the phospholipids form rapidly. It is preferred that the oral dose of lipids is sufficient to trigger a major release of bile and to trigger the release of an amount of bile phospholipids from the liver that is substantially above the amount of bile in the form of phospholipids in the circulating bile pool.

The invention is also directed to a kit for treating excess triglycerides in the liver of a patient, comprising (i) doses of a cathartic in an amount effective to evacuate the intestines of the patient; and (ii) an oral dose of lipids comprising a solution of lipids and fatty acids.

In the kit, the oral dose of lipids further preferably comprises further comprising one or more emulsifiers to create an effective emulsion of the oral dose of lipids.

The kit preferably further comprises (i) a fluid replenishment drink comprising water, sodium bicarbonate, salt, sugars and optional flavor(s); and/or (ii) a dose(s) of malic acid; and/or (iii) a dose(s) of choline.

It is an object of the present invention to provide a method of treatment, comprising administering to a human patient in need thereof an oral dose of lipids in an amount effective to trigger the release of cholecystokinin (CCK) into the duodenum to generate a release of bile phospholipids from remodeled stores of triglycerides in the liver of the patient, in an amount effective to cause the formation of sequestered and aggregated mixed micelles and vesicles (SAMMVs) in the intestines of the patient which are then eliminated via the bowels of the patient.

In certain embodiments of the present invention, the lipids comprise fatty acids selected from the group consisting of monounsaturated fatty acids, n-3 polyunsaturated fatty acids, n-6 polyunsaturated fatty acids, n-9 monosaturated fatty acids, and mixtures of any of the foregoing, in the form of triglyceride. In certain embodiments, the triglyceride is in the form of dietary triglyceride In certain embodiments of the present invention, the same fatty acids that trigger the biliary phospholipids, act in conjuction with the phospholipids to form SAMMVs, which effectively assist in the sequestering and binding of the biliary phospholipids in SAMMVs for excretion.

In certain embodiments of the present invention, the bile comprises the phospholipids (lecithin) component of bile.

In an embodiment of the present invention, the patient is orally administered a cathartic, e.g. magnesium in an amount effective to empty the intestines prior to the administration of said oral dose of lipids. In another embodiment, the patient is orally administered a cathartic in an amount effective to contribute to vesicle membrane fusion and aggregation to form SAMMVs. In yet other embodiments, the amount of cathartic administered is effective to both empty the intestines prior to the administration of said oral dose of lipids and contribute to vesicle membrane fusion and aggregation to form SAMMVs. In certain embodiments of the present invention, the cathartic is magnesium.

In certain embodiments of the present invention, the dose of magnesium is sufficient to initiate the release of limited amounts of the polypeptide hormone cholecystokinin (CCK) and thereby trigger the release of some bile.

In certain embodiments of the present invention, the dose of magnesium is in the form of a magnesium citrate or magnesium sulfate liquid solution.

In certain embodiment of the present invention, the dose of magnesium is four 300 ml (10 oz.) doses of magnesium citrate liquid solution.

In certain embodiments of the present invention, the oral dose of lipids is dietary triglyceride.

In certain further embodiments of the present invention, the oral dose of lipids further comprises omega-3 fatty acids.

In certain embodiments of the present invention, the oral dose of lipids comprises a standardized 300 ml (10 oz.) solution of lipids, fatty acids, in the form of dietary triglyceride and other ingredients.

In yet further embodiments of the present invention, one or more one or more emulsifiers is added to the solution of lipids, fatty acids, in the form of dietary triglyceride and other ingredients to create an effective emulsion of the oral dose of lipids.

In certain embodiments of the present invention, the patient is orally administered a dose of a cathartic to empty the intestines prior to the administration of said oral dose of lipids and then after said patient is administered the oral dose of lipids, the patient is administered a fluid replenishment drink comprising water, sodium bicarbonate, salt, sugars and optional flavor(s) in an amount effective to prevent dehydration in the day(s) following therapy.

In certain embodiments of the present invention, the patient is administered an effective dose of malic acid to improve the malate supply to the liver for the tricarboxylic acid cycle and Acetyl-CoA synthesis of triglycerides into phospholipids during therapy.

In certain further embodiments of the present invention, in addition to orally administering to the patient a cathartic to empty the intestines prior to the administration of said oral dose of lipids, the patient is further administered an enema in the event that the dose of magnesium did not completely evacuate the patient's intestines.

It is also an object of the present invention to provide a method of treatment, comprising administering to a human patient an oral dose of lipids in an amount effective to require the liver to utilize some stores of phosphatidic acid (PA) for the creation of phospholipids necessary for the emulsification of the oral dose of lipids, thereby making phosphatidic acid unavailable for the synthesis of triglycerides in the liver.

In certain embodiments of the present invention, the patient abstains from ingesting substantially any lipids for about 24 hours prior to administration of an effective dose of a cathartic.

In certain embodiments of the present invention, the method of the invention treats a liver disease, treats a mental disorder, treats a protein misfolding disease, treats a nervous system disorder, improves lipid metabolism and homeostasis in the patient, treats fatty liver disease, treats cholestatic liver diseases and/or treats inspissated bile (IB) and plugs (IBPs).

In certain embodiments of the present invention, the method takes place in just over 24 hours from the beginning of the lipid abstinence to the final doses and elimination of the SAMMVs.

In certain embodiments of the present invention, the method is repeated 12 or more times to reduce the amount of TAG in the liver to a point where no SAMMVs are formed.

In certain embodiments of the present invention, the method is repeated and in yet other embodiments the method is repeated on a chronic basis.

It is a further object of the present invention to pretreating a patient by having the patient begin the day by abstaining from ingesting any heavy meals, for example no or low lipids, or by fasting, then administering a first dose of a cathartic e.g. at about dinner time, administering a second dose of a cathartic e.g. about 2 hours after said first dose and then administering an oral dose of lipids, e.g. about 2 hours after the second cathartic dose, in an amount effective to trigger cholecystokinin (CCK) release in the duodenum to generate a major release of bile phospholipids from remodeled stores of triglycerides in the liver, thereby causing the formation of sequestered and aggregated mixed micelles and vesicles (SAMMVs) which are then eliminated via the bowels of the patient.

In certain embodiments of the present invention, the liver remodels stores of triglycerides and phosphatidic acid to produce phospholipids (lecithin) for bile due to excessively high demand for bile and the remodeling occurs when liver stores of triglyceride consisting of three fatty acids attached to a glycerol molecule backbone undergo transformation into new molecular structures in the form of a phospholipid consisting of two fatty acids attached to a glycerol backbone (a diglyceride), attached to phosphate and choline, and when liver stores of phosphatidic acid, a small phospholipid, is transformed into phospholipids required for bile with the incorporation of choline.

In certain further embodiments of the present invention, the bile phospholipids are excreted into the biliary canaliculus to form bile, and into the duodenum to mix with the oral dose of lipids.

In certain embodiments of the present invention, the mixed micelles and vesicles containing medium and long-chain fatty acids in the phospholipids form rapidly.

In certain embodiments of the present invention, the first dose of cathartic is an about 10 oz. oral dose of magnesium citrate (about 2.5 grams).

In other embodiments of the present invention, the first dose of cathartic is taken at about 6 pm.

In yet other embodiments of the present invention, the second dose of cathartic is an about 10 oz. oral dose of magnesium citrate taken (about 2.5 grams).

In other embodiments of the present invention, the second dose of cathartic is taken at about 8 pm.

In certain embodiments of the present invention, an enema is administered to the patient after the second dose of cathartic to aid in the process of intestinal evacuation.

In certain embodiments of the present invention, the patient goes to bed and sleeps with head slightly elevated on pillows or on the right side in the fetal position after ingesting the oral dose of lipids.

In certain embodiments of the present invention, the oral dose of lipids is administered to the patient in an amount effective to trigger a release of bile and to trigger the release of an amount of bile phospholipids from the liver that is substantially above the normal amount of phospholipids in the circulating bile pool.

In certain embodiments of the present invention, a third dose of cathartic is administered to the patient the next morning following the second dose of cathartic. In further embodiments, the third dose is administered to the patient at about 6 am.

In yet further embodiments of the present invention, a fourth dose of cathartic is administered to the patient about 2 hours following the third dose of cathartic.

In further embodiments of the present invention, an effective dose of a fluid replenishment drink comprising water, sodium bicarbonate, salt, sugars and optional flavor(s) is administered in an amount effective to prevent dehydration in the day(s) following therapy.

In certain embodiments of the present invention, malic acid is administered to the patient for three or more days prior to the treatment in an amount effective to improve liver lipid synthesis.

In certain embodiments of the present invention, a patient suffering from simple fatty liver is administered the treatment repeatedly to reduce the amount of triglycerides in the liver to a point where no SAMMVs are formed and fatty liver has been corrected.

In certain embodiments of the present invention, a patient suffering from cholestasis and/or primary sclerosing cholangitis that involve inspissated bile is administered the treatment on a chronic basis.

In certain embodiments of the invention, the patient fasts all day prior to the initiation of therapy and in other embodiments of the present invention, the patient ingests a light fat-free breakfast and lunch prior to the initiation of therapy.

In certain embodiments of the present invention, clinically significant amounts of stored liver triglyceride (fatty liver) is converted into phospholipids for release through the hepatocyte membrane and into vesicles and micelles for aggregation and elimination in the SAMMVs and AQ.

In certain embodiments of the present invention, increased phospholipids (PL) is released on an ongoing basis with improved enterohepatic circulation.

In certain embodiments of the preferred invention, the large amount of phospholipids released in the bile pushes the concentration of phospholipids in the small intestines beyond the critical micelle concentration (CMC), which creates an environment where lipid micelles can form rapidly.

In certain embodiments of the present invention, the rate of enterohepatic circulation is increased.

In certain embodiments of the present invention, the ongoing conversion of liver triglycerides to phospholipids for bile, facilitates improved ongoing lipid synthesis to treat and prevent fatty liver on an ongoing basis.

In certain embodiments of the present invention, the method of the invention treats liver triglycerides deposits related to non-alcoholic fatty liver disease (NAFLD), cirrhosis, primary biliary cirrhosis (PBC), and other liver diseases.

In certain embodiments of the present invention the amount of arachidonic acid (AA) and the ratio of AA relative to other fatty acids in tissue and blood plasma is reduced. In certain embodiments of the present invention, the ratio of arachidonic acid (AA) to n-3 and other n-6 fatty acids is lowered.

In certain embodiments of the present invention, the method of the invention treats cascade related diseases, arthritis, cancer, gastrointestinal diseases and heart disease related to the AA cascade and the aberrant affects of excessive amounts of AA in the form of free AA and lipid bound AA, elevated triglycerides, elevated LDL, low HDL, pancreatitis, biliary sludge and biliary casts, quantitatively restores whole-body AA homeostasis, removes deposits of AA and AA metabolites from the biliary tract, treats other fatty acid metabolite driven diseases and treats gallstones that form in the gallbladder, intrahepatic bile ducts or extrahepatic bile ducts.

It is also an object of the present invention to provide a kit for treating excess triglycerides in the liver of a patient, comprising at least one dose of a cathartic in an amount effective to evacuate the intestines of the patient; and (ii) an oral dose of lipids comprising a solution of lipids and fatty acids.

In further embodiments of the present invention, one or more emulsifiers to create an effective emulsion of the oral dose of lipids is included in the kit.

In certain embodiments of the present invention, a fluid replenishment drink comprising water, sodium bicarbonate, salt, sugars and optional flavor(s) is included in the kit.

In certain embodiments of the present invention, a dose(s) of malic acid is included in the kit.

In certain embodiments of the present invention, an enema is included in the kit.

In certain further embodiments of the present, the doses of cathartic in the kit are each a 10 oz. oral dose of magnesium citrate (2.5 grams).

In certain further embodiments of the present invention, the doses of cathartic in the kit are four 300 ml (10 oz.) doses of magnesium citrate liquid solution.

In certain further embodiments of the present invention, the dose(s) of malic acid in the kit is in the form of about 800 mg of an oral capsule or tablet.

In certain embodiments of the present invention, the amount of phospholipids released in the bile, after pushing the concentration of phospholipids in the intestines beyond the CMC, creating an environment where lipid micelles form, then pushes the concentration of micelles in the intestines beyond the micellar phase boundary (MPB), which creates an environment where vesicles can form and aggregate rapidly. The MPB is the level of concentration of a compound at which the CMC has been exceeded to a degree that micelles have formed and have reached a degree of concentration at which they can transform into vesicles, In certain embodiments of the present invention, during treatment the pH in the small and/or large intestines is reduced to a point where pancreative phospholipase A2 is suspended or substantially decreased and the AA in the sn-2 position is not cleaved but remains bound to the phospholipid in the SAMMV or in AQ and is excreted. In certain embodiments the pH is decreased below a pH of about 5.8.

In certain embodiments of the present invention, during treatment the pH in the small and/or large intestines is reduced to a level below about the bile salt critical micelle pH (CMPH) causing the bile acids to precipitate out of phospholipid bilayers, micelles, vesicles and SAMMVs to increase the rate of aggregation and excretion of SAMMVs and phospholipids. In certain embodiments the pH is decreased below about the CMpH of 6.0

In certain embodiments of the present invention, lymphatic system circulation and drainage is improved due to improved peristalsis as a result of changes in the fatty acid ratios in lymph and lymphoid organs, and a reduction of AA ratios in lymphoid organs.

In certain embodiments of the present invention, the method may be used as co-therapy with existing modes of therapy for diseases and conditions listed above to improve efficacy and outcomes of those existing modes of therapy.

In certain embodiments of the present invention, clinically significant amounts of cholesterol in the SAMMVs and AQ are removed.

In certain embodiments of the present invention, the carthartic comprises a powder, capsule or tablet form of the magnesium citrate or magnesium sulfate.

In certain embodiments of the present invention, the method of the invention treats skin conditions which are driven by the AA cascade, for example eczema or psoriasis.

In certain embodiments of the present invention, the content of the SAMMVs produced by the method of treatment provide biomarkers for diagnostic tests for diseases, disease states, and medical disorders.

In certain embodiments of the present invention, the content of aqueous solution (AQ) produced by the method of treatment, both when SAMMVs are produced and when they are no longer produced by the therapy, provide biomarkers for the development of diagnostic tests for diseases, disease states, and medical disorders.

In certain embodiments of the present invention, the method of treatment becomes a diagnostic test or part of a diagnostic test for the purpose of providing biomarkers in SAMMVs or AQ samples.

In certain embodiments of the present invention, biomarkers, diagnostic tests and panels are established that use any of the content of the SAMMVs and/or AQ including but not limited to; phospholipids, phospholipid fatty acids, phospholipid bound fatty acids, free fatty acids, AA, AA metabolites, other fatty acid metabolites, catecholamines, annexins, DNA sequencing, bacteria, cholesterol, bile salt, triglycerides, yeast, fungi, viruses, parasites, pancreatic enzymes, enzymes, potassium carboxylates, proteins, choline, methyl esters, hormones and their ratios as compared to standards that become established.

In certain embodiments of the present invention, the biomarkers and diagnostic tests developed include but are not limited to the following diseases; fatty liver, NAFLD, NASH, ALD, fibrosis, cirrhosis, cholestatic liver diseases, other liver diseases, lipid disorders, insulin resistance, metabolism disorders, AA metabolism driven inflammatory driven disorders and diseases including cancer, arthritis, asthma, cystic fibrosis, ASCVD, and any other diseases and disorders for which biomarkers and diagnostic tests are established.

In certain embodiments of the present invention, normal ranges and standards are established for the purpose of establishing and determining disease states.

In certain embodiments of the present invention, a dose of lipids is utilized to trigger a demand for bile phospholipids in excess of the amount of phospholipids available in the existing circulating enterohepatic bile pool, which triggers a remodeling of liver triglycerides into bile phospholipids for the purpose of capturing biomarkers for diagnostic testing.

In certain embodiments of the present invention, the total amount of and ratio of potassium carboxylates, diglycerides, monoglycerides, free fatty acids and other digestive compounds in SAMMVs produced from partial digestion of therapy dietary lipids alone or compared to biliary released compounds serve as biomarkers and diagnostic tests to provide relevant clinical data on the patient's digestive health or other disease states.

In certain embodiments, the method of treatment causes release of AA metabolites, catecholamines and annexins from hepatic cells into bile, thereby promoting fusion and aggregation of micelles and vesicles, and thus facilitating formation of SAMMVs in the intestines of the patient, which are then eliminated via the bowels of the patient.

In certain embodiments of the present invention, the oral dose of magnesium is in an amount effective, due to kinetic and/or thermal energy and membrane binding properties of magnesium, to contribute to the fusion and aggregation of micelles and vesicles, and therefore the formation of SAMMVs.

In certain embodiments of the present invention, the oral dose of lipids or a separate therapy dose lipids comprises the addition of phospholipid (PL) and/or free fatty acids to force the formation of SAMMVs when they otherwise do not form or do not form in sufficient quantities, due to insufficient liver triglyceride deposits available for conversion to PL or other causes, for more effective therapy, biomarker or diagnostic purposes.

In certain further embodiments of the present invention, the patient is administered effective doses of choline to insure sufficient quantities of choline required for the remodeling of liver triglycerides into phospholipids during therapy, and/or to prevent choline deficiency due to therapy.

In certain embodiments of the present invention, the fusion and aggregation of pharmaceutical and drug compounds and other biomolecules into micelle and vesicle membranes and cores in SAMMVs provide the creation of biomarkers and therefore a method for testing drug metabolism, safety and efficacy.

In certain embodiments of the present invention, the treatment is repeated every two weeks or as established by clinical trials until no SAMMVs form with the treatment, with the implication that triglyceride stores and other fusogenic compounds in the liver have been reduced and ongoing enterohepatic circulation has been optimized to improve ongoing lipid synthesis in the liver.

The method of treatment of the present invention is alternatively referred to throughout this document as "Nanoveson™" therapy and the oral dose of lipids is alternatively referred to as the "10 PM solution."

Those skilled in the art will appreciate that therapy in accordance with the invention may be initiated at any time of the day, and therefore the phrase "10 PM solution" and other phrases used to identify administration times are for the convenience of the patient and the reader, and are not meant to be limiting in any way. Likewise, the hypotheses set forth in this document are provided for possible explanatory purposes only, and are not meant to be limiting in any way. For example, the procedure could be done during the day, it would just not be as "pleasant" of an experience. Maybe the times are presented as recommended, but flexible. The cathartic doses may be flexible by 1 to 3 hours in the evening as well, such as 8:00 pm and 9:00 pm, instead of 6:00 pm and 8:00 pm.

ABBREVIATIONS

The following abbreviations are used throughout this document:
AA Arachidonic Acid (n-6 20:4)
AAM Arachidonic Acid Metabolites
AQ Aqueous Solution
ALD Alcoholic Liver Disease
ASCVD Atherosclerotic Cardiovascular Disease
AX Annexins
ATP Adenosine Triphosphate
BSEP Bile Salt Export Pump
CAT Catecholamines
CCK Cholecystokinin
CDP Cytidine Diphosphate
CH2 Carbon-Hydrogen Group—Two single Bonds
CMC Critical Micelle Concentration
CMpH Critical Micelle pH
CoA Coenzyme A
COL Cholesterol
COX Cyclooxygenase
CYP450 Cytochrome P450
DAG Diacylglycerol (aka diglyceride)
DHA Docosahexaenoic Acid (n-3 22:6)
DiHETE Dihydroxyeicosatetraenoic Acids
EET Epoxyeicosatrienoic Acids
EPA Eicosapentaenoic Acid (n-3 20:5)
FA Fatty Acid
FDA Food and Drug Administration
FFA Free Fatty Acid
FOA Funding Opportunity Announcement
GC Gas Chromatography
HDL High-Density Lipoprotein
HETE Hydroxyeicosatetraenoic Acids
IB Inspissated Bile
IBP Inspissated Bile Plugs
LA Linoleic Acid (n-6 18:2)
LNA alpha-Linolenic Acid (n-3 18:3)
LDL Low-Density Lipoprotein
LLC Limited Liability Company
LOX 5-Lipoxygenase
LP Lipolytic Products
LPC Lysophsophatidylcholine
LTD4 Leukotreine D4
LTE4 Leukotreine E4
LUV Large Unilamellar Vesicles
ME Methyl Esters
MONO Monoacylglycerol (aka monoglyceride)
MPB Micellar Phase Boundary MIC Micelles
NAFLD Non-Alcoholic Fatty Liver Disease
NASH Non-Alcoholic Steatohepatitis
NIH National Institutes of Health
OH Hydroxyl Functional Group
P450 Cytochrome P450
PA Phosphatidic Acid (chemistry context)
PA Program Announcement (FDA context)
PC Phosphatidylcholine
PI Phosphatidylinositol
PL Phospholipid
PPLA2 Pancreatic Phospholipase A2
PCM Potassium Carboxylate Micelles
PBC Primary Biliary Cirrhosis
PSC Primary Sclerosing Cholangitis
PUFA Polyunsaturated Fatty Acid
RFP Request For Proposal
ROS Reactive Oxygen Species
SAMMVs Sequestered and Aggregated Mixed Micelles and Vesicles
SPH Sphyngomyelin (a phospholipid)
SuV Small Unilamellar Vesicles
TAG Triglyceride (aka Triacylglycerol)
TP Transport Protein
TXA2 Thromboxane A2
V Vesicle or Liposome
VLDL Very Low-Density Lipoprotein

BRIEF DESCRIPTION OF DRAWINGS

FIG. 10 is a table from Creutz's research demonstrating the fusogenic properties of the listed compounds with the amounts of chromaffin and synexin (annexin VII) utilized in the research, and demonstrates fusogen concentration required to produce the related amounts of vesicle fusion (139).

FIG. 17 is a chart depicting the amount of phospholipids (PL) potentially released by Nanoveson™ therapy. The PL will be remodeled TAG from the liver. Minimal amounts of the fat in the 10 PM solution are expected to be absorbed, while what is absorbed are healthier fatty acids than those being released from the conversion of liver TAG into bile PL and removed.

Figure 18:
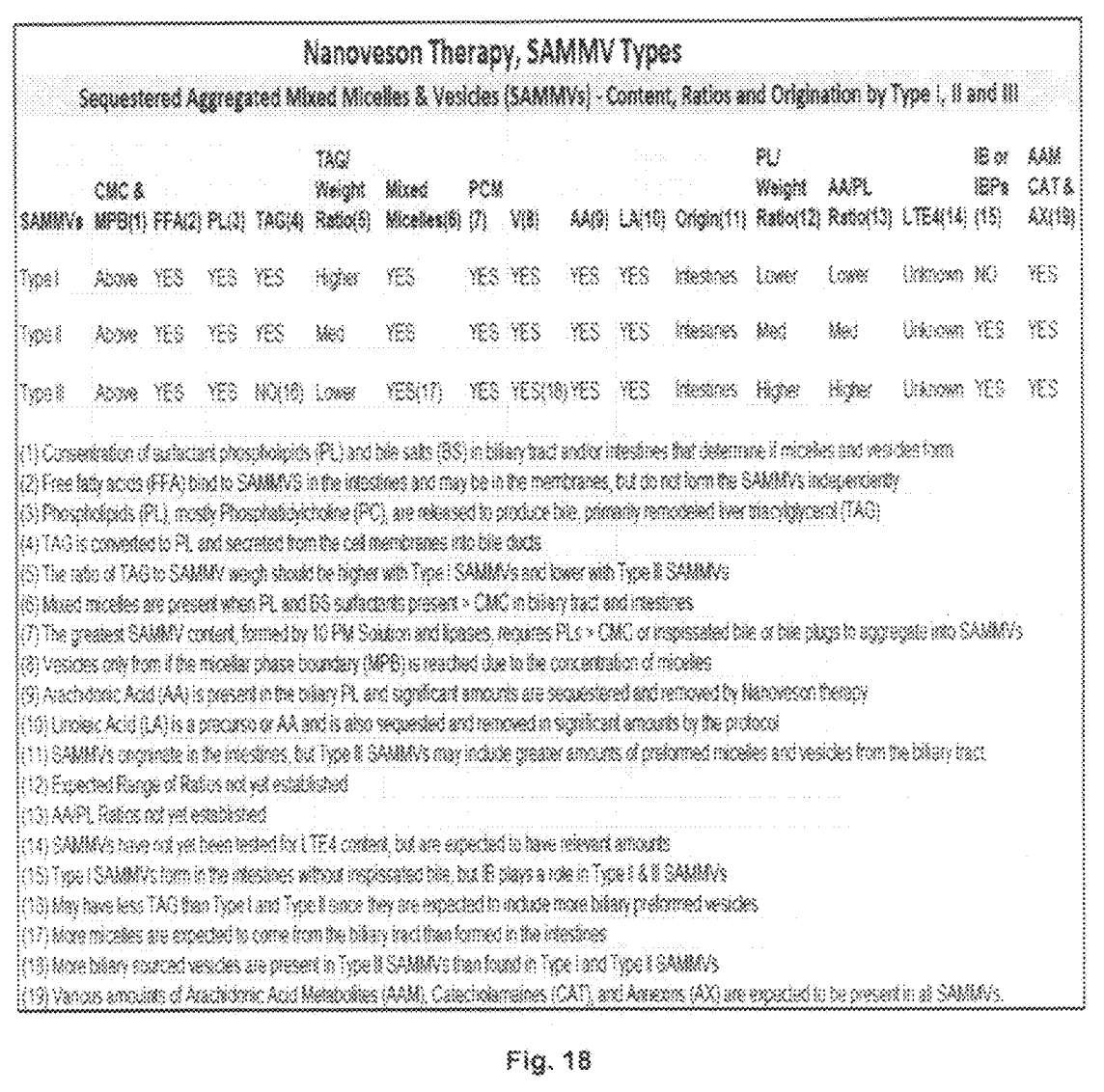

FIG. 18 is a chart demonstrating the three types of SAMMVs expected to form by treatment with Nanoveson™ therapy, with the type dependent upon patient liver and biliary status.

Figure 19:
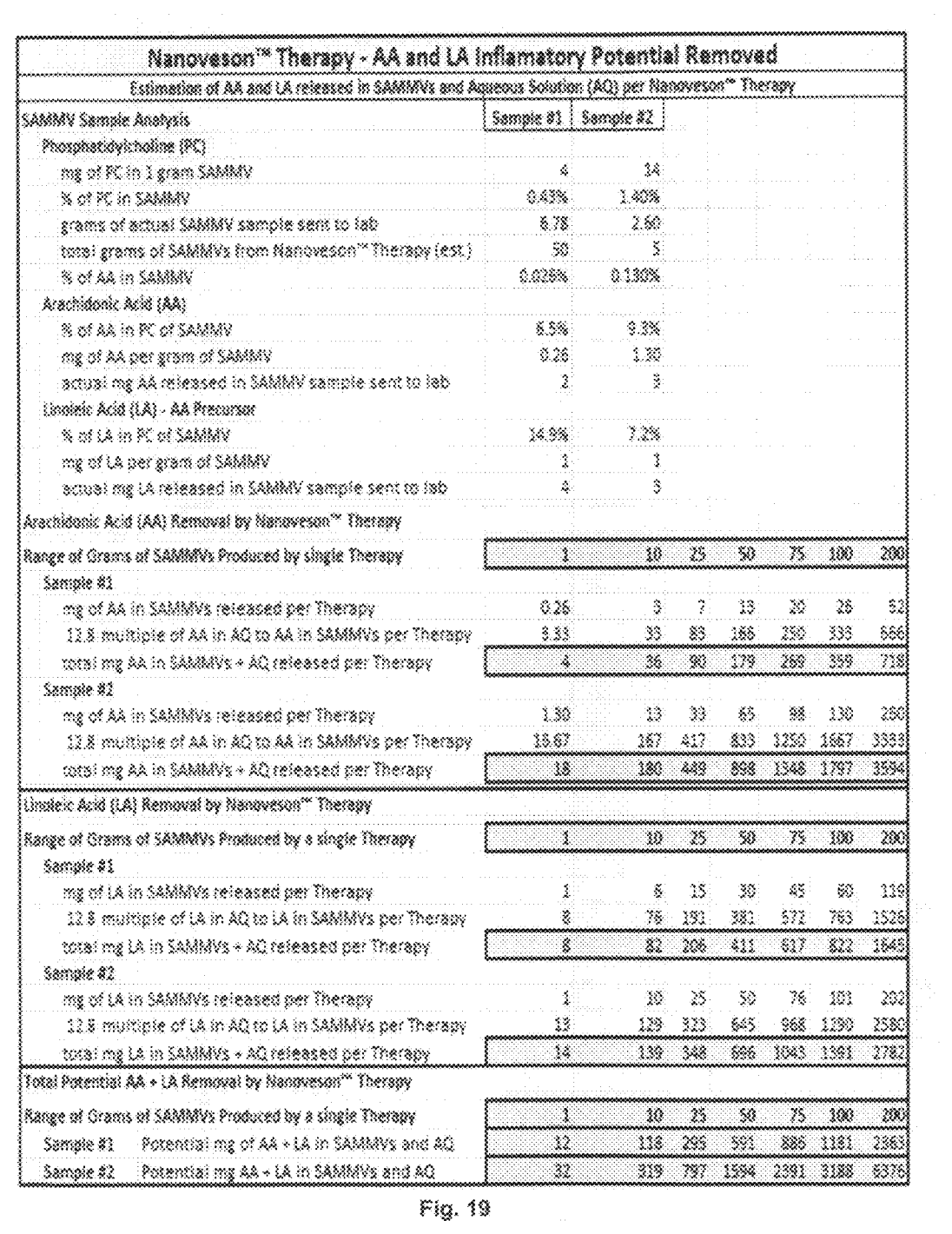

FIG. 19 is a spreadsheet reviewing the amount of AA and LA estimated to potentially be removed by a single Nanoveson™ treatment, based on estimated grams of SAMMVs that are released, and the quantities of AA and LA identified in the actual samples. These numbers can be multiplied by the number of times Nanoveson™ therapy is implemented for the patient.

DETAILED DESCRIPTION OF THE INVENTION

Figure 1:
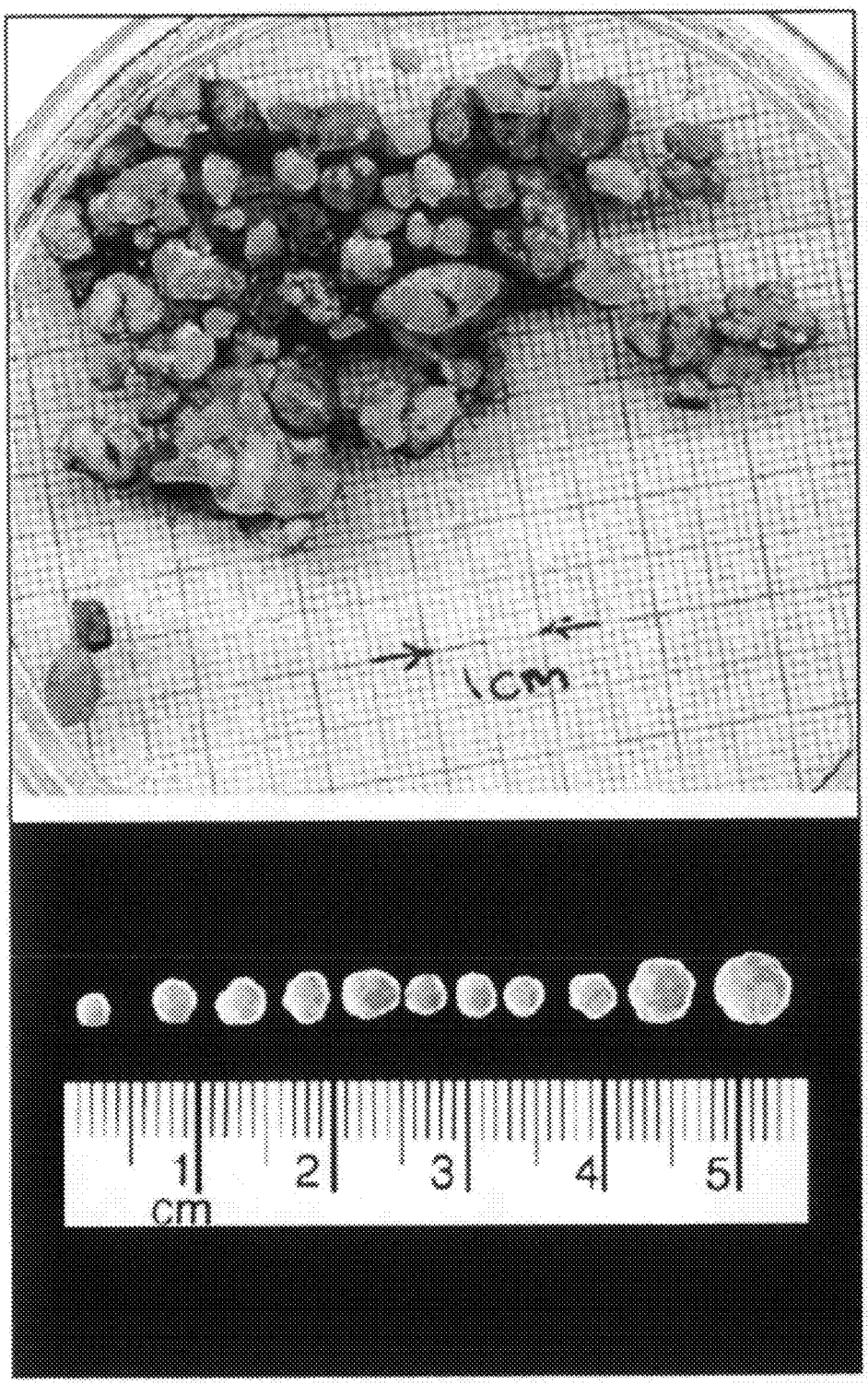
FIG. 1 is an image published in the *Lancet* regarding a patient with actual gallstones removed and other material produced; what is referred to as SAMMVs with Nanoveson™ therapy, and the Lancet research termed micelles of potassium carboxylates "soap stones". The volume of SAMMVs (top), estimated to be ~50 grams, based exclusively on this image, and the gallstones removed surgically (bottom) (21).
Figure 2:
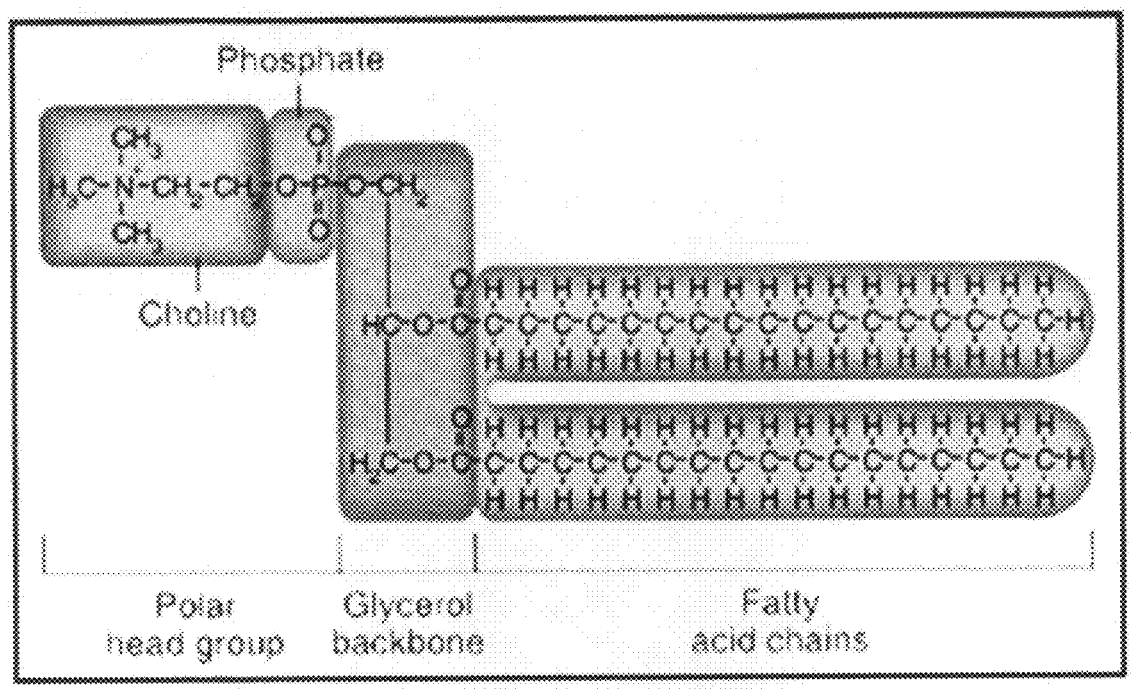
FIG. 2 shows phospholipids: a) phosphate on third —OH group of glycerol; b) have a polar head; c) increased hydrophilicity. Phospholipids can form spheroid structures called vesicles and micelles (130).

Successful tests have been conducted on Nanoveson™ therapy. In a manner analogous with how bile acid sequestrates trap and eliminate bile acids and cholesterol via the intestines. Nanoveson™ therapy triggers the release of significant amounts of phospholipids as bile lecithin from remodeled liver TAG, which is sequestered and eliminated via the intestines. Bile consists of phospholipids, bile acids, cholesterol and other monomers. The critical micelle concentration (CMC) is the concentration level of biliary surfactants in the biliary tract and the intestines that when it is exceeded mixed micelles form. When aggregations of micelles reach and exceed the micellar phase boundary (MPB) they form larger lipid structures called vesicles; phospholipids are a key component of vesicle membranes. In the intestines, these biliary products mix with the digestion lipase products of the large standardized Nanoveson™ 10 PM Solution dose of dietary TAG and citric acid taken orally. The resulting intestinal solution occurs when the active Nanoveson™ therapy ingredient and cathartic, magnesium citrate, and standardized dose timing at 6 PM and 8 PM, have evacuated the intestines of virtually all other digestive matter.

The MPB is the level of concentration of a compound at which the CMC has been exceeded to a degree that micelles have formed and have reached a degree of concentration at which they can transform into vesicles. The MPB will be different for different types of phospholipids, other components, and temperatures.

The digestive products of monoglycerides, diglycerides, free fatty acids and glycerol are expected to be the greatest volume of digestive compounds in the intestines during therapy. Some hydrophobic and polar potassium carboxylate micelles (21) are also expected to form during digestion of dietary ingredients in the 10 PM Solution. The dietary material released from the stomach join the biliary micelles, vesicles and phospholipid, bile salt and cholesterol monomers released from the biliary tract into the duodenum. The high lipid content digestive mixture moving through the duodenum, jejunum and ileum of the small intestines is in aqueous solution (AQ). The AQ in the intestines is the liquid that has not formed micelles and vesicles, with monomer components that may remain above the CMC and MPB, providing an environment where additional mixed micelles and vesicles form and aggregate rapidly.

The Nanoveson™ therapy hypothesis proposes that only when sufficient amounts of TAG are stored in the liver and therefore remodeled and released as bile phospholipids, in response to the 10 PM Solution, is the level of phospholipid surfactant compounds in the small intestines, in combination with other membrane fusogenic compounds, expected to exceed the CMC and MPB to a degree that allows rapid fusion and aggregation of micelles and vesicles. The resulting mixed micelles and vesicles with cores including free fatty acids, TAG, micelles of potassium carboxylates, monodiglycerides, diglycerides and glycerol from the 10 PM Solution and other possible compounds of digestion, aggregate and bind together; i.e., aggregates of aggregates. These aggregates of aggregates are effectively sequestered and aggregated mixed micelles and vesicles (SAMMVs); the SAMMVs are primarily expected to be in the form of aggregated small unilamellar vesicles (SUV) and large unilamellar vesicles (LUV), but may also contain monolayer and multilamelar vesicles with membranes partially consisting of biliary phospholipids. These phospholipids from remodeled liver TAG, when above the CMC and MPB, appear to act as the key sequestering agent. High magnesium levels and their kinetic energy and/or binding properties are expected to contribute to the rapid intestinal aggregation of large unilamellar vesicles (136-138). AA metabolites, catecholamines, and annexins (membrane binding agents), released from hepatic cells during therapy, and dietary free fatty acids, are expected to be included in vesicle membranes and play a role in membrane fusion and vesicle aggregation (139,149,150); these compounds, with phospholipids and bile salts, facilitate SAMMV formation, and have implications for diagnostics and treatment protocols for the therapy and treatment of various liver diseases and other diseases. The amounts of these compounds released from the liver are unknown at this time but are expected to be clinically significant, e.g. they will improve targeted indication outcomes. SAMMVs form in the intestines as a pale green malleable material ranging from 1 mm up to 2 cm in size or larger. Nanoveson™ therapy provides for SAMMV excretion from the intestines within 12 hours of formation. Since the SAMMVs include various amounts of lipids that have undergone saponification into potassium and magnesium carboxylates, they partially consist of "soaps", and therefore can easily be collected as samples for their extensive biomarker content and required diagnostic testing.

The greatest volume of SAMMV content, located in the micelle and vesicle cores, is expected to be digestive hydrolysis products in the form of diglycerides (DAG), monoglycerides, free fatty acids, glycerol and other products of digestion, however, the primary interest focus of the invention are the fusogenic and aggregation properties of compounds located in the membranes of the micelles and vesicles.

Those skilled in the art will recognize that research has indicated that bile phospholipids enter bile pool enterohepatic circulation and are preserved from dilution in the larger pool of lipids (5). One of the keys to Nanoveson™ therapy is that the 10 PM Solution TAG content triggers a digestive demand for biliary phospholipids far in excess of the amount of phospholipids available in the existing enterohepatic bile pool circulation. This demand triggers rapid liver lipid "polymorphism", a remodeling of liver TAG, for the production of significant amounts of biliary phospholipids. SAMMVs are only expected to form during Nanoveson™ therapy when the concentration of micelles and vesicles in the solution in the intestines is sufficiently high due to the amount of biliary phospholipids released from the liver stores of TAG. Fatty acid fecal panels from SAMMVs produced during Nanoveson™ therapy will potentially provide for the establishment of values to determine levels of liver TAG and other liver diseases.

It is expected that a liver without 1) sufficient stores of TAG, or 2) a liver without preexisting bile nucleation and inspissation in the intrahepatic and extrahepatic biliary tract, to act as a nuclei for additional intestinal SAMMV formation, will produce no SAMMVs from Nanoveson™ therapy. Even mild biliary stasis and/or mild fatty liver may produce levels of stored liver TAG and/or nucleation and inspissation in the form of aggregated vesicles that produce SAMMVs. The greater the degree of excess TAG stored in the liver, the greater degree CMC and MPB is exceeded and the larger the size and the greater the volume of SAMMVs produced by Nanoveson™ therapy; and the greater number of Nanoveson™ treatment procedures required to reduce excess liver TAG to an optimal level. When no SAMMVs are formed and excreted by the standardized Nanoveson™ treatment, it is hypothesized that the liver has been restored to a healthier balance of lipids in the form of free fatty acids, phospholipids and TAG. Biliary stasis producing bile inspissation and nucleation has been removed, and enterohepatic circulation of the bile pool has been returned to an optimal rate.

It is hypothesized that through multiple Nanoveson™ therapy treatments lipid homeostasis in the liver can be obtained and elevated liver enzymes can be normalized; phospholipid release and uptake in the bile pool during enterohepatic circulation can be optimized. Clinical trials will confirm if Nanoveson™ therapy will prove efficacious when the concentration of phospholipids from converted TAG is too low and drops below the CMC and/or MPB, and no SAMMVs form with Nanoveson™ therapy. Clinical trials that establish the efficacy of Nanoveson™ therapy as a treatment option for the indication of NAFLD, both with the formation of SAMMVs and when they are no longer formed by Nanoveson™ therapy are required. Nanoveson™ therapy is expected to have a good safety profile due to long-term safety profiles of the active compounds, and thus may be an option for patient treatment of indicated diseases where existing pharmaceutical options are contraindicated, which is a growing problem, especially due to liver disease. At the present time, Nanoveson™ therapy has not been approved and is not currently approved as treatment or therapy for any disease or condition. Nanoveson™ therapy has not been tested for toxicity and safety now that section above claims has been removed.

Circulation of the bile pool phospholipids, bile acids, and cholesterol in the form of enterohepatic circulation play a role in regulation of available AA. Significant amounts of biliary AA are present in the SAMMVs. Digestive pancreatic phospholipase A2 (PPLA2), cleaves AA from the sn-2 position of the phospholipid (16). During Nanoveson™ therapy, the acidity of the 10 PM solution, osmosis, and/or exhaustion of available pancreatic bicarbonate from the cathartic is expected to drop the pH in the small intestines so that PPLA2 is suppressed or eliminated. Phospholipids rich in AA, and even larger amounts of the AA precursor 18:2 linoleic acid (LA) are not metabolized; they are instead bound and sequestered in the SAMMVs and eliminated. It is presently unknown how much AA is excreted as degraded metabolites during Nanoveson™ therapy in the form of leukotreine E4 (LTE4), CYP450 pathway products or other AA metabolites. Very limited amounts of "free" AA unbound to phospholipids have been identified in SAMMVs.

The profound event that has occurred, when Nanoveson™ therapy no longer produces SAMMVs, when the 10 PM Solution ingredients are formulated correctly and therapy protocols are followed, is that a fundamental change has occurred in the amount and makeup of the stores of TAG in the liver, and therefore the release of phospholipids and other sequestering compounds into bile. Nanoveson™ therapy is expected to optimize enterohepatic circulation by removing excess fat deposits from the liver, which restrict lipid synthesis in the liver, and by removing biliary sludge and inspissated bile (IB) and some inspissated bile plug (IBPs), thereby reducing or eliminating bile stasis and increasing the viscosity and fluidity of the bile in the bile pool.

Enterohepatic circulation is responsible for quantitatively maintaining overall body AA homeostasis (45) and may be restricted by excessive fat deposits in hepatocytes. Nanoveson™ therapy will reduce the availability of free AA for the AA cascade, which plays a primary role in inflammatory diseases and cancer growth. The release of AA in the form of LTE4 and CYP450 byproducts and other inflammatory AA metabolites released regularly in bile will increase with improved ongoing enterohepatic circulation. Clinical trials are expected to include metabolic syndrome biomarkers and AA blood plasma ratios to observe potential change in the ratios and the subsequent affect on AA metabolite (eicosanoid) driven diseases, such as gastrointestinal disease, cardiovascular disease, asthma and cancer.

There is a significant and growing need for non-invasive and cost effective biomarkers and diagnostic tests for liver diseases and other diseases. SAMMV formation occurs due to the biochemistry produced by the interaction of compounds in the intestines from a clinically significant amount of rapid liver lipid polymorphism and bile release during Nanoveson™ therapy. SAMMV's therapeutically manipulated "nanobiotechnology" driven construction sequester metabolic compounds released by the liver during therapy and therefore provide a rich source of biomarkers and important clinical data related to the patient's liver condition and liver related disease states. The biomarkers sequestered in SAMMVs can be used to design diagnostic tests. Nanoveson™ therapy in conjunction with existing diagnostic tools and biomarkers, such as lipid panels, blood panels for lipids and fatty acids, ultrasounds and other diagnostic tools will serve to develop and establish disease treatment protocols.

The following content and their ratios found in SAMMVs and AQ produced by Nanoveson™ therapy will provide biomarkers for diagnostic tests; phospholipids, specific phospholipid bound fatty acids, fatty acids, fatty acids metabolites, AA, AA metabolites, catecholamines, annexins, choline, methyl esters, proteins, albumin, antibodies, nucleic acids, DNA, bacteria, cholesterol, bile salts, TAG, yeast, fungi, viruses, parasites, pancreatic enzymes, other enzymes, and any additionally discovered SAMMV content, or other content added to the therapy in the form of PL, FFA, nanoparticles or other compounds to change or enhance SAMMV fusion and aggregation activity. Biomarkers and diagnostic tests for fatty liver, NAFLD, NASH, ALD, fibrosis, cirrhosis, cholestatic liver diseases, other liver diseases, lipid disorders, insulin resistance, metabolism disorders, AA driven inflammatory disorders and diseases, cystic fibrosis, ASCVD, and various other diseases and disorders are anticipated to be established. The total amount of and ratio of potassium carboxylates and other digestive compounds in SAMMVs produced from partial digestion of therapy dietary lipids and as compared to biliary released compounds will also provide for biomarkers and relevant clinical data on the patient's digestive health.

Those skilled in the art recognize that fatty liver is a medical condition that occurs when excessive levels of triglycerides (TAG) are stored in the liver. It is estimated that approximately one third of the adult population of the United States has hepatic steatosis (fatty liver) (1) in the form of NAFLD. This amounts to approximately 60 million cases. In many respects, NAFLD and its comorbid conditions are an epidemic in the U.S. and other developed countries. Hepatic steatosis can lead to oxidative stress, mitochondrial dysfunction, gut-derived lipopolysaccharide and adipocytokines that promote hepatocelluar damage, inflammation and progressive liver disease (2). The rate of NAFLD in obese individuals is 76%, which compares with 16% in non-obese individuals (2,6), and the increase in the number of obese individuals shows no sign of abating.

There are currently no approved products to address the significant need for a treatment of NAFLD. Nanoveson™ therapy, which has the potential to effectively address this market, can have a remarkable and rewarding impact on human disease and suffering.

The challenge and opportunity of treating NAFLD is that it has direct implications for many other major and chronic diseases. NAFLD is associated with features of the metabolic syndrome and related diseases including insulin resistance (2). The accumulation of hepatic TAG leads to hepatic insulin resistance by interfering with tyrosine phosphorylation of insulin receptor substrates, which leads to overall insulin resistance (2,7,8).

The disease known as cholestasis, aka cholestasia, and similar liver diseases, that involve inspissated bile (IB) and inspissated bile plugs (IBPs) or biliary concretions and are sometimes comorbid with fatty liver require consideration in conjunction with fatty liver. Such related liver diseases are expected to have implications and possible complications, but may also have the potential to be treated by Nanoveson™ therapy. The presence of gallstones may also prove to complicate and create risk for Nanoveson™ as a treatment option.

Liver disease often makes treatment of many major chronic ailments by leading pharmaceutical products contraindicated. Patients with liver diseases that make them contraindicated for leading therapeutic approaches are expected to be candidates for Nanoveson™ treatment, due to its anticipated safety profile. With the rise of liver disease, the number of patients that need new therapeutic treatment options due to contraindications represents a very large market, thus creating a major opportunity for a new therapeutic option with a high safety profile that is liver friendly.

Materials Used in the Invention

Nanoveson™ represents a novel approach to treating NAFLD, other liver diseases and related diseases. By treating NAFLD and comorbid diseases, where there are currently no other therapeutic options, it is expected to prove to be a major product and lifesaver. For other diseases that may receive indication for treatment by Nanoveson™, it is possible that physicians and their patients will most often prefer other available therapeutic options. For those with liver disease that make them contraindicated for currently established treatment modalities, Nanoveson™ may be their only option. Many will prefer Nanoveson™ therapy to current options, making it a primary therapy of choice.

Although the biochemistry and lipid polymorphism activity generated to produce Nanoveson's™ efficacy is complex, it is a relatively straightforward therapy. The key to Nanoveson™ therapy is the use of the active ingredient of a large oral dose of lipids, primarily monounsaturated and n-3 polyunsaturated fatty acids in the form of dietary TAG, to trigger CCK in the duodenum to generate a major release of bile, specifically the phospholipids (lecithin) component of bile from remodeled stores of TAG in the liver. Remarkably, the same fatty acids that trigger the biliary phospholipids assist in the sequestering and binding of the biliary phospholipids in SAMMVs for excretion. There are multiple products required for therapy that will be packaged in a complete Nanoveson™ therapy kit for sales and distribution.

Nanoveson™ MCL (NV-1001):

Nanoveson™ MCL (NV-1001) is a magnesium citrate liquid solution packaged in four 300 ml (10 oz.) bottles for four different doses during the therapy. Each bottle will contain 2.5 grams or more of magnesium in the form of magnesium citrate. The solution will contain a natural lemon-lime flavoring and sweetener. Other ingredients will be included as determined necessary in clinical trials and as required.

| Nanoveson MCL (NV-1001) - Magnesium Citrate Liquid | | | |
|---|---|---|---|
| | grams | ml | oz. |
| Magnesium Citrate | 15 | | |
| Xylitol (sweetner) | 3 | | |
| Carbonated Distilled Water | | 296 | 10 |
| Natural Lemon Lime Flavoring | | | |
| Other Information: | | | |
| Magnesium (as magnesium citrate) | 2.49 | | |
| Citric Acid (as magnesium citrate) | 12.51 | | |

A liquid magnesium sulfate version of the laxative product listed as Nanoveson™ MCL (NV-1001) will be Nanoveson™ MSL. Tablet, Nanoveson™ MCT/MST and powder Nanoveson™ MCP/MSP versions of both magnesium citrate and magnesium sulfate will also be pursued for physician and patient preferences and for competitive and patent reasons.

Nanoveson™ 10 PM Solution (NV-1002):

Nanoveson™ 10 PM Solution (NV-1002) is a standardized 300 ml (10 oz.) solution of lipids, fatty acids, in the form of dietary triglyceride and other ingredients; citrus juice used in preclinical testing will be replaced in the final product with a combination of citric acid, potassium, various sugars and distilled water. The unique combination of fatty acids facilitates the method of action and efficacy of Nanoveson™ therapy. The high dose of fatty acids triggers liver TAG remodeling to phospholipids for excretion during Nanoveson™ therapy. The large dose of omega-3 fatty acids in the 10 PM solution also provides for liver lipid remodeling and rebalancing to healthier fatty acids during the therapy; however, stability may be an issue with the omega-3 fatty acids. Specific amounts of individual fatty acids in the 10 PM Solution is subject to change. Some fatty acids may be removed and other fatty acids may be added. Adding small amounts of AA and PL are expected to have a major impact on the amount of SAMMV formation, and therefore the potential absorption of dietary lipids, and therefore will be evaluated. Emulsifiers may be added to create an effective emulsion of the product in an attempt to improve patient satisfaction and compliance. Other ingredients, including possible preservatives, will be included as required. Amounts of potassium will be determined for Phase I trials and adjusted during Phase II trials to alter the formation of potassium carboxylates and their impact on the formation and size of SAMMVs, and the impact on absorption of dietary fats during therapy.

Nanoveson 10 PM Solution (NV-1002)

| Trivial Name | IUPAC Name | Type of Fat | Carbons | Omega | Low | High | Mean(2) | 10 PM Solution (%) | ml | oz. | grams |
|---|---|---|---|---|---|---|---|---|---|---|---|
| Active Ingredients Lipid Triglycerides/Fatty Acids - Combined Natural Sources(1) | | | | | | | | | | | |
| Oleic acid | (9Z)-octadec-9-enoic acid | mono-saturated | 18:1 | n-9 | 45.25% | 69.50% | 57.38% | 22.95% | 67.9 | 2.3 | |
| Palmitic | hexadecanoic acid | saturated | 16:0 | n-0 | 6.63% | 16.75% | 11.69% | 4.68% | 13.8 | 0.5 | |
| Linoleic | cis,cis-9,12-octadecadienoic acid | poly-unsaturated | 18:2 (9,12) | n-6 | 6.88% | 22.50% | 14.69% | 5.88% | 17.4 | 0.6 | |
| Palmitoleic acid | cis-hexadec-3-enoic acid | mono-saturated | 16:1 | n-7 | 0.23% | 2.63% | 1.43% | 0.57% | 1.7 | 0.1 | |
| alpha-Linolenic | all-cis-octadeca-9,12,15-trienoic acid | poly-unsaturated | 18:3 (9,12,15) | n-3 | 11.75% | 14.88% | 13.31% | 5.33% | 15.8 | 0.5 | |
| Stearic | octadecanoic acid | saturated | 18:0 | n-0 | 1.13% | 5.25% | 3.19% | 1.28% | 3.8 | 0.1 | |
| Myristic | detradecanoic | | 14:0 | | 0.00% | 0.08% | 0.04% | 0.02% | 0.0 | 0.0 | |
| Margaric | heptadecanoic | | 17:0 | | 0.00% | 0.38% | 0.19% | 0.08% | 0.2 | 0.0 | |
| Unknown | Unknown | | 17:1 | | 0.00% | 0.45% | 0.23% | 0.09% | 0.3 | 0.0 | |
| Arachidic | icosanoic | | 20:0 | | 0.00% | 0.60% | 0.30% | 0.12% | 0.4 | 0.0 | |
| Behenic | docosanoic | | 22:0 | | 0.00% | 0.15% | 0.08% | 0.03% | 0.1 | 0.0 | |
| Lignoceric | tetracosanoic | | 24:0 | | 0.00% | 0.08% | 0.04% | 0.02% | 0.0 | 0.0 | |
| | | | | | 71.85% | 133.23% | 102.54% | 41.02% | 121.40 | 4.10 | |

Other ingredients include the following in the form of citrus juice and/or individual ingredients:

| | | | | | | | | | | | |
|---|---|---|---|---|---|---|---|---|---|---|---|
| Citric acid (from citrus sources) | | | | | | | | | | | 15.0 |
| Potassium | | | | | | | | | | | TBD |
| Sugars | | | | | | | | | | | TBD |
| Emulsifiers | | | | | | | | | | | TBD |
| Flavoring | | | | | | | | | | | TBD |
| Distilled Water | | | | | | | | 59.00% | 177.0 | 6.0 | |
| TOTAL Content | | | | | | | | 100.02% | 298 | 10 | |
| | | | | | | | | | | | |
| TOTAL Grams of Fat from Dietary TAG | | | | | | | | 106 | | | |

Source: Lipid content and range calculations are from the International Union of Pure and Applied Chemistry Lexicon of Lipid Nutrition (133)

Note (1):
Fatty acid sources are a combination of dietary lipids from triglycerides (TAG) in olive and linseed (flax) oils.

Note (2):
102% mean due to IUPAC data mean calculation

A version of the 10 PM Solution product for diagnostic tests on patients that do not have fatty liver and therefore do not form SAMMVs would include PL and/or AA to force vesicle fusion for the intestinal production of SAMMVs to sequester liver content for biomarkers and diagnostic testing. The formulation, standardization and refining for manufacturing of the lipids in the 10 PM Solution is critical. The amount of free fatty acid monomers vs. TAG is expected to have a significant impact on vesicle fusion (139) and SAMMV aggregation, and therefore has significant treatment, biomarker and diagnostic implications for the therapy.

Nanoveson™ Replenish (NV-1003):

Nanoveson™ Replenish (NV-1003) will contain water, sodium bicarbonate, salt, sugars, lemon-lime flavor in a 32 oz. bottle. The replenishment drink is to be used as a standardized liquid to prevent dehydration by Nanoveson™ therapy in the day(s) following therapy. Patients could chose to use OTC brand products for dehydration. A unique formulation for Nanoveson™ therapy would be ideal. Other ingredients will be included as determined necessary in clinical trials and as required. Dehydration is a potential side-effect and risk and should be carefully avoided.

| Nanoveson Replenish (NV-1003) (64 ounces) (serving size 8 oz.) | |
| --- | --- |
| | per serving mg |
| Total Fat | 0 |
| Sodium | 110 |
| Potassium | 30 |
| Sugars | 14 |
| Ingredients: | |
| Water | |
| Glucose Syrup | |
| Sucrose | |
| Citric Acid | |
| Sea SaNV | |
| Sodium Citrate | |
| Potassium Phosphate | |
| Natural Lemon Lime Flavors | |

Nanoveson™ M (NV-1004):

Nanoveson™ M (NV-1004), if clinical trials prove statistically significant improvement in efficacy, Nanoveson™ M will be a 800 mg tablet or capsule form of malic acid to improve the malate supply to the liver for the tricarboxylic acid cycle and Acetyl-CoA synthesis. However, malate is not expected to be essential to Nanoveson™ therapy efficacy.

| Nanoveson M - Malic Acid (NV-1004) (capsules or tablets) | |
| --- | --- |
| | mg |
| Malic Acid | 800 |

Nanoveson™ C (NV-1005)

Nanoveson™ C (NV-1005) will be a choline supplement; if found to provide improvement in therapy efficacy, a choline supplement may be added to the Nanoveson™ therapy regimen. Choline is a key substrate in the remodeling "polymorphism" of TAG to PL. The amount of TAG conversion to PL produced by Nanoveson™ therapy is expected to create a major demand for choline by the patient. It is not presently expected, but the demand for choline significantly beyond normal physiological conditions could potentially lead to a choline deficiency by patients undergoing multiple Nanoveson™ therapies. A deficiency in choline has been linked to fatty liver (170,171,172).

| Nanoveson C - Choline (NV-1005) (capsules or tablets) | |
| --- | --- |
| | mg |
| Choline | 500 |

Nanoveson™ therapy involves a timed preparation with a single day of dietary changes to avoid consumption of dietary lipids, and then the oral consumption of the active Nanoveson™ therapy ingredients. The entire Nanoveson™ therapy takes place in just over 24 hours from the beginning of the lipid abstinence to the final doses and elimination of the SAMMVs on the next morning. The following reviews Nanoveson™ therapy steps and requirements, while review of the biochemical reactions to these Nanoveson™ therapy steps is under the Biochemistry of Nanoveson™ therapy section to follow.

Nanoveson™ Therapy Administration Steps:

Nanoveson™ therapy is advised to be implemented over a Friday or Saturday evening for those that are employed during the week.

On the day of Nanoveson™ therapy, lipids (fats) should not be consumed (note: the fat abstinence is not anticipated to be absolutely required for Nanoveson™ therapy to be effective, but will likely make it easier on the patient, and may in fact be discovered to make it more effective).

Light fat-free breakfast and lunch the day of Nanoveson™ therapy, e.g. oatmeal for breakfast and fat-free vegetables such as soup for lunch.

Fasting all day is a reasonable option for the day of therapy. Fasting the entire day will make cathartic intestinal evacuation easier and may make the patient more comfortable for the therapy.

Fasting may be established as a standard recommendation for Nanoveson™ therapy for some patients, compared to fasting requirements for colonoscopy, but is not expected to be required.

Fasting is expected to be required when the therapy is utilized for biomarker and diagnostic purposes, since "any" dietary consumption of free fatty acids, specifically AA and especially phospholipids (PL) will have a significant impact on the formation, volume and content of SAMMVs.

Only therapy while fasting will determine the amount of SAMMV formation as a result of liver, gallbladder and biliary sourced PL. Consumption of dietary PL will greatly distort SAMMV formation results. Allowing consumption of some foods will invariable result in the consumption of foods with FFA, AA and PL.

After 2 PM no solid food should be consumed, and apple juice or water for liquids.

At 6:00 PM the first 10 oz. oral dose of magnesium citrate is taken (2.5 grams).

At 8:00 PM the second 10 oz. oral dose of magnesium citrate is taken (2.5 grams).

Alternative timing and spacing of the doses of the cathartic are expected to be established and will likely be tested in Phase II trials; such as an 8 PM and 9 PM dose to accommodate schedules and encourage compliance.

From 8:00 PM to 9:30 PM the intestines are expected to be evacuated by the magnesium citrate.

If intestines have not been evacuated by 9:30 PM the physician may advise the patient that to be more comfortable during therapy an enema can be used to assure the process of intestinal evacuation.

With no lipid consumption all day, minimal amounts of bile are released, so liver and biliary tract bile pressure is expected to be marginally elevated above normal.

At 10 PM the Nanoveson™ 10 PM Solution is taken orally.

The patient goes directly to bed and sleeps with head slightly elevated on pillows or on the right side in the fetal position.

The 10 PM solution moves quickly through the stomach to the duodenum where the excessive dietary fat content of the solution triggers a major release of bile.

The amount of fat in the Nanoveson™ 10 PM Solution, following the lipid fast, triggers a considerable demand for bile phospholipids (lecithin), substantially above what is available in the form of phospholipids in the circulating bile pool.

The liver remodels stores of TAG and phosphatidic acid to produce phospholipids (lecithin) for bile due to excessively high demand for bile and reduced or eliminated enterohepatic circulation of PL during therapy.

The bile phospholipids are excreted into the biliary canaliculus to form bile, and into the duodenum to mix with oral lipids consumed in the 10 PM solution.

The biliary phospholipid surfactants exceed the critical micelle concentration and the micellar phase boundary for the phospholipid surfactants in the intestines.

Any AA cleaved from PL by PPLA2, and therefore in the form of free AA, and AA metabolites are expected to have an impact on SAMMV formation.

The presence of catecholamines and annexins released from the liver are expected to play a role in vesicle fusion and aggregation.

Magnesium and its kinetic and/or thermal energy and interaction with annexins possibly contributes to the formation of the SAMMVs.

Mixed micelles and vesicles containing medium and long-chain fatty acids in the phospholipids form rapidly.

Preformed vesicles in the biliary tract released into the intestines may not be solubilized by bile salts due to the low pH and are expected to grow rapidly.

The intestinal environment is right for the production of SAMMVs through micelle and vesicle aggregation.

At approximately 6 AM the following morning the third oral dose of 10 ounces of magnesium citrate is taken (2.5 grams).

If required, an 8 AM 8 oz. oral dose of the magnesium citrate is also taken (2.5 grams). The 8 AM dose is expected to be established as optional and may be eliminated all together.

An alternative single morning cathartic dose at 4 AM or 5 AM will also be tested in Phase II trials to accommodate working schedules. After such an early dose, most individuals may be able to be at work from 8 AM to 9 AM, thus improving compliance.

The SAMMVs are excreted via the bowels by the cathartic effect of the magnesium citrate and natural intestinal function; typically the bulk of the SAMMVs are excreted before 12 noon, completing the full Nanoveson™ therapy in less than 24 hours.

Nanoveson™ Replenish is taken orally during the day after 10 AM to prevent dehydration from the prior large cathartic doses of magnesium citrate.

Nanoveson™ is supplementation with tablet oral doses of malic acid to improve liver lipid synthesis for three or more days prior to Nanoveson™ treatment, but will only be included as efficacy is indicated (see discussion under Biochemistry of Nanoveson™).

Nanoveson™ C is a supplementation with tablet or capsule of choline as choline is a key substrate for the conversion of TAG to PL and is implicated in fatty liver. Substantial TAG to PL remodeling is a key aspect of Nanoveson™ therapy. Choline will be added to Nanoveson™ therapy for a period before and/or after therapy if proven to improve efficacy with clinical trials and as required.

After two weeks or sooner if required Nanoveson™ therapy can be repeated.

Patient and physician need to be aware of potential side effects and watch for any adverse side effects (see Side Effects).

For simple fatty liver, it is expected that Nanoveson™ therapy may need to be repeated 12 or more times to reduce the amount of TAG in the liver to a point where CMC and the MPB is not exceeded to a degree that allows for SAMMVs to form and fatty liver has been corrected, but may be effective in as few as 3 times. More complex and advanced liver disease, such as cholestasis and primary sclerosing cholangitis that involve inspissated bile, if they can be treated by Nanoveson™ therapy at all, may require a significant additional number of Nanoveson™ treatments. Without exercise, and if the intake of fats is excessive, i.e. more TAG is being consumed and stored in the liver than removed by regular metabolism and Nanoveson™ therapy, it is likely that the formation of SAMMVs will continue indefinitely. Nanoveson™ therapy will likely still prove efficacious with such a patient by improving enterohepatic circulation and remodeling liver lipids by replacing less healthy saturated stores of lipids with healthier monounsaturated and n-3 polyunsaturated lipids.

DETAILED DESCRIPTION OF INVENTION BIOCHEMISTRY

A detailed understanding of the biochemical reactions, lipid polymorphism and nanobiotechnology cascade produced by Nanoveson™ therapy and the process of biliary phospholipid release provides the explanation for the inevitable end of SAMMV production, resulting from patient compliance with Nanoveson™ therapy, and the explanation for the physiological impact on a number of major disease classes.

Therapy that is similar to Nanoveson™ therapy has been promoted, but advocates have not discovered the actual biochemistry at work. They do not utilize the ideal materials/ingredient combinations, and distribute potentially dangerous information. Misleading information is available to the public from those without knowledge of the lipid polymorphism and nanobiochemistry that are fundamental to the therapy. For this reason, they do not understand the importance of the fatty acid formulation of the 10 PM solution and its lipid remodeling importance, the risk of excessive amounts of pro-inflammatory linoleic acid (n-6 18:2) they recommend, without balanced intake of linolenic acid (n-3 18:3), or other n-3 fatty acids, or the role played by the magnesium cathartic and other ingredients that play a role in SAMMV fusion and aggregation.

Advocates have promoted use of comparable therapy for the removal of gallstones from the gallbladder and the liver, believing that the sequestered aggregated mixed micelles and vesicles, or SAMMVs, were gallstones. Ahmed et al observed that 90% of gallstones in the gallbladder are made of cholesterol (more than 50% cholesterol) or mixed (20 to 50 percent cholesterol) gallstones. The remaining 10 percent of gallstones are pigmented stone, which have less than 20 percent cholesterol (169). SAMMV examples presented have consistently been found to be 1% cholesterol with clear evidence they undergo fusion and aggregation in the intestines, i.e., they are not gallstones. Those skilled in the art will recognize that the SAMMVs produced by the invention are self-organized lipid structures formed in the intestines based on established lipid polymorphism and nanobiotechnology membrane lipid principles with major biological implications.

Aggravation of actual gallstones in the gallbladder and biliary tract may in fact be a potential negative side effect to Nanoveson™ therapy as reviewed below. Removal of small gallstones, if it does occur during Nanoveson™ therapy, is not the important physiological process occurring through Nanoveson™ therapy. The inaccurate information needs to be corrected and the actual lipid polymorphism and nanobiotechnology and efficacy of Nanoveson™ therapy for targeted indications through clinical trials needs to be established for the commercialization of Nanoveson™ therapy products.

In April 2005 the *Lancet* published an article on tests carried out relating to a patient that had excreted what they believed to be gallstones, but were what are termed here as SAMMVs. The patient in fact had actual gallstones removed by surgery (21). The authors analyzed the patient's produced lipid aggregates. However, the authors identified what we have term as SAMMVs as insoluble potassium carboxylate micelles or "soap stones". They proposed that the micelles were produced by gastric lipases on the TAG in the oil that produced carboxylic acids followed by saponification into aggregated micelles. They reported that the content was 75% from the original material (oral dose), and did not provide comprehensive details of their lipid and fatty acid analysis; i.e., the details on the research conducted were limited. They did not distinguish between different lipid classes and fatty acids in the carboxylate micelles to come to the 75% total. The 75% is expected to have included products of digestion hydrolysis, such as diglycerides/diacylglycerol (DAG), monoglycerides/monoacylglycerols and glycerol, but the documentation was limited. Nanoveson™ therapy research has only found SAMMVs to be ~2% to ~4% soaps following acidification to discover the amount of soaps in the lipid aggregates.

The focus of research in the *Lancet* was a patient with actual gallstones whose health and life were jeopardized by inaccurate information about the biochemistry taking place from an unproven and unregulated therapy. The extended implications and actual lipid polymorphism and therapeutic manipulation of the self-organizing properties of lipid membranes "nanobiotechnology" behind what we term SAMMVs, were not considered or reviewed in the *Lancet* research. The research presented did not report that analysis of any individual phospholipids took place in order to discover the presence or amounts of biliary phospholipids or other membrane fusogenic and aggregation compounds and their effect on the formation and aggregation of micelles and vesicles.

Potassium carboxylates "soaps" appear to be one of many components of SAMMV formation. However, phospholipids appear to be "the" key ingredient in SAMMV formation, and the most important in terms of the mechanism of action and the therapeutic implications, but free AA, AA metabolites, other fatty acid metabolites, catecholamines and annexins are also expected to play a role in SAMMV membranes and formation. Preliminary testing indicates that SAMMVs will form without potassium in the 10 PM solution, and therefore without the expected formation of potassium carboxylates from dietary sources, but SAMMVs do not form in the intestines without sufficient amounts of phospholipids present for micelle and vesicle formation and subsequent aggregation. The addition of dietary PL causes a substantial increase in the volume of SAMMVs produced. The presence of potassium in the 10 PM solution is expected to increase the volume of SAMMVs produced by therapy. Potassium carboxylates are expected to be incorporated into the SAMMVs in the mixed micelles, vesicles and individually; they may also be included in the bilayer membranes of vesicles.

Research presented here has observed biliary phospholipid (PL) content of SAMMVs to be as high as ~2%, but is suspected to be higher at times. The amount of PL discovered in the samples suggests that SAMMVs are primarily monolayer and unilamellar vesicles with PL membranes and likely contain minimal micelles. If the SAMMVs were primarily aggregated mixed micelles they would be expected to have a higher percentage content of PL. The observed amounts of phospholipids in SAMMVs presented in this research appear reasonable, if SAMMVs are primarily constructed of unilamellar or monolayer phospholipid vesicles with the allowance of various amounts of mixed micelles and multilamellar vesicles.

In the literature bilayer and unilamellar vesicle are used interchangeably. A bilayer and a unilamellar vesicle are also interpreted as the same lipid structure in this research. Nanoveson™, LLC interprets a unilamellar and bilayer vesicle as the same lipid structure; i.e., two monolayers of phospholipids forming a single "bilayer" membrane of the vesicle with the outer ring of phospholipid hydrophilic heads facing outward and lipophilic/hydrophobic tails facing toward the center of the vesicle, and with the inner ring of hydrophilic heads facing toward the center of the vesicle and the lipophilic/hydrophobic tails facing away from the center. Unilamellar appears to be the most common term used for such vesicles in the literature. A monolayer vesicle is one with a single molecule/phospholipid thickness in the vesicle membrane and may also play an important role in SAMMV formation.

The expected monolayer, unilamellar/bilayer and multilamellar vesicles with PL membranes that undergo fusion and aggregation to produce SAMMVs also contain the free fatty acids, monoglycerides, diglycerides, glycerol, potassium carboxylates and other monomers, which may also be contained in their cores. The lipid content of SAMMVs, including free fatty acids, soaps, TAG and phospholipids, has been observed to be up to 25% in the research presented, but not including monoglycerides, diglycerides, glycerol and other products of digestion that are expected to make up a majority of the total weight and content of SAMMVs. Research presented is focused on the content of the SAMMV membranes and their biological implications.

The percentage of biliary phospholipid in SAMMVs become highly relevant when considered in light of the total volume of SAMMVs potentially produced by Nanoveson™ therapy, and the expected multiple of PL in SAMMVs expected to be in aqueous solution. A single Nanoveson™ treatment can produce as much as 100 to 200 grams of SAMMVs and is expected to be able to remove as much as 26 grams or more of stores of liver TAG that has been converted to phospholipids in SAMMVs and AQ, but smaller amounts of total liver TAG converted to PL will be more typical.

The *Lancet* research is relevant in distinguishing the difference in actual gallstones and what are termed here as SAMMVs, and naturally directed research to a more detailed analysis of SAMMVs for their potential biliary content, and the biochemical implications. The important consideration not addressed in the research reported in the *Lancet*, was that with repeated therapy, at least therapy comparable to Nanoveson™ therapy, the production of SAMMVs ceases, when the active dietary ingredients in and timing of the therapy remain the same. This is a very important point in considering the efficacy of Nanoveson™ therapy. Reported anecdotal health benefits of comparable therapy include significant improvements in lipid profiles and digestive disorders. TAG levels have dropped, LDL drops, and HDL increases. However, this occurs over an extended period, months or years, and after multiple therapies, which would certainly not have been evident or considered in this single case reported in the *Lancet*.

Thus prior to the invention a treatment for NAFLD and other fatty liver diseases and their comorbid diseases and a method to collect biomarkers for liver and comorbid disease diagnostic tests was not available. Nanoveson™ therapy represents a relatively straightforward treatment protocol that produces a cascade of highly complex and remarkable lipid polymorphism and nanobiotechnology reactions in the human body that serve to remove excess TAG stores from the liver. Nanoveson™ therapy also effectively acts as a form of lipid remodeling therapy. The result is the potential for a new and highly effective approach to treating NAFLD and other major chronic diseases related to liver function and biliary stasis. By targeting the lipid imbalances in the liver and at least partially or fully correcting those imbalances, symptoms are treated; and the cause of many diseases can potentially be reversed.

Dietary Lipid Abstention on Day of Nanoveson™ Therapy

Not consuming lipids (fat) on the day of Nanoveson™ therapy contributes to aspects of Nanoveson™ therapy by reducing the flow of bile and storing it for a more rapid release upon consumption of the Nanoveson™ 10 PM solution. The impact is two-fold: a) the lipid fasting acts to increase the amount of immediately available bile phospholipids for the formation of SAMMVs in the intestines when they are released by the 10 PM solution; and b) reduced bile release prior to the 10 PM dose is expected to create marginally increased biliary pressure, when this pressure occurs simultaneously with the demand for excessive amounts of bile, due to the amount of dietary lipids that the body must emulsify in the 10 PM solution, the resulting rate and pressure of bile flow acts to support exit from the biliary tract of bile, cellular debris, inspissated bile and inspissated bile plugs. It should be noted that the bile flow generated following consumption of the 10 PM solution is likely in a greater quantity and at a higher rate of flow than experienced historically by the patient. Nanoveson™ therapy does not require lipid fasting, by not fasting Nanoveson™ therapy may in fact require more stored TAG be remodeled into phospholipids, since the re-circulating phospholipids in the bile pool and in the bile stored in the gallbladder has already been utilized. However, lipid fasting may make Nanoveson™ therapy experience more pleasant for the patient and may reduce nausea. Clinical trials will help to establish the value of lipid fasting or total fasting the day of therapy and, if clinically appropriate, include it in Nanoveson™ therapy or make it optional.

Magnesium and CCK Release

The magnesium in the magnesium citrate taken in the 6 PM and the 8 PM doses initiate the release of limited amounts of the polypeptide hormone cholecystokinin (CCK) and therefore triggers the release of some bile, but magnesium is a weak stimulant to CCK release (9). The primary purpose of the high magnesium dose is to act as a cathartic to empty the intestines prior to the 10 PM solution. This occurs by pulling water into the bowels through osmosis to induce defecation. However, magnesium and citric acid are both important for cell metabolism and could therefore produce a secondary method of action that is beneficial if the patient is magnesium or citric acid deficient, and there is research that suggests blood serum magnesium deficiency (hypomagnesemia) is more common than currently recognized, and is linked to atherosclerosis, myocardial infarction, hypertension, cancer, kidney stones, premenstrual syndrome, and psychiatric disorders (10). It has been demonstrated that magnesium deficiency produces insulin resistance and increased thromboxane synthesis (12).

Recent research also indicates that hypomagnesemia is not only a symptom of fatty liver, but also increases oxidative stress and is likely a risk factor in the progression of fatty liver to steatohepatitis (11). A relationship exists between hypomeganesemia and fatty liver. Although not the primary method of action, large doses of oral magnesium used in Nanoveson™ therapy will likely lead to some magnesium absorption. Such absorption could have a positive secondary effect on outcomes if patients were magnesium deficient prior to beginning Nanoveson™ therapy.

The large dose of magnesium utilized in the therapy is expected to also play an important role in the rapid aggregation of vesicles into SAMMVs in the intestines. There appears to be more research available relative to the role of magnesium in the aggregation of phosphatidylserine vesicles than phosphatidylcholine (PC). Wilschut et al observed in their research on phosphatidylserine vesicles that in the presence of either $Mg^{2+}$ or $Ca^{2+}$ at above-threshold concentrations, both types of vesicles massively aggregate (137). This aggregation may partially be the result of the $Mg^{2+}$ or $Ca^{2+}$ impact on annexin proteins, which act as phospholipid binders that fuse vesicle membranes (139, 147). The research of Leventis et al on PC and PA vesicles noted that fluorometric measurements of lipid lateral segregation demonstrate that lateral redistribution of lipids in PA-PC vesicles begins at submillimolar concentrations of divalent cations and shows no abrupt change at the "threshold" divalent cation concentration, above which coalescence of vesicles is observed. They demonstrated that lipid segregation is at least strongly correlated with calcium-promoted coalescence of PA-PC vesicles and is essential to the magnesium-promoted interactions of vesicles of low PA contents (138).

10 PM Solution Triglyceride (TAG) Digestion

Carey et al. noted that gastrointestinal lipid digestion consists of three sequential steps: (a) the dispersion of bulk fat globules into finely divided emulsion particles, (b) the enzymatic hydrolysis of fatty acid esters at the emulsion-water interface, and (c) the desorption and dispersion of insoluble lipid products into an absorbable form (34). Those skilled in the art will recognize that the mechanism of action of Nanoveson™ therapy produces an intestinal environment that triggers far above normal physiological bile release and interrupts the normal digestion process in steps (b) and (c), and is focused on the surfactant lipids and other membrane forming compounds released from the gallbladder and liver and located in the membranes of micelles and vesicles. The bulk of SAMMV cores and therefore the bulk of SAMMVs are expected to be the products of emulsion and enzymatic hydrolysis produced in steps (a) and (b), including TAG, free fatty acids, monoglycerides, diglycerides and glycerol. Carey et al. also demonstrated how the emulsion droplets within the upper small intestines could be enveloped with a monolayer of biliary lipids mixed with the products of hydrolysis (34). The most important aspect of SAMMV formation and their contents from a therapy, biomarker and diagnostic perspective are related to the amount of and activity of the compounds found in the membranes of the micelles and vesicles that form the aggregates. Gastric, pancreatic and other digestive lipase activity and therefore hydrolysis activity will still be active at below normal pH during therapy, while pancreatic phospholipase A2 is expected to at least be partially suspended. Note that if fatty liver is present and sufficient phospholipids are released to form SAMMVs, a majority of the fat in the 10 PM solution is expected to be excreted in SAMMVs and not absorbed.

Intestinal pH

A low pH in the intestines appears to play an important role in the efficacy of Nanoveson™ therapy. The 6 PM and 8 PM doses of magnesium citrate and the acidity of the 10 PM Solution are the key. It is hypothesized that the magnesium citrate potentially drops the intestinal pH in three ways: 1) by forcing a large release of bicarbonate from the pancreas in response to the 6 PM and 8 PM doses, it reduces the available stores of bicarbonate for release with the 10 PM solution, thus allowing intestinal pH to drop with the digestion of the 10 PM solution; 2) the high doses of citric acid in the 6 PM and 8 PM doses and the PM solution are expected to drop intestinal pH on their own due to their acidity and rapid release into the intestines due to the lack of food solids; and 3) the osmotic action of the high magnesium citrate cathartic dose draws water into the intestines, thus reducing the pH significantly. There may be other factors that contribute to the expected drop in intestinal pH. The low intestinal pH is important because it is hypothesized to partially suspend PPLA2, thus allowing a majority of the biliary phospholipids and the fatty acids they contain to be removed in the SAMMVs; of key importance to Nanoveson™ therapy is that the fatty acid in the sn-2 position is not cleaved by the suppressed PPLA2 but is excreted. AA typically resides in the sn-2 position. Low intestinal pH created by the therapy is also expected to cause bile acids to precipitate out of vesicles, micelles and AQ and increase the formation and aggregation of vesicles. Some PPLA2 is expected to remain active during therapy and cleave small amounts of AA. Formulation adjustments will seek to suspend PPLA2 as effectively as possible to increase excretion of AA, its precursors and metabolites. Lower pH during therapy is also expected to play a role in vesicle aggregation. Kim D and Clapham D E at Mayo observed that lowering pH from 7.2 to 6.8 or 6.4 reversibly increased AA channel activity three or tenfold, respectively (153). AA and its metabolites are expected to play a role in activating Mg2+ or Ca2+ protein binding channels for membrane fusion during Nanoveson™ therapy, allowing fusion and aggregation of vesicles to produce SAMMVs in a lowered pH environment in the intestines.

10 PM Solution and CCK Release

When the 10 PM solution moves from the stomach as chyme into the duodenum the extremely high levels of fat content causes the release of large amounts of the polypeptide hormone cholecystokinin (CCK), which stimulates contraction of the gallbladder for the secretion of bile. CCK causes an increase in the production of hepatic bile, and therefore release of phospholipids (lecithin). The 24 HR lipid fast likely causes build up of CCK, with significant quantities released by the 10 PM Solution. The lack of solid food in the solution and the high content of lipids and high amount of citric acid accelerate the solution from the stomach into the duodenum. Malagelada et al observed that the amount of fatty acid consumed determined the length of the small intestines required for absorption (39).

There is a significant relationship between pancreatic and gallbladder responses to the amount of FA that is unabsorbed (39,40). The greater the surface area of the gut exposed to the stimulus of FA, the larger the amounts of CCK released, and the greater the response of the target organs of the pancreas and gallbladder (39,40), and in the case of Nanoveson™ with the exceptionally large amount of fat in the 10 PM solution, the liver. CCK release appears to be a function of the total load of dietary fat supplied to the duodenum rather than concentration. This suggest that the capacity of each cell releasing CCK is limited and that the total number of cells stimulated determine the amount of CCK released (39). The amount of fat in the 10 PM solution and its rate of speed through both the proximal and distal small intestines is expected to exceed the maximum potential fat absorption of the small intestines. The 10 PM Solution is expected to trigger close to the maximum possible release of CCK and therefore close to the maximum possible release of phospholipids into the bile.

Tricarboxylic Acid Cycle (aka Krebs Cycle)

Clinical trials will determine the effectiveness and value of oral malic acid for a period of days prior to Nanoveson™ therapy. The method of action contributed by malic acid is expected to be the necessity of malic acid as a substrate for the tricarboxylic acid cycle and the role it plays in the acetyl-CoA synthesis of lipids in the liver. Moekstra et al considered malate (the ionized from of malic acid) to be one of the key enzymes involved in endogenous cholesterol, fatty acid, TAG and phospholipid synthesis (lipogenesis) in the liver (42,43). Lipogenesis is the conversion of carbohydrate or protein to fat. The role of malate in the citrate transport required for fatty acid synthesis has been demonstrated, which leads to lipid accumulation in adipose tissue (44). It is likely that comparable therapy that included consumption of significant apple juice in days prior was merely efficiently converting the large amount of carbohydrates consumed to TAG stores in the liver for release as phospholipids for incorporation into SAMMVs. It is expected that patients deficient in malate could possibly benefit from intake of malate in preparation for Nanoveson™ therapy. At this time malic acid supplementation is not viewed as critical to the primary method of action of Nanoveson™ therapy. However, if clinical trials indicate it can provide improvement in clinical outcomes, it will be included in Nanoveson™ therapy.

TAG Polymorphism into Phospholipids: Phospholipid Synthesis

The amount of fat in the 10 PM Solution causes a significant release of CCK that in turn triggers the call for large amounts of bile, triggering the remodeling of liver TAG into bile phospholipids (lecithin) significantly above normal amounts, even above those required for a very fatty meal.

Phosphatidic acid is a precursor for the synthesis of a) phospholipids, utilized as bile lecithin, and b) for the production TAG in the liver. The liver is the primary location for synthesis of TAG, however TAG can also be synthesized in adipose tissue, lactating mammary glands, and intestinal mucosal cells (49). Fatty liver is effectively the accumulation of excess TAG in the liver. Nanoveson™ therapy is expected to require the liver to utilize some stores of phosphatidic acid (PA) for the creation of phospholipids demanded for the emulsification of the dietary fats consumed in Nanoveson™ therapy, making phosphatidic acid unavailable for the synthesis of TAG in the liver.

Nanoveson™ therapy provides for the reduction of clinically significant and excessive liver stores of TAG along three pathways; a) sequestering and eliminating the phospholipids in the existing bile pool, thus requiring their replacement by lipid remodeling from liver TAG; b) the utilization of the liver stores of free and membrane bound phosphatidic acid converted to diacylglycerol (DAG) for the production of bile phospholipids, thus denying the utilized diacylglycerol conversion and storage as TAG; and c) the most substantial method of TAG removal is expected to be the direct remodeling of stored liver TAG into phospholipids as bile lecithin (4).

Converting clinically significant amounts of stored liver TAG (fatty liver) into phospholipids for release through the hepatocyte membrane and into vesicles and micelles for aggregation and elimination in the SAMMVs and AQ, and encouraging increased PL release on an ongoing basis with improved enterohepatic circulation, is the primary method of action of Nanoveson™ for treating NAFLD and other comorbid diseases.

Choline is a key substrate for converting TAG into phospholipids. Choline deficiency is not common since it is readily available in the diet. However, the demand for choline during therapy due to the amount of TAG converted to PL during therapy may require the addition of choline as a component of Nanoveson™ therapy. The addition of choline in various amounts will insure required amounts of the substrate for therapy and to prevent deficiency from repeated therapy. Clinical trials will determine how much choline is being released by therapy, track potential deficiency, and determine if choline should be added to Nanoveson™ therapy.

Phospholipid Vesicles and Mixed Micelles

The primary mechanism for phospholipid secretion into bile is through the budding of bilayer phospholipid vesicles from the exoplasmic hemileaflet of the hepatocyte canalicular membrane (35). Once the hepatocyte in the liver releases phospholipids into the bile canalicular of the liver, the hepatic bile phospholipids are in three forms; vesicles and mixed micelles and phospholipid monomers. The balance between the two aggregated forms is not constant and represents an ongoing shifting equilibrium with the less stable vesicles becoming more stable micelles (129). The bile salts solubilize the phospholipid vesicles and they then aggregate into the mixed micelles.

Figure 4:
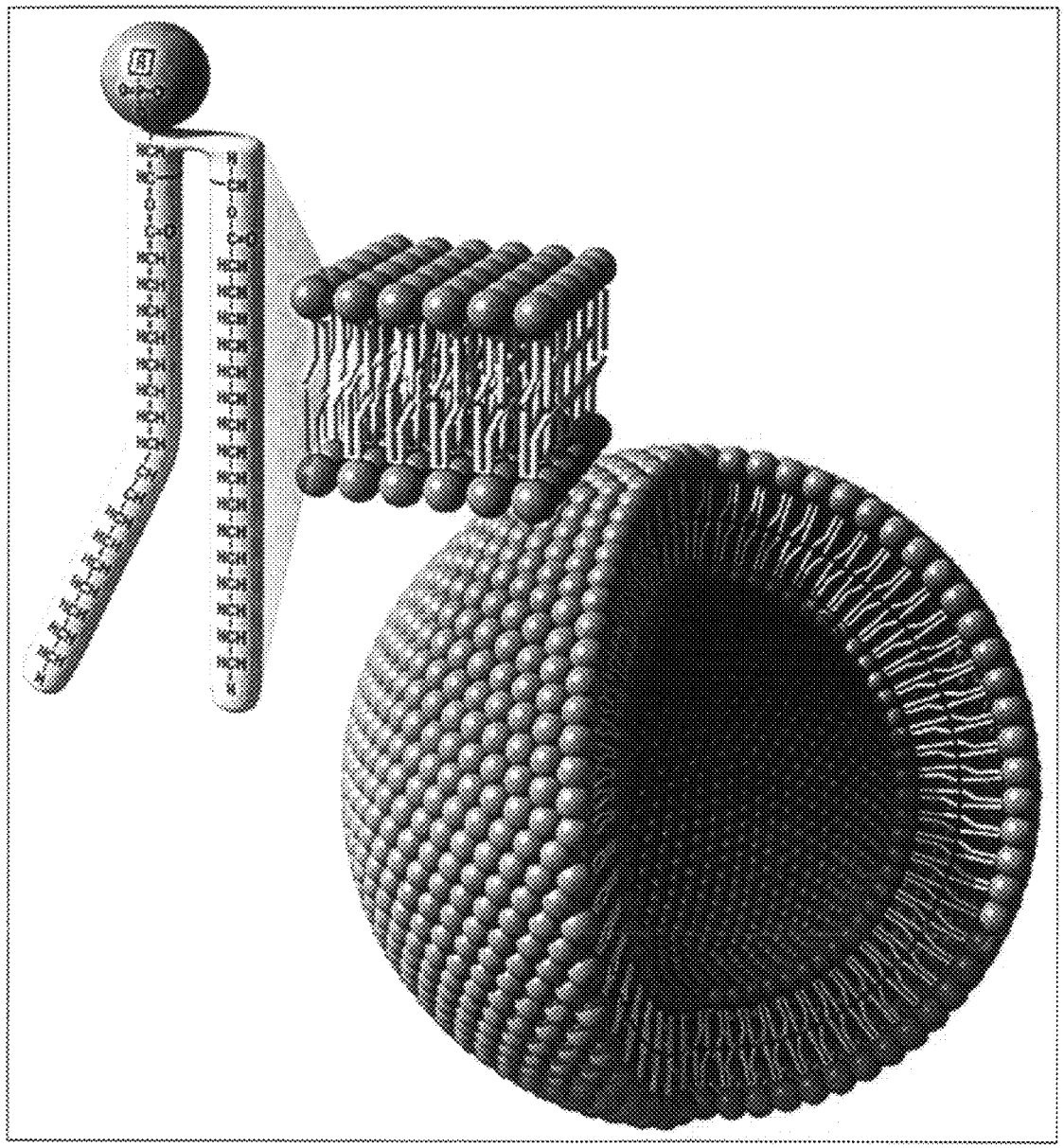
FIG. 4 demonstrates a bilayer phospholipid vesicle: the self-assembly of amphiphiles occurs when molecules with both hydrophilic and hydrophobic regions arrange themselves into a minimum energy configuration, such as a spherical phospholipid bilayer vesicle (128).
Figure 5:
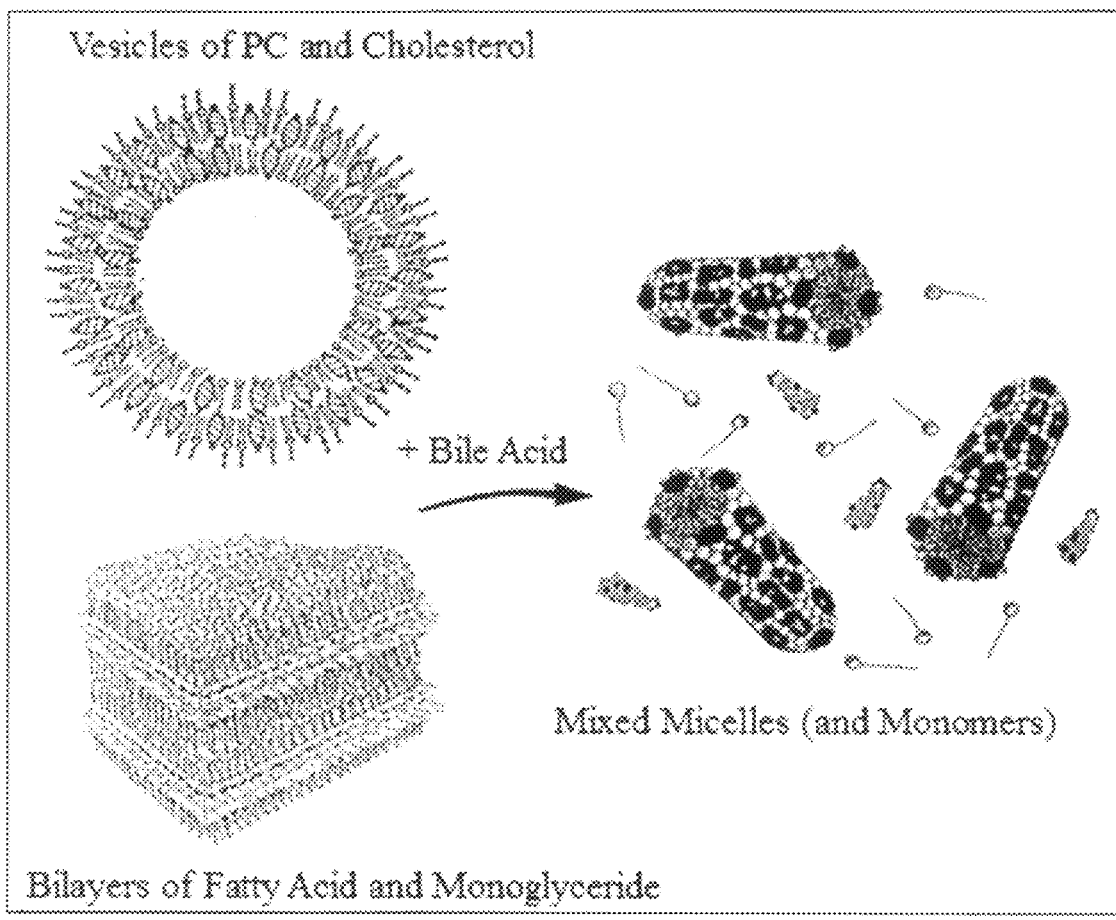
FIG. 5 shows conversion in the biliary canaliculus of bilayer vesicles containing phosphatidylcholine (PC) and cholesterol (upper left) to mixed micelles (right). Conversion in the intestinal lumen during fat digestion of bilayer lamellae-containing fatty acid and 2-monoglyceride (lower left) to mixed micelles (right). Mixed micelles are believed to be cylindrically shaped, with solubilized lipids arranged radially; bile acid molecule rests between polar heads of the lipids, with its hydrophobic side inward and its hydrophilic surface facing the aqueous phase. Fatty acid monomers are shown; in this illustration the concentrations of PC and cholesterol monomers are low (36,37)
Figure 6:
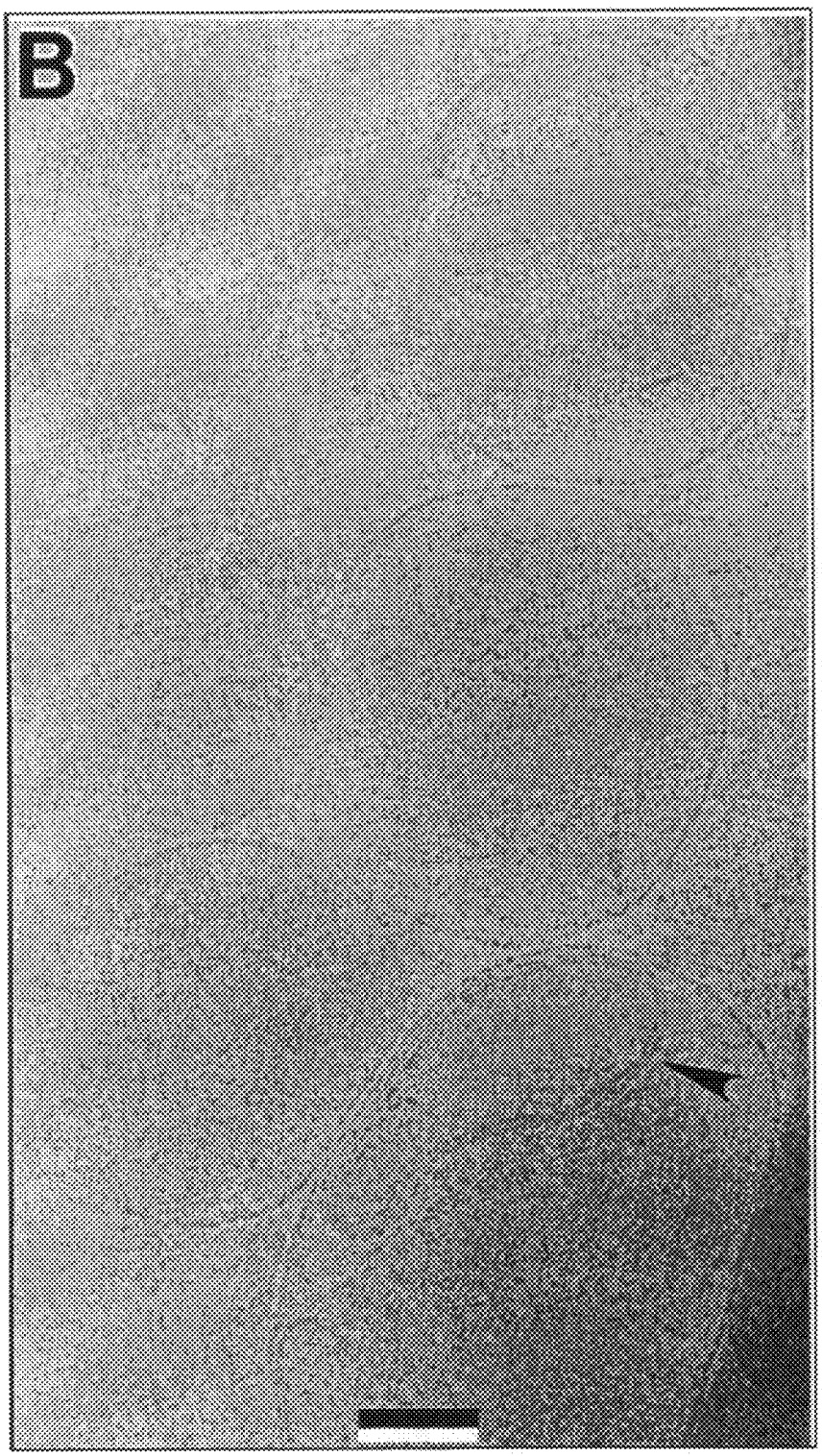
FIG. 6 comes from the model bile research of Donald L Gantz, et al and reveals large unilamellar/bilayer vesicles, shown here at 20 days. The vesicles had diameters ranging from 140 to 500 nm and may be enlarged because of squeezing/flattening in the vitreous ice layer. The multilamellar vesicle inside large unilamellar vesicles (arrowhead) should be noted. The mean bilayer thickness was 5.8 nm. Bar 5 100 nm. (135). Large unilamellar vesicles are expected to play a major role in SAMMV formation in the conditions created during Nanoveson™ therapy. This image may effectively demonstrate why Type I SAMMVs contain less than one percent phospholipids
Figure 7A:
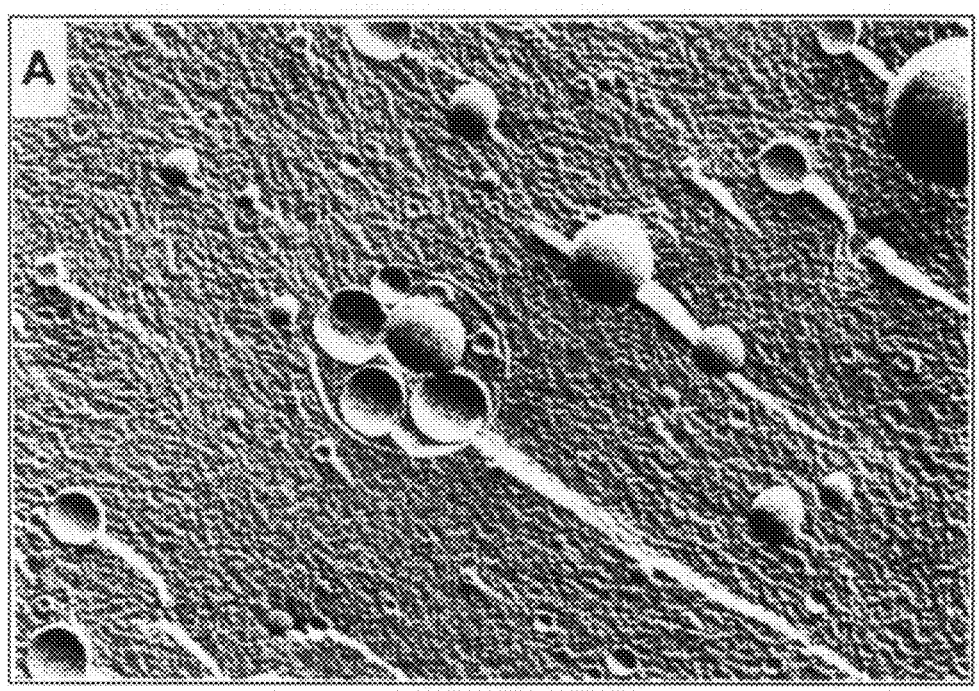
FIG. 7A shows aggregated vesicles in the center of the frame which may be similar to how the origins of SAMMV formation in the intestines would appear if captured by freeze fracture. In the case of monolayer vesicles that may form during Nanoveson™ therapy, the membranes contain phospholipids and the centers may contain AQ, free fatty acids and other monomers FIG. 7B show Lamellar vesicles produced in solution of 64 mM LPs (3:1 oleic acid: monoglyceride w/w) and 8 nM NaTDC at pH 6.9. A, A field of small dispersed vesicles; B, a large multilamellar vesicle appears in cross fracture. Both panels are the same magnification; bar=500 nm (130).
Figure 7B:
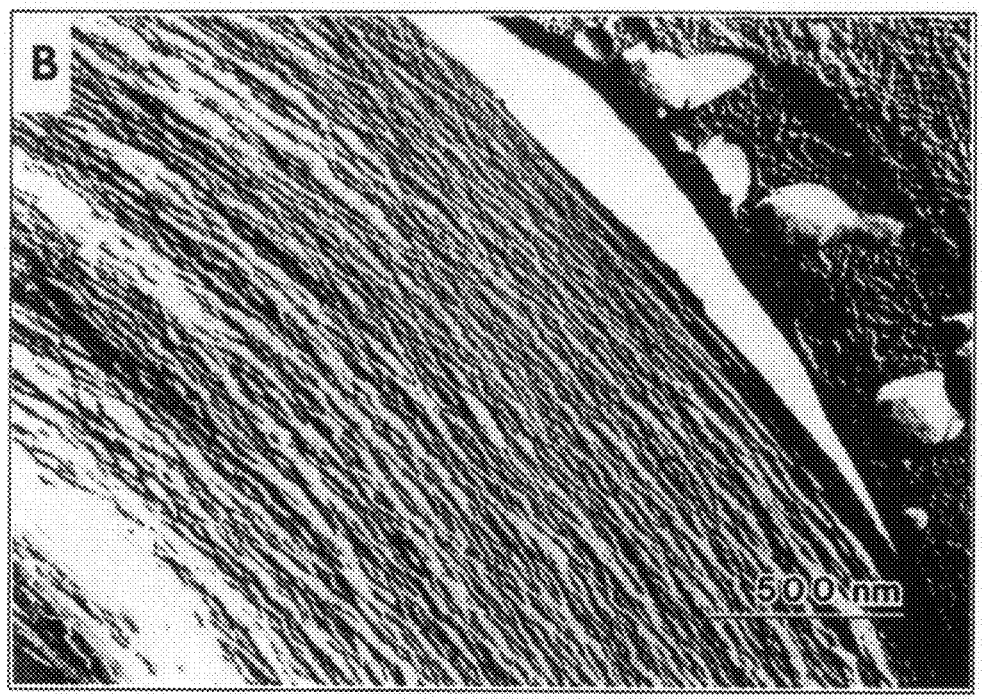

The budding in the biliary tract wall membrane of bilayer phospholipid vesicles and their release from the canalicular membrane into the intrahepatic bile duct provide for the supply of phospholipids (lecithin) in bile. FIG. 4 illustrates the structure of a unilamellar phospholipid vesicle. These phospholipid vesicles attract and incorporate additional bile salts in the biliary tract and transform to mixed micelles.

Critical Micelle Concentration (CMC)—Micellisation

Figure 3:
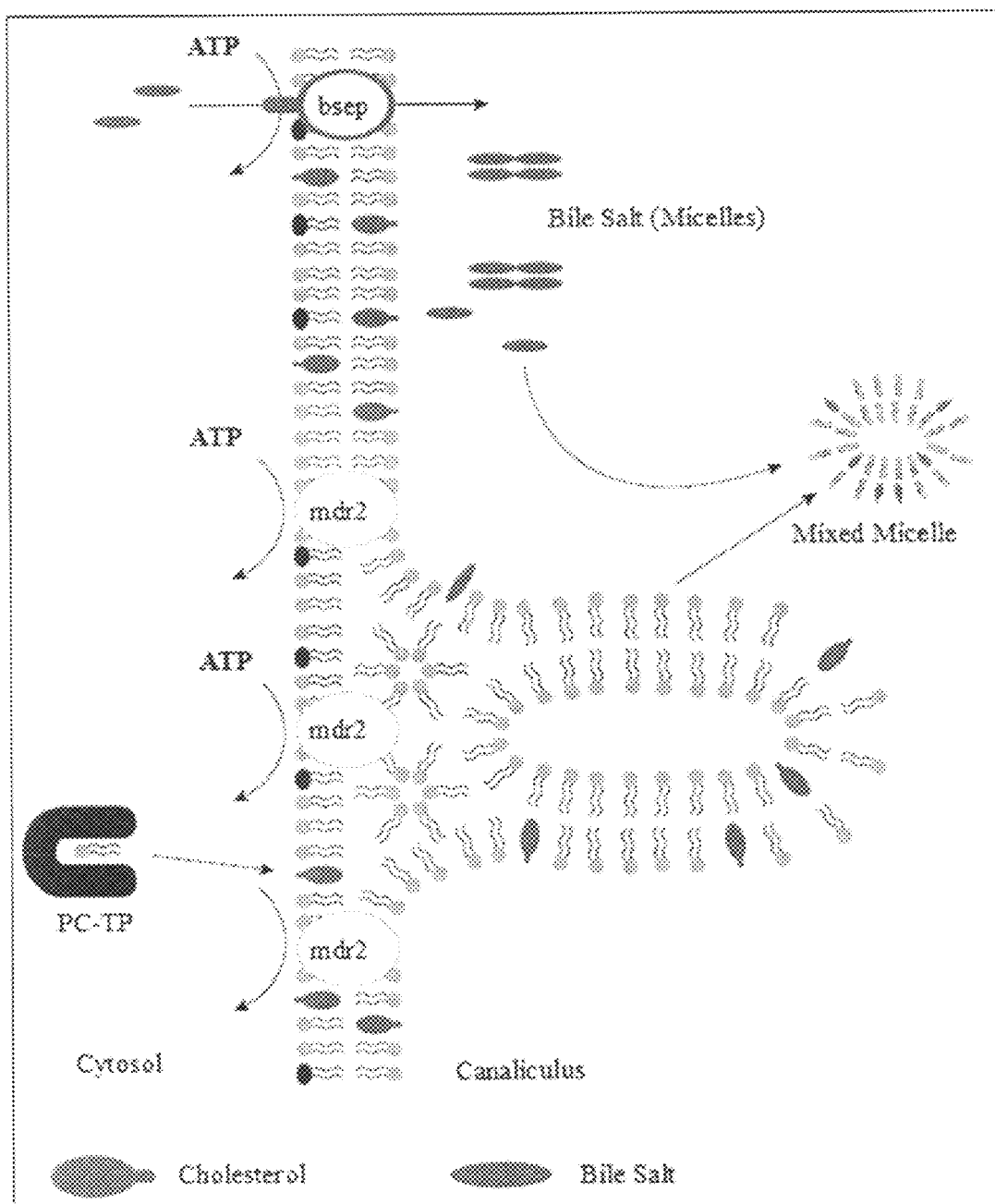
FIG. 3 shows events at the canalicular membrane. Bile acids are transported into the canalicular lumen by the adenosine triphosphate (ATP)-stimulated bile salt export pump (BSEP). Phosphatidylcholine (PC) molecules (shown with 2 parallel tails) are transported to the canalicular membrane by the PC transport protein (PC-TP) and across the canalicular membrane by the PC "flippase" (mdr2). When the PC molecules achieve a sufficient enrichment in the luminal face of the canalicular membrane, they bud out, forming bilayer vesicles that adsorb bile acid molecules. When the proportion of bile acid molecules is sufficiently high, mixed micelles are formed. Modified from Elferink et al (36,38).

The Critical Micelle Concentration (CMC) is the concentration at which an amphipathic molecule (e.g., a phospholipid or a bile acid) will form a micelle; a micelle is any water-soluble aggregate, spontaneously and reversibly, formed from amphiphile molecules (20). Micelles can also form in AQ in the intestines when there is enough phospholipids present, i.e. when the Critical Micelle Concentration is reached and exceeded. Bilayer vesicles released from the canalicular membrane during bile production are normally solubilized into smaller micelles in the biliary tract and gallbladder as bile salts are incorporated. Vesicles in the intestines are normally solubilized into micelles by bile salts. This occurs at the emulsion-water interface where digestion is occurring in the intestines. FIG. 3 demonstrates the formation of mixed micelles from solubilized vesicles of PC and cholesterol and bile acids in the canalicular membrane.

A key to Nanoveson™ and the production and aggregation of SAMMVs for excretion is that the phospholipids released in the bile, due to excessive levels of TAG in the liver during therapy, i.e. fatty liver, produces enough phospholipids in the intestines to greatly exceed the CMC at the emulsion-water interface (34) for the formation of micelles. There are other important factors at work in the formation of SAMMVs, such as the bile salt CMpH and a pH below the required level for phospholipase A2 (see below), which accelerates the expected formation of vesicles from micelles that aggregate as SAMMVs.

Thermodynamics partially explain the formation of micelles. Micelles form with a balance between the forces of entropy and enthalpy in solution. The concentration of the surfactant must be higher than the CMC of the surfactant for micelles to form. The temperature of the system must be greater than the critical micelle temperature. The hydrophobic character and lipophilicity of the surfactants, and electrostatic status of the surfactants, create an environment with the correct levels of energy for micelle assemblage (97,98,99, 100,101). Mixed micelle formation during Nanoveson™ therapy is a function of the concentration of the surfactants, i.e. phospholipids and bile salts, temperature, pH, and ionic strength of the surfactant.

The large amount of phospholipids released in the bile pushes the concentration of phospholipids in the small intestines at the emulsion-water interface beyond the CMC. This creates an environment where lipid micelles can form rapidly. The amount of dietary TAG and citric acid in the 10 PM solution creates a substantially above normal "high" threshold for the liver to produce enough phospholipids to attain the CMC in the AQ at the emulsion-water interface so micelles will form in the intestines. Another way of looking at the CMC is as the ratio the bile salts and phospholipids must reach as compared to the volume of the 10 PM solution and other digestion secretions for micelles to begin to form. The liver has likely never had to produce the amount of phospholipids required to reach the CMC in the intestines as is required during the intestinal conditions created during Nanoveson™ therapy by the 10 PM Solution.

Micelles can form in the biliary tract and in the intestines. Aspects of the micellisation activity that leads to the formation of the SAMMVs still require elucidation. The formation of SAMMVs and their predominant composition being lipid structures of the biliary and dietary lipids present during Nanoveson™ therapy is clear. However, there is another phase in the lipid formation and digestion process expected to be more critical to Nanoveson™ therapy efficacy.

Micellar Phase Boundary (MPB)—Micelles Morphing into Vesicles

Vesicles play the critical role in Nanoveson™ therapy, beyond budding out of the wall of the canalicular membrane as bilayer vesicles to provide for the secretion of phospholipids into bile as outlined above. In the biliary tract, some vesicles are unstable and change back into micelles with the incorporation of bile salts. Once secreted from the biliary tract into the duodenum, these biliary micelles aggregate in the small intestines and they reach a level of critical mass of micelles called the micellar phase boundary (MPB). When they reach the MPB, the aggregated micelles convert again into vesicles. The MPB, after the CMC, represents a second level of phospholipid concentration that is critical to Nanoveson™ therapy. It is expected that the MPB must be reached before any SAMMVs form with Nanoveson™ therapy.

It is not clear in the literature if a MPB must be reached for a micelle to change into a monolayer vesicle vs. a bilayer vesicle. In some respects a monolayer vesicle is a large micelle, since it has only a single phospholipid membrane with the hydrophilic head on the outside and the hydrophobic tail on the inside. It is suspected that formation of monolayer, unilamellar and multilamellar vesicles may be a result of Nanoveson™ therapy as bile salts precipitate out of micelles, vesicles and AQ and they are expected to be relevant to SAMMV formation.

In their research with model bile, Donald L. Gantz, et al observed that intermediate structures between micelles and unilamellar spherical/ellipsoidal vesicles were first seen at 23 min after supersaturation and represented the nucleation of primordial vesicles from supersaturated micelles. They noted that subtle changes in primordial vesicle structure such as enlarged micelle-like particles in primordial vesicle interiors, faceted edges, and short segments of bilayer at vesicle peripheries were observed over a time scale of minutes. It was suggested that vesicle formation in this model bile may be a gradual process involving the merging of micelles to form vesicle boundaries; and they noted that no evidence of aggregation/fusion of small unilamellar vesicles to form multilamellar vesicles was detected (135). Nanoveson™ therapy is hypothesized to create what could be viewed as a model bile environment in the intestines. As noted, the level of magnesium in the intestines is expected to have an impact on the formation and aggregation of vesicles through magnesium's binding properties that are yet to be fully elucidated. Carey et al observed that if bile salts in micelles were diluted the micelles would be transformed into unilamellar liposomes/vesicles (34). This appears to be a key mechanism of action in SAMMV formation.

Rigler et al reported that the bile salt micelle is essential for the solubilization and dispersion of lipolytic products (LP) in the intestine. Although the shape of simple bile salt micelles is thought to be spherical (130,33), the addition of LPs or phospholipids causes them to grow in diameter and become disc-like until the micellar phase boundary is reached. When the boundary is reached, spherical vesicles appear and coexist with the disc shaped micelles (130,34). In lecithin/bile salt systems, the boundary can occur at LP/BS ratio of 0.4 or greater (130,32). During Nanoveson™ therapy the LP/BS ratio is expected to be increasing rapidly as bile salts are immobilized by the drop in pH. In mixed lipid/bile salt phase boundary model system containing phospholipids, cholesterol, TAG hydrolyzates, and bile salts produce disc-like micelles with a mean diameter of 40 nm (130,34). Above this phase boundary, spherical lamellar vesicles are also produced (130).

The acidity of key ingredients in Nanoveson™ therapy are expected to drop the pH level and decrease the amount of bile salts available for incorporation into micelles (see Bile Salt CMCPH below). When there is depletion of the surfactant/detergent bile salts, there is a profound impact on the process and outcome of micelle aggregation and conversion to vesicles (100).

The dietary lipids taken in the 10 PM Solution trigger the release of the biliary bile salts and bile phospholipids to emulsify the dietary lipids, the lipids from these two sources, dietary and biliary, meet in the duodenum. Bile salts are precipitated out, the micelles aggregate with other micelles to form vesicles, the free fatty acids and carboxylates may bind to the aggregates, but are expected to be in the core of the vesicles; SAMMVs are formed.

Korgel et al observed that a number of groups (Rotenberg and Lichtenberg, 1990; Fromherz, 1983; Pansu, 1990; Lasic, 1987) have accepted a common view that vesicle formation by detergent depletion begins as the removal of detergent results in exposure of hydrophobic phospholipid tails at the edges of small, discoid micelles. These micelles aggregate to reduce edge energy until a critical micelle size or detergent-to-lipid ratio is reached where, upon further detergent removal, it becomes energetically more favorable to curl into a closed vesicle and eliminate edges at the expense of increased curvature elastic energy (131). The conditions during Nanoveson™ therapy, as bile acids precipitate out, with a low pH in the intestines, accelerate the formation of vesicles.

If the concentration of phospholipids and/or bile salts in the bile and AQ in the intestines is below the CMC, micelles do not form, no micelle aggregation occurs, and thus the MPB is not reached and a significant enough number of vesicles do not reform in the intestines to facilitate the digestion process, and to enable SAMMV aggregation during Nanoveson™ therapy, thus no SAMMVs would be formed. However, it may be possible for SAMMV formation with sufficient amounts of phospholipids to reach CMC, even if there are is not sufficient amounts of bile acids to form mixed micelles due to pH or other reasons.

Phospholipids and other surfactants self organize in AQ from aggregated micelles. Phospholipids can form tubes, spheres, flat bilayers, etc. The shapes and structures of the phospholipids in SAMMVs are not entirely known, but expected to primarily be unilamellar and multilamellar vesicles. The degree to which micelle and vesicle membranes include and mix phospholipids, potassium carboxylates, bile acids, cholesterol, fatty acids or other monomers is unknown. Phospholipids are expected to be in the membranes in addition to other material in the membrane and inside the vesicle. However, it is possible that predominantly potassium carboxylate micelles also bind with vesicles that are composed of phospholipids, bile and cholesterol.

SAMMVs may primarily form from aggregated small and large vesicles with membranes of phospholipids and other lypolytic products. These vesicles would contain free fatty acids, potassium carboxylates and other monomers and lypolytic products. After multiple Nanoveson™ therapies there appears to be levels at which not enough phospholipids are available to form the micelles and vesicles and therefore SAMMVs. Potassium carboxylates alone are not expected to form SAMMVs, a large enough ratio of phospholipids to carboxylates are required to be present.

The percentage of weight and volume of the vesicle phospholipids in the membrane compared to the whole of such a vesicle would depend upon the size of the vesicle. The research presented in this application suggests that it may be 1 to 2 percent, which accounts for the phospholipid content of SAMMVs, but the possible range is likely larger.

In considering the biochemistry behind Nanoveson™ therapy to this point, it is becoming clear that without sufficient levels of TAG in the liver to be remodeled or morphed into phospholipids in bile in the form of micelles and vesicles, the required environment would not exist for the formation of SAMMVs. However, it is suspected that other biliary compounds not yet fully elucidated also play a role in SAMMV formation in combination with phospholipids. Suspects are leukotreine E4 (LTE4) and CYP450 metabolites that may facilitate the binding of SAMMVs and increase the release of biliary AA. These compounds are expected to be incorporated into vesicle membranes along with phospholipids.

The amount of and ratio of AA in the bile PC and AA metabolites in bile are expected to play a role that is potentially important in the formation of unilamellar vesicles. The literature suggests that free AA and its metabolites play a role in vesicle fusion (139-143). Creutz reviewed 23 compounds for their contribution to large vesicle formation and found AA to be the greatest in fusogenic activity (139). Bloch-Shilderman et al suggest that AA metabolites may induce exocytotic release and fusogenic behavior (140). Abu-Raya concluded that the possibility that eicosanoids directly regulate the fusion process, independent of calcium, merits careful consideration (141). Work with model membranes by Mayorga et al suggests that fusogenic lipids may play a role in membrane fusion (142). McIntosh et al research on membrane fusion promoters and inhibitors concluded that AA promotes fusion (143).

Halpern et al noted in their study of model bile that under conditions of bile salt depletion phospholipid rich vesicle formation would be expected due to the comparative inability of such solutions to form micelles (134). During Nanoveson™ therapy, due to a low pH, bile salts are expected to precipitate out of AQ, micelles and vesicles in the intestines causing rapid formation of unilamellar/monolayer vesicles and aggregation of micelles and vesicles. During Nanoveson™ therapy the biliary phospholipids form vesicles when they meet the PM Solution dietary fat in the therapy, resulting in vesicles aggregating on an accelerated basis to form SAMMVs. A majority of the vesicles likely form within the first few hours following the 10 PM solution dose, and aggregate rapidly in the intestines in the conditions created by Nanoveson™ Therapy.

The role of phospholipid rich vesicles formed in the intestines in the production of SAMMVs is critical, however, a very small amount of SAMMVs are not expected to include vesicles formed and aggregated in the intestines. These are expected to be SAMMVs that originate as small IBPs in the biliary tract, which consist of aggregated biliary tract vesicles. There may be these Type III SAMMVs excreted during therapy where in the intestines the level of phospholipids does not reach the CMC and MPB, so they include no intestinal formed vesicles.

Catecholamines, Annexins, AA and AA Metabolite Impact on Vesicle Fusion and Aggregation: Implications for SAMMV Formation The research of Carl E. Creutz considered the fusogenic activity of chromaffin granules (containing catecholamines/epinephrine), synexin (a.k.a. annexin VII) a Ca2+ binding protein, and cis-unsaturated fatty acid, specifically AA, on the induction of vesicle fusion and vesicle aggregation, potentially provides relevant insight into certain aspects of the biochemistry behind SAMMV formation (139) and potentially the efficacy of the therapy.

The implications of Creutz's research also points to some of the diagnostic potential for the therapy. The presence of catecholamines in hepatic stellate cells and in bile have been demonstrated by the research of Shibata et al (151) and Sancho-Bru et al (150). Shibata et al (151) demonstrated the presence of catecholamines in gastric juice and bile juice during surgery. Catecholamines have the recognized ability to promote free fatty acid release from adipose tissue and promote TAG accumulation in the liver (155,156). Nanoveson™ therapy is hypothesized to generate release of some catecholamines from hepatic cells, however, the catecholamines released in the bile during therapy come from existing stores in hepatic cells and/or from new adrenal gland release.

The research of Meers P et al later clarified that synexin (annexin VII) plays a role in aggregation but not fusion of liposomes/vesicles, demonstrating that the presence of annexin (AX) can increase the aggregation rate up to 100 fold (147). Such annexin properties for accelerated vesicle aggregation is hypothesized to play a role in SAMMV formation. The amount of annexins present in bile during therapy and their binding properties is unknown. The research of Renaud G et al concluded that, in rats, hepatocytic lysosomes empty most of their contents into bile every week or two, apparently by exocytosis (149). The conditions created by Nanoveson™ therapy, with a demand for bile likely exceeding historic demand and exceeding the amount of bile available from the gallbladder, therefore requiring additional significant bile production from the liver, may accelerate the emptying of hepatocytic lysosome content into bile, including annexins and catecholamines.

Of particular interest in Creutz's work is that his experiments suggest that AA and its metabolites play an important role in vesicle membrane fusion (139). Prostaglandin and other AA metabolites are known to have high lipophilicity, be hydrophobic and have high partition coefficients. Of the 23 compounds he tested, AA was found to demonstrate the greatest fusogenic properties for the formation of vesicles. Although Creutz research considered AA metabolites in the form of prostaglandins, our research suggests that other AA metabolites, such as LTE4 and P450 derived AA metabolites, may also play a role in vesicle fusion and therefore be active compounds present during therapy and SAMMV formation. Observation of Creutz's research expected to be pertinent to our research include the following: 1) the effective fusogen appeared to be the unesterfied fatty acid incorporated into the membrane; 2) AA was the most effective fusogen at a minimum concentration of 2 ug/ml (6.6 uM); 3) AA metabolites were suggested to manifest the same fusogenic properties as AA; 4) doubling the chromaffin concentration doubled the threshold concentration of AA needed for fusion; 5) the fusion could be seen in the presence and absence of annexin VII; 6) raising the pH of the suspension from 6.0 to 7.2 strongly inhibited the rate of fusion; 7) higher levels of the less effective acids were able to cause the same degree of fusion as lower levels of the most effective (139).

The presence of AA bound to the phospholipid PC and other PL and action of PPLA2 during therapy is expected to make small amounts of free AA available during therapy that will play a role in the fusion of vesicles. However, it is expected that the amount of available AA metabolites during therapy, yet to be established, will be greater that the amount of free AA, which could play a relevant and potentially more important role in vesicle fusion. With the amount of free fatty acids available during therapy, there are obviously a significant amount of vesicle fusogens available, therefore the aggregation characteristics of annexins discovered by Creutz, and expanded by Meers et al, may be the more relevant finding related to SAMMV formation. If the amount of AA metabolites are found to exceed the amounts of free fatty acid fusogens produced during therapy, it will be a very relevant contribution to the understanding SAMMV aggregation from Creutz's research.

Catecholamines are expected to play a role in vesicle fusion in conjunction with the PL in bile, and are expected to be present in SAMMVs. The research of Sancho-Bru et al has identified the participation of catecholamines in the pathogenesis of portal hypertension and liver fibrosis through adrenoceptors in human stellate cells (150). The amount of and type of catecholamines released during therapy and captured in SAMMVs are therefore expected to provide biomarkers for diagnostic tests for portal hypertension, fibrosis, NAFLD, NASH and ALD. However, PL is suspected to be the key compound in vesicle membranes in the vesicles in SAMMVs. The makeup of the vesicle membranes and their catecholamine content has yet to be quantified. It is possible that certain amounts of annexin and catecholamine are required ingredients for SAMMV formation.

The work of Creutz may help to explain how specific concentrations of lipid compounds are required to be present during therapy for vesicles to form and aggregate. The level of PL is expected to be the key, but how AA, AA Metabolites and available FFA interacts with annexin, catecholamines and other compounds released in bile during therapy and interact with PL in fusion and aggregation require additional research to completely understand the role of each, and the levels at which they contribute to SAMMV formation.

Capdevila J H et al proposed a functional role for microsomal P450 in the control of cell membrane microenvironment structure and, hence its functional properties. They noted that it has been established that prostaglandins, leukotrienes, and other polar eicosanoids mediate their actions through specific cell surface G-protein-coupled receptors and proposed that less polar EETs and HETEs may exert their biologic effects by incorporation/esterfication into cellular phospholipids (154). Cytochrome P450 plays a significant role in the production of bile acids and is present and active in the liver. This P450 research may provide some insight into how AA metabolites from the P450 pathway play a role in the membranes of vesicles that aggregate to form SAMMVs in the intestines. This potential requires additional research to be fully understood and explained. AA metabolites from the Cytochrome P450 pathway, if present in SAMMVs, will potentially provide biomarkers for liver diseases and other AA related diseases. Cytochrome P450 is also active in a majority of drug metabolism. If SAMMVs include Cytochrome P450 metabolites, the proposed therapy may provide a new standardized mechanism of biomarkers and diagnostic tests for drug metabolism testing.

It is anticipated that the amount and ratios of catecholamines, annexin, AA, AA metabolites, and other FA metabolites in SAMMVs will affect the amount of PL incorporated into SAMMV membranes. The ratios of other ingredients to the expected content of PL in SAMMVs will be determined by clinical trials and established for biomarker and diagnostic purposes. FFA, CAT, AX, AAM and other FA metabolites, if present in sufficient amounts, may allow the formation of SAMMVs during therapy when liver TAG deposits have been significantly reduced and minimal or even negligible amounts of PLs are available for membrane fusion and SAMMV formation.

There is limited calcium in Nanoveson™ therapy ingredients. The lack of sufficient quantities of calcium during Nanoveson™ therapy, which plays a role in activating PPLA2 (173), may also act to decrease the phospholipid lipase activity and the breakdown of phospholipids during therapy; and thus increase the fusion of vesicles and the morphing of micelles into vesicles. The calcium/phospholipid ratio is expected to be lower during Nanoveson™ therapy than during normal digestion due to the large secretion of phospholipid from remodeled liver TAG and limited amounts of calcium in Nanoveson™ therapy ingredients as compared to a normal diet. Remodeling occurs when liver stores of triglyceride consisting of three fatty acids attached to a glycerol molecule backbone undergo transformation into new molecular structures in the form of a phospholipid consisting of two fatty acids attached to a glycerol backbone (a diglyceride), attached to phosphate and choline, and when liver stores of phosphatidic acid, a small phospholipid, is transformed into phospholipids required for bile with the incorporation of choline.

Growing Preformed Vesicles and De Novo Vesicles

The research of Chen and Szostak (136) in the area of fatty acid micelle and vesicle aggregation may be relevant to SAMMV formation during Nanoveson™ therapy from free fatty acids, potassium carboxylate soaps and biliary phospholipids. During therapy it is expected that various amounts of biliary vesicles bypass the gallbladder and are carried directly to the intestines, without being solubilized in micelles and free fatty acids. In the intestines these "preformed" vesicles are expected to grow from the aggregation of additional micelles formed during digestion, as long as the amount of PL is above the CMC for PL in the intestines.

It should be noted that preformed biliary vesicles that enter an intestinal environment that is below CMC will begin to be solubilized. They may still aggregate into SAMMVs in such an environment, especially as the pH drops rapidly and bile salts precipitate out. Such intestinally aggregated vesicles when PL is below CMC will have a different compound makeup than other SAMMVs.

It is also expected that new "de novo" vesicles form from aggregates of micelles that exceed the MPB when the amount of phospholipids in the intestines exceed CMC and MPB. The growing vesicles of biliary origin and the de novo vesicles formed in the intestines are expected to aggregate into SAMMVs. The amount of preformed vs. de novo vesicles may impact the PL content of SAMMVs and therefore the type of SAMMVs formed.

Chen and Szostak observed that the aggregation of micelles appears to be an immediate consequence of the pH drop (136). As reviewed, the therapy is expected to force a rapid pH drop in the intestines, and this research supports the role of pH drop in aggregation.

TAG in SAMMVs—Diagnostic Implications

The following TAG discussion is highly tentative and requires confirmation. TAG found in SAMMVs <1% in the examples presented, most likely comes from the large quantities of TAG in the 10 PM Solution that aggregate with products of hydrolysis in the SAMMVs. However, there may be other forces at work that are relevant and introduced here. TAG is not present in bile and is not present in the biliary tract. TAG is also not expected to be present in micelles. Micelles only contain phospholipids, bile salts and cholesterol. Vesicles formed in the intestines, on the other hand, can incorporate and contain limited amounts of TAG in addition to phospholipids and bile salts.

Boyle-Roden and Walzem reported that TAG has been documented in PL surfaces of vesicles and emulsions by the measurement of 13 C carbonyl-enriched TAG (88,91-96). Measurements of the amount of TAG in the surface of PL vesicles generally agree with the emulsion data (88,89,90), but neither system contains protein (88).

It is expected that TAG can be incorporated into SAMMVs as they form in the intestines that include vesicles formed in the intestines when the CMC of phospholipids in the intestines is high enough to form micelles that aggregate to exceed the MPB and form vesicles. SAMMVs that form in the intestines, from new vesicles that form in the intestines, Type I SAMMVs, should theoretically have more TAG than Type III SAMMVs, with higher levels of biliary tract content in the form of IB and biliary sludge that have significant amounts of fusogenic compounds that increase the formation of SAMMVs.

It should be noted that these TAG concepts of inclusion and exclusion in SAMMVs, are tenuous at this time at best. TAG in SAMMVs likely comes from the 10 PM Solution. However, Type III SAMMVs that are expected to contain more IB and do not contain TAG, or extremely low levels of TAG, are one aspect of Nanoveson™ therapy. If they do not contain TAG, when it was present in relatively large quantities in the dietary lipids, the implication is that the amount of phospholipids did not reach CMC and/or MPB in the intestines, so new vesicles did not form in the intestines; and therefore the SAMMVs did not form from aggregating micelles exceeding the MPB in the intestines, but from preformed vesicles from the biliary tract, which may be found in large quantities in bile and biliary sludge.

It is important to note that aggregating vesicles could form SAMMVs in the intestines that were preformed vesicles in the biliary tract that were not solubilized in the intestines. The intestinal AQ could potentially be below the phospholipid CMC and/or MPB, while vesicles from the biliary tract are not solubilized and remain intact and aggregate in the intestines before being solubilized in the intestine due to the low pH. However, such preformed vesicles may in fact still incorporate dietary TAG in the intestines. Additional research is required to determine the diagnostic relevance or lack thereof regarding the amount of TAG found in SAMMVs.

Biomolecules in SAMMVs

In addition to phospholipids, AA and AA metabolites many other biomolecules are expected to be present in micelle and vesicle membranes and cores that have aggregated into SAMMVs. These biomolecules will have both therapeutic, biomarker and diagnostic implications for multiple diseases. These will include methyl esters, fatty acids, fatty acid metabolites and environmental pollutants. SAMMVs are also expected to aggregate drug molecules being metabolized by the liver and therefore have potential to be used as biomarkers for testing various stages of drug metabolism.

Bile Salt Critical Micelle ph (CMpH)

Bile salts and phospholipids are amphipathic molecules that act as surfactants/detergents. They work together to emulsify lipids for digestion. If bile salt activity is reduced, i.e. they precipitate out of lipid bilayers and vesicles due to a low pH, and their content in micelles and vesicles is reduced, it would be expected to increase the speed of aggregation and the number and size of phospholipid vesicles aggregating into SAMMVs.

Significant amounts of bile acids are likely synthesized into bile salts in the liver due to Nanoveson™ therapy for the purpose of solubilizing the dietary lipids. The high volume of bile salts will correlate to a high volume of phospholipid output into the bile canaliculus. Bile salts are surfactants/detergents that act to break down and dissolve lipids during digestion. However, during Nanoveson™ therapy the high phospholipid levels that exceed the CMC occurs in a low pH environment due to the osmosis and other effects of the active ingredients of Nanoveson™ therapy and the 6 PM and 8 PM doses. In order to solubilize biliary and dietary lipids, bile salts are required to be soluble to be present in micellar concentration (25).

Hofman and Mysels have demonstrated what they call the critical micelle concentration pH level (CMpH), below this level bile salts are not soluble. Below the pH of 6.0 bile salts will be slow to form simple bile salt micelles and mixed micelles with lipids. In these pathological conditions below the CMpH bile acids precipitate from the AQ in the form of protonated acid; this precludes them from joining micelles to solubilize the biliary and dietary lipids (25). This prevents the biliary phospholipids from solubilization by bile salts, and is expected to therefore further encourage the phospholipid aggregation into SAMMVs, if they are present in concentration amounts above the CMC.

The pH level in the duodenum during Nanoveson™ therapy is unknown at this point, but the high citric acid content and evidence provided from limited SAMMV sample analysis suggest that the pH is below the Bile Acid CMPH because PPLA2 appears to have also been suspended (see below). PPLA2 requires pH above 5.8, just below the bile salt CMpH.

If Nanoveson™ therapy does in fact create an environment in the intestines that drops the pH below the CMpH for bile salt micelles, when the phospholipid content is above the phospholipid CMC, it would, theoretically, be expected to accelerate the aggregation of micelles into unilamellar vesicles and cause SAMMVs to aggregate rapidly. It should be noted that pH levels during Nanoveson™ therapy need to be confirmed and this CMPH information is presented with limited research and subject to error, i.e., there could be other forces at work. There is not an exact rate of aggregation currently known and the rate of aggregation will vary due to multiple factors, including pH, phospholipid concentration above CMC and MPB, etc.

Pancreatic Phospholipase A2 (PPLA2)

Very limited free AA has been observed in SAMMVs and none in AQ in laboratory analysis. Lab analysis indicates the AA is still attached to the phospholipids, strongly suggesting that AA is not cleaved from the phospholipids by PPLA2 during Nanoveson™ therapy. Other forces at work may explain this, but they have yet to be discovered.

During Nanoveson™ therapy it is expected that PPLA2 appears to have been suspended by the decrease in the pH level of the small intestines from the high level of citric acid in both the magnesium citrate in the 6 PM and 8 PM doses and the accelerated movement into the intestines of the citric acid in the 10 PM solution. The suspension of PPLA2 prevents the breakdown and emulsification of the lipids for more effective absorption.

The unique combination of dietary lipids and citric acids in the 10 PM solution, in addition to the 6 PM and 8 PM doses, and their rapid release into the duodenum, provide an environment where pH drops below an intraluminal pH 5.8 level, at which point phospholipase A2 is inhibited (16). Multiple Nanoveson™ treatment samples were sent for laboratory testing, there has been only limited identification of free AA in one set of samples that were exposed to elevated temperatures, which would have activated lipase activity. This would be the expected outcome if it was not being cleaved from the phospholipids. AA appears to remain attached to the phospholipids, indicating PPLA2 was suspended, most likely due to a pH below 5.8.

SAMMV Formation—Sequestering and Aggregation of Micelles & Vesicles

A concentration of phospholipid micelles, vesicles, free fatty acids and potassium carboxylate micelles in the small intestines above the CMC hits a trigger point, at which they are expected to rapidly from unilamellar vesicles and aggregate to form SAMMVs. The SAMMVs will range in size from 1 mm to 2 cm and possibly larger. It is expected that SAMMVs will nucleate in the duodenum and continue to aggregate primarily in the jejunum and ileum, and it is possible that some will also form in the large intestines. They are a malleable putty like substance made up of both the dietary 10 PM solution lipase products and the biliary excretions. The phospholipids, located in the vesicle membranes and acting as the sequestering agent for the SAMMVs, appear to make up ~1% to 2% of the total SAMMVs, based on the research conducted to date.

The SAMMVs and AQ they are in make a rapid transit through the small intestines due to the osmosis of the magnesium citrate and prior intestinal evacuation. It is currently unknown if the intestinal osmosis produced by the magnesium citrate or the expected increased speed of digestive tract transit increases absorption resistance in some way, and thereby decreases the rate of absorption of the dietary Nanoveson™ therapy lipids in the small intestines, but decreased lipase activity would be expected to decrease dietary lipid absorption.

Research suggests that fatty acid absorption does not occur directly from lipids in the form of fatty acid and bile acid in the mixed micelles, but only from the pool of fatty acids in the AQ, i.e., not from micelle bound lipids (15). It should be noted that this is an older citation and the position taken by the authors that digestion of phospholipids occur by passive diffusion only in the small intestines has been contradicted, but no contradiction has been discovered in the literature to the absorption from AQ as opposed to the micelles. With the addition of every CH2 group to the chain of a fatty acid, the probability of solubility and therefore intestinal absorption declines (15). Contradiction to this observation has not been located in the literature by the author.

The longer the chain of the fatty acids the less soluble it is and therefore the less likely to be absorbed in the intestines, and the more likely it is to aggregate into a SAMMV; another way of explaining it is that the longer the chain the greater the lipophilicity and the greater the odds that the lipid will be attracted to lipids aggregating in the SAMMVs. The increased water in the intestines from osmosis increases the hydrophobic environment and their tendency to aggregate. As the micelles form and aggregate into the SAMMVs, the lipids are no longer available for absorption. Since phospholipase A2 has been suspended due to the low pH produced by Nanoveson™ therapy, biliary phospholipids are not being broken down for absorption, but are instead being aggregated intact into the SAMMVs.

Nanoveson™ therapy produces a high level of oleic acid in the intestines. Research indicates that oleic acid enhances the binding of all bile acids (13). The high level of oleic acid during Nanoveson™ therapy likely has an impact on the rapid creation of the SAMMVs in the intestines on any bile acids that survive the low pH environment. The magnesium citrate encourages the rapid transit through the intestines of the Nanoveson™ therapy lipids and biliary lipids released, thus preventing breakdown and absorption of the SAMMVs once formed, however, failure to follow up with the AM Nanoveson™ LMC dose(s), could allow them to be reabsorbed.

It is estimated that the human liver can secret very large amounts of bile acids, up to 36 grams per day (17); but Nanoveson™ therapy prevents these bile acids from fully doing their job of digesting the dietary lipids. The fact that these large amounts of bile acids are at least partially disabled by a low pH during Nanoveson™ therapy is expected to be critical to the formation of SAMMVs. In addition, as reviewed, suspension of PPLA2 prevents the biliary phospholipids produced by Nanoveson™ therapy from fully participating in digestion.

SAMMVs are aggregates of biliary and dietary lipids containing mixed micelles, vesicles, free fatty acids and TAG. Simple bile acid micellisation is expected to be impaired; trials, additional analysis, and more research will clarify the details of the formation of SAMMVs and the content of vesicles, fatty acids, mixed micelles and bile salts. Other components, such as LTE4 and possibly other AA metabolites, are also expected to aid in SAMMV formation.

To summarize SAMMV formation, the ideal conditions required for SAMMV formation in the intestines appear to be as follows: (Phospholipids>Critical Micelle Concentration)+(pH<Bile Salt CMPH)+(pH<Pancreatic Phospholipase A2 of 5.8)+(Micelle Concentration>Micellar Phase Boundary)+(Fee Fatty Acids)+(Arachidonic Acid)+(Arachidonic Acid Metabolites)+(Annexin Phospholipid Binders)+(Catecholamines)+(Potassium Carboxylates)=SAMMVs; or abbreviated:
(PL>CMC)+(pH<BS CMpH)+(pH<PPLA2)+(MIC>MPB)+(FFA)+(AA)+(MM)+(AX)+(CAT)+(POC)=SAMMVs.

Types of SAMMVs and Formation

Limited testing suggests there are what could be considered various types of SAMMVs that can be produced from Nanoveson™ therapy, primarily defined by their PL content. Other content may be used to categorize SAMMVs in the future. The Type of SAMMV formed by therapy will be dependent upon the status of the patients biliary tract, levels of TAG stores in the liver, the status of liver disease and the patients response to a particular Nanoveson™ therapy session. The SAMMV types proposed here are intended to be preliminary. Final types or other rating scale may be established with additional research from the scientific community. Types formed will also be dependent upon the lipid and cathartic content amounts and compliance and timing of Nanoveson™ therapy. The type of SAMMVs is largely determined by the amount of phospholipid available for incorporation into the SAMMVs, where they form in the intestinal tract and when they form. The degree of solubilization followed by reorganization and aggregation of biliary micelles and vesicles that occurs in the biliary tract and intestines during therapy will affect type formation. It is important to note that it is possible that one therapy session can include the excretion of multiple types of SAMMVs. A blended or homogenized sample of multiple SAMMVs from one therapy will reflect the average make up of the individual SAMMVs excreted by a given therapy treatment.

Type I SAMMVs

Type I SAMMVs will be the most common form of SAMMV formed from a patient with simple fatty liver, or sufficient TAG deposits in the liver that may be less than the required to diagnose fatty liver. Type I SAMMVs are expected to form exclusively in the intestines and have less than 1% total SAMMV weight in PL incorporated in the membranes. Most of the phospholipids released into the intestines are expected to primarily be in the form of individual PL monomers. Mixed micelles and vesicles from the biliary tract are expected to be partially solubilized by bile salts in the intestines, before bile salts precipitate out of the vesicles and micelles due to the low pH environment created from the therapy. The content of biliary sourced phospholipids in the intestines remain above the CMC of phospholipids and new phospholipid micelles form. These micelles will also include digestive material from the dietary lipids, including potassium carboxylates. The micelles then begin to aggregate and exceed the MPB and form vesicles, expected to primarily be monolayer and bilayer vesicles. Some vesicles from the biliary tract may not be solubilized, but begin to incorporate digestive content and rapidly grow in volume. Due to the conditions in the intestines, it is hypothesized that small unilamellar vesicles (SUV) and large unilamellar vesicles (LUV) form rapidly and aggregate. Included in these aggregates are micelles and monomers. Type I SAMMVs will not have any inspissated bile plugs from the biliary tract, however, it may include some inspissated bile that is solubilized to a degree in the intestines and then reincorporates additional phospholipids and other digestive material and aggregates into SAMMVs. Type I SAMMVs will have the lowest phospholipid content of all SAMMVs. Both SUVs and LUVs that form with Nanoveson™ therapy and form SAMMVs are therefore expected to have less than 1% phospholipids as a percentage of their total volume. AA metabolites are expected to play a major role in the formation of Type I SAMMVs, the AA and AA metabolite content levels will be established with additional research.

Type II SAMMVs

Type II SAMMVs are hypothesized to include limited amounts of inspissated bile, more than Type I SAMMVs.

Type II SAMMVs are expected to potentially contain some multilamellar vesicles from inspissated bile. Type II SAMMVs will have more phospholipid content than Type I SAMMVs. Type II SAMMVs are hypothesized to contain 1% to 2% phospholipids by weight. Type II SAMMVs will have a higher percentage of phospholipids than Type I SAMMVs because they are hypothesized to contain more inspissated bile and therefore potentially more multilamellar vesicles formed in the biliary tract over time or formed in the intestines. It should be noted that the percentage weight of PL content of SAMMVs that determine Types of SAMMVs are expected to be adjusted with additional research and statistically significant numbers of samples for validation. The Type II SAMMVs are expected to also have higher AA and AA metabolite content than Type I SAMMVs.

Type III SAMMVs

It should be noted that Type III SAMMVs are theoretical at present as presented here and have not been documented in laboratory research. Type III SAMMVs are expected to be the least common form of SAMMV, occurring in a minority of patients, but occurring in patients with more complex and advanced liver disease. Type III SAMMVs are hypothesized to be aggregated from higher amounts of inspissated bile that is partially solubilized in the intestines and then aggregates. They may partially be formed from small inspissated bile plugs (IBPs) expelled from the biliary tract during Nanoveson™ therapy that once in the intestines are partially or fully solubilized and then aggregate additional digestion products and mixed micelles and vesicles that already include digestion products in their cores and become SAMMVs. Type III SAMMVs are expected to be greater than 2% phospholipids, but this level may change based on additional research. It is expected that Type III SAMMVs are expected to be far more uncommon than Type I and Type II SAMMVs. Type III SAMMVs may indicate potential of the therapy for cholestatic liver diseases, in addition to fatty liver. The expected AA and AA metabolite content of Type III SAMMVs is expected to be higher than Type I and Type II SAMMVs and will be established by additional research.

It should be noted that in one therapy session it is possible that Type III SAMMVs could be excreted along with Type I and Type II SAMMVs. Since they are expected to be similar in appearance this could confuse sample results when a sample of SAMMVs are homogenized for testing.

It may be discovered that more degradation of PL occurred in the limited research presented, and therefore SAMMVs may be found to contain more PL content than suggested above with more effective sample freezing techniques. Large amounts of digestive enzymes are expected to be present that will degrade PL rapidly. Only extensive additional research and controlled clinical trials over a large population will effectively determine the actual range of PL expected to be present in SAMMVs for the effective establishment of SAMMV types for biomarkers and diagnostics.

Non-SAMMV Excretions and Implications

The research presented is primarily interested in the biological, treatment, biomarker and diagnostic implications of SAMMV formation, TAG removal and the implications for liver disease and comorbid diseases. It is expected that other excretions are possible during therapy. It is recognized in the literature that gallstones that typically form in the gallbladder, can also form in the biliary tract, although biliary formed gallstones are expected to be fairly uncommon. It is possible that small bilirubin, cholesterol and/or calcium stones, that may form in the biliary tract, could be excreted during therapy. The maximum size of such stones that may be removed by the proposed therapy are unknown at this time.

Also, the potential risks to the patient of the therapy when such intrahepatic stones are present is currently unknown. It is suspected that when such small intrahepatic gallstones do exist in the biliary tract, TAG deposits upstream in the liver will be more extensive than would otherwise be expected. If such stones are removed by therapy, then SAMMV production may be increased, due to the release of TAG stores in the liver that built up due to the obstruction. Very minimal amounts of cholesterol ~1% have been discovered in SAMMVs to date, indicating they are not gallstones. The amount of bilirubin in SAMMVs is unknown, but it would be expected to be present. The amount of calcium and magnesium in SAMMVs is currently unknown, but is expected to be present. It is expected that multiple therapies will improve the cholesterol levels.

Magnesium Citrate vs. Magnesium Sulfate

Magnesium citrate is suggested as the cathartic/laxative agent for Nanoveson™ therapy for both patient compliance and commercialization reasons. Liquid oral magnesium sulfate poses serious taste challenges. Magnesium citrate is expected to have far greater appeal due to taste. This will increase consumer tolerance and compliance. However, advocates of comparable therapy, who do not understand the biochemistry at work, suggest that magnesium sulfate may be more effective for such therapy because it may produce more of what we term to be SAMMVs.

Research suggest that what is potentially occurring, if there is in fact greater SAMMV production with magnesium sulfate, is that magnesium sulfate is a faster acting and more effective cathartic, which removes more water from the body and intestines. By removing more water from the body and intestines with the 6 PM and 8 PM doses it is likely increasing the concentration of surfactants in the intestines during the therapy. Any additional concentration of surfactant further past the CMC level may allow a greater volume of SAMMVs to aggregate. However, it would not be expected to produce a net increase in the amount of liver TAG converted to phospholipids and removed by Nanoveson™ therapy. With magnesium sulfate, there may be more PL in SAMMVs vs. AQ, but this is not the goal of the therapy, nor would it improve the efficacy of the therapy.

However, it may be discovered that magnesium sulfate, at the doses being pursued for approvals, is more effective at lowering the pH in the intestines than magnesium citrate, and therefore potentially more effective at suspending pancreatic phospholipase A2 and leaving the key fatty acids bound to the PL for excretion. This would also mean that magnesium sulfate is also more effective at dropping pH in the intestines below the CMpH for bile salts, and therefore may possible promote greater SAMMV formation. Sulfate may also provide for differences in surface tensions and electrical charges and therefore thermal dynamics and kinetic energy related to micelle and vesicle formation and aggregation. However, magnesium citrate is expected to be very effective in this regard. Magnesium citrate is currently expected to be as effective as magnesium sulfate in therapeutic benefits with significant commercialization, marketing and compliance advantages.

For patients where magnesium sulfate is more effective at evacuating the intestines, making the therapy experience more pleasant in that regard, it may increase compliance and should be an option for both physicians and patients. The goal of Nanoveson™ therapy is the optimal removal of TAG converted to PL and removed from the body. The PL in AQ may be removed just as effectively as the PL in SAMMVs. Therapy effectiveness, commercialization issues and compliance must all be considered relating to the differences in magnesium citrate and magnesium sulfate. Approvals will be sought for both magnesium sulfate and magnesium citrate, but will likely pursue magnesium citrate initially.

Targeting Liver TAG for Removal

Halpern et al have noted that 90% of phospholipids in human bile are species of phosphatidylcholine (126). Hismiogullari et al determined that less than 20% of phospholipids in the hepatocytes are newly synthesized in the hepatocytes; and that hepatocytes acquire biliary lipid by three pathways, 1) biosynthesis, 2) lipoproteins, and 3) existing molecules drawn from intracellular membranes (17). They concluded that biliary phospholipids originate from limited sources: 1) synthesis via acylation of glycerol-3-phosphaate to phosphatidic acid, dephosphorylation to form diglyceride, and reaction with CDP-choline to form the phospholipid phosphatidylcholine (PC); and 2) uptake of phospholipids from circulating lipoproteins. They postulate that newly synthesized phospholipids provide only 3% of the biliary phospholipid output (17); the 3% is likely at normal physiological rates, but may rise sharply during Nanoveson™ therapy's increased demand for phospholipids. However, as noted above in the work of Patton et al and confirmed by Hismiogullari, the greatest source of bile phospholipids is remodeled TAG from the pool of hepatic TAG (4,17).

It has been observed that in normal persons the enterohepatic pool of PC is ~1 gram, and this pool circulates 5-10 times per day with almost complete hydrolysis and re-absorption of the PC (18). During Nanoveson™ therapy the circulation of phospholipids is interrupted, and they are aggregated and sequestered. It is expected that additional phospholipids are freshly minted by remodeling TAG in response to the 10 PM solution, and these phospholipids are also sequestered in the SAMMVs, if the phospholipid and bile salt content of the AQ is above the CMC and MPB required to produce micelles and vesicles. Through Nanoveson™ therapy, a significant multiple to the typical ~1 gram of PC circulating in the bile pool can be released in SAMMVs and AQ.

SAMMV Excretion

Following the morning dose(s) of Nanoveson™ MCL, the patient excretes the SAMMVs before 12 noon from the intestines, prior to re-absorption. There is simply no other way to systematically remove, in such a brief period of time, such a clinically significant amount of TAG and therefore AA and AA metabolites stored in the liver. SAMMVs may be passed throughout the day and even the following day, depending on the individual and whether one or two morning doses of the Nanoveson™ MCL are taken. Due to the high lipid content, the SAMMVs will float on the surface and can be easily strained and collected, when required, for biomarkers and laboratory analysis.

The potential amount of TAG converted to PL and excreted in SAMMVs is presented in FIG. 17. The numbers in this chart have been extrapolated to the higher SAMMV production. This data is very preliminary. It may be that as SAMMV volume increases the percentage of PL in SAMMVs and the ratio of PL in AQ will go down. This appears to be the case with these limited samples. More data is required to conclude on the actual amounts of TAG that will be converted to PL and excreted with Nanoveson™ therapy based varying levels of SAMMV production.

AQ/SAMMV PL Ratio—Phospholipids Excreted in Aqueous Solution

A focus of this application is the formation and excretion of SAMMVs as a key aspect of Nanoveson™ therapy. However, when phospholipid amounts in AQ exceed the CMC and allow formation of micelles, vesicles and SAMMVs, the amount of phospholipid in AQ, according to the principles of CMC, is expected to be far greater than that in micelles, vesicles and SAMMVs. It is also important to note here that PPLA2 has also been suspended from acting to cleave AA from the phospholipids in AQ. Any amounts of AA and its substrates estimated to be removed in SAMMVs, must be increased by a ratio to include the AA and its substrates removed from phospholipids in AQ.

It should be noted that the ratio of AQ/SAMMV amounts of phospholipids and AA removed is assumption based and theoretical at this point; i.e. subject to error. In order to calculate the ratio research was utilized that calculated the amount of total PC that is carried in micelles and vesicles in the biliary tract relative to AQ in the biliary tract. Booker et al did extensive research on seven individuals where they analyzed bile to determine the tendency of individual molecular species of fatty acids in the phospholipids to distribute between vesicles and micelles (119). Although the individual fatty acid species tended to distribute asymmetrically between vesicles and micelles, the vesicle/micelles ratios presented were used here to calculate a symmetrical overall vesicles to micelles ratio of 1.0375 to 1 ratio of PC distributed between vesicles vs. micelles.

The average amount of total biliary PC discovered in vesicles in the seven patients was recorded and this was utilized to calculate the average of 3.6% phospholipids in vesicles vs. AQ for the seven patients (119). Since the ratio of PC in vesicles to micelles is very close to 1/1 it was simply doubled to estimate the total PC in vesicles and micelles to be 7.2% of total PC in bile (119). This leaves 92.8 percent of the PC in bile in AQ and produces an AQ/SAMMV PC ratio of 92.8/7.2 or 12.8. Since PC makes up ~90% of the phospholipid in bile, we have used the 12.8 ratio for total AQ PL calculations.

SAMMVs are presently expected to be produced primarily by the aggregation of micelles and vesicles and therefore SAMMVs should only include PLs that have first aggregated into micelles and vesicles. The multiple of 12.8 was utilized to calculate an estimate of the PL content in AQ as compared to what has aggregated into SAMMVs. How this ratio may change in the intestinal tract is an unknown. On one hand, the ratio may increase since the monomers in AQ will be further diluted by the intestinal contents. However, if the pH in the intestines is below the bile CMpH, which leads to a new set of aggregation dynamics, there may be more PC in the aggregates than expected and the AQ/SAMMV ratio may decrease.

The hydrophobic and polar characteristics of the lipase activity on the 10 PM solution may change aggregation dynamics, increasing aggregation activity and decreasing the AQ/SAMMV PL ratio. The formation of SAMMVs may in fact remove the micelles and vesicles they contain from the CMC equilibrium equation. It may be discovered that due to the electrical or thermal dynamic properties present in the intestines during Nanoveson™ therapy, the phospholipids may bind directly to SAMMVs after the SAMMVs are initially formed, without first binding to micelles and vesicles; therefore the general notion of separating AQ vs. SAMMV PC in an AQ/SAMMV ratio may not be completely applicable. Microscopic analysis may determine if PL not incorporated in micelles and vesicles are able to bind to SAMMVs.

To summarize on this point, the 12.8 ratio of AQ/SAMMV PL content is utilized since a base for that ratio is established in the literature as reviewed. However, additional research is expected to provide the required evidence to adjust this ratio higher or lower. Even adjusting the ratio significantly lower, the amounts of PL and AA and its precursors removed by Nanoveson™ therapy are expected to be clinically significant. Adjusting it higher would mean that more PL, AA and the AA precursor LA is being removed by Nanoveson™ therapy than projected in the estimates presented.

The amount of AA removed in SAMMVs and AQ is important, and thus an accurate AQ/SAMMV ratio needs to be determined and established. However, what is likely more important is the amount of AA removed on an ongoing basis following Nanoveson™ therapy due to improvement in enterohepatic circulation and phospholipid synthesis; such improvements can be confirmed with blood plasma AA and other fatty acid ratio testing.

Phospholipids (PL) as SAMMV Sequestering Agent

Note that SAMMV formation is not completely understood at this time; much remains to be discovered and elucidated. However, the fact that the Nanoveson™ ingredients and procedure remain constant, intestinal conditions remain constant, and a patient can go from over 100 grams of SAMMVs per Nanoveson™ treatment to zero SAMMVs provides evidence to suggest that only the biliary excretions are changing. The total percentage of PL in SAMMVs is low, explained by the structure of unilamellar vesicles with all the phospholipids in the membranes. The phospholipids in the membranes consists of up to ~2% of the total unilamellar vesicle material in the examples presented.

Only micellisation of phospholipids in conjunction with dietary content and vesicle production, as explained above, have the biochemical characteristics to explain such SAMMV production and content; at least as discovered to date. That liver TAG remodeled into PL released in the bile appears to be acting as the membrane and key sequestering agent for SAMMV formation is perhaps the most fascinating aspect of Nanoveson™ therapy. The dietary lipids and content clearly play a major role in SAMMV formation, but it is expected to be only in conjunction with the biliary phospholipids. However, other biliary agents are expected to be discovered to contribute to sequestration and SAMMV formation, such as some impact from bile salts and AA metabolites, but phospholipids are presently expected to play the lead role in biochemical importance in the formation of SAMMVs.

Reducing Fatty Liver—Removing TAG

NAFLD is considered to exist when the liver is more than 10% TAG by weight, which shows up on ultrasound or in elevated liver enzymes, or is discovered by biopsy. It is likely that SAMMVs will be produced by Nanoveson™ therapy when liver TAG deposits are at lower levels than those at which point NAFLD is diagnosed. The threshold for SAMMV formation is hypothesized to be when the amount of PL released by Nanoveson™ therapy is above the CMC and MPB in the intestines, or when IB and/or IBPs are present in the biliary tract and not only when a liver is categorized clinically as "fatty". The SAMMV formation level may be reached with Nanoveson™ therapy when the liver is only 1-5% stored TAG by weight. The actual level is simply unknown at this time.

Figure 8:
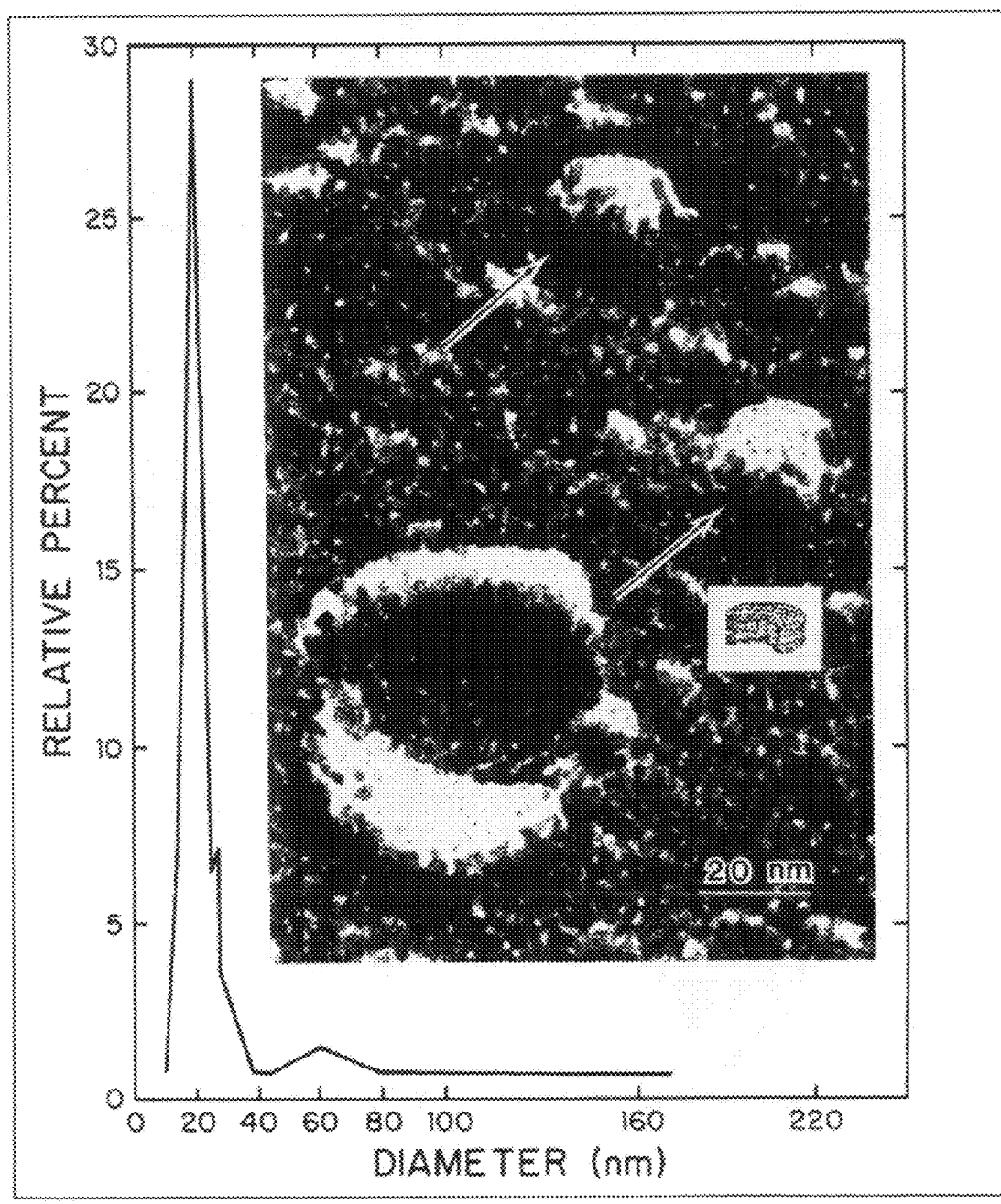
FIG. 8 shows an extreme magnification view of small vesicles with a scale drawing of a mixed lipid micelle. Arrows indicate small vesicles which project out of the plane of the page. The granular background is made up of platinum grains 24 nm in size (130).
Figure 9:
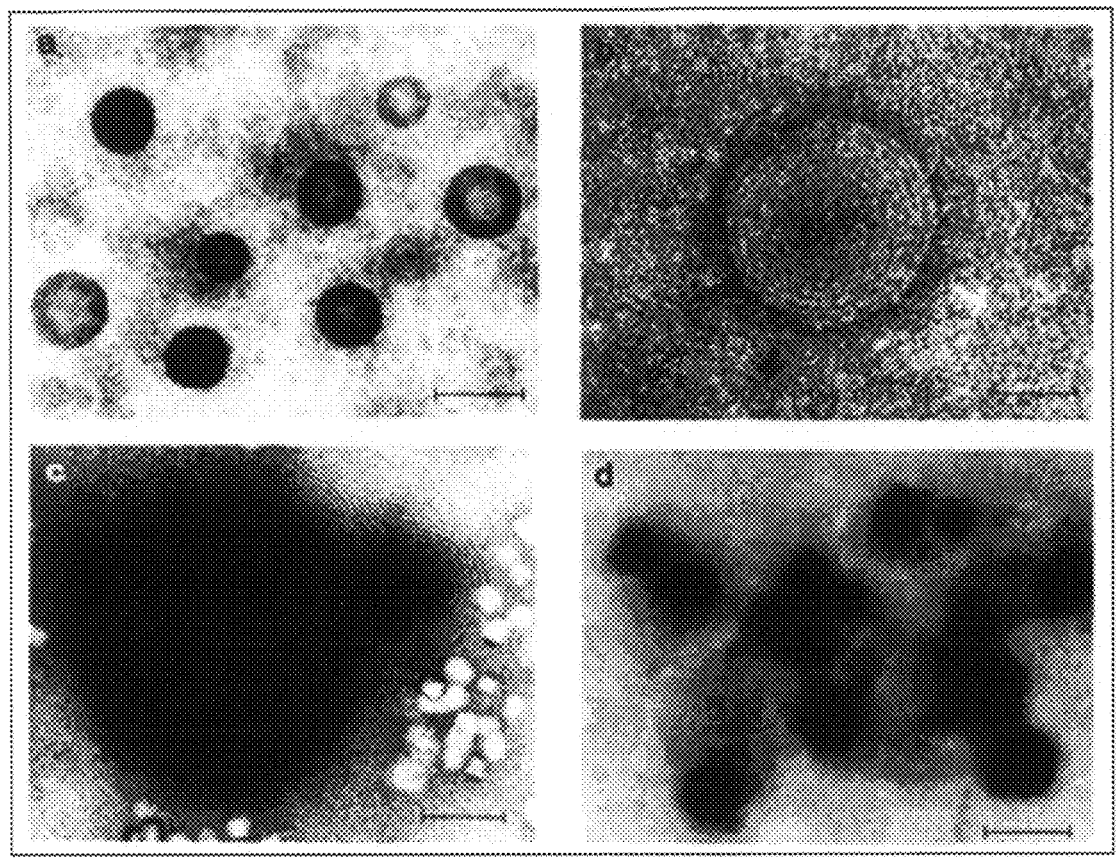
FIG. 9 shows model bile over time. A) Unilamellar vesicles (1 hr) (bar=87 nm); B) multilamellar vesicles (4 hr) (bar=50 nm); C) fusion of multilamellar vesicles (8 hr) (bar–38 nm); D) clusters of vesicles (12 hr) (bar=347 nm) (134).
Figure 11:
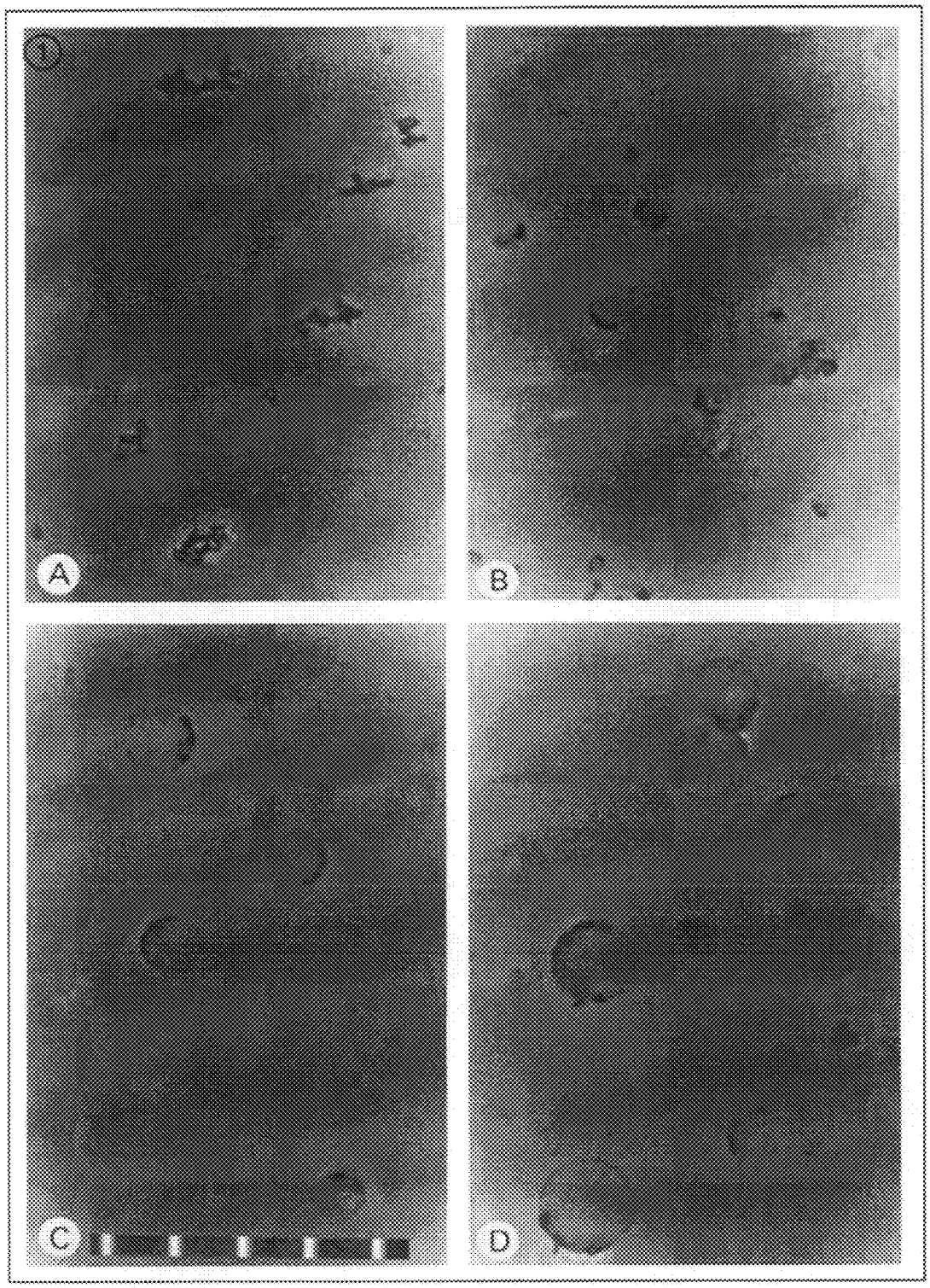
FIG. 11 shows a visualization of chromaffin granule fusion in the phase microscope. (A) Clumps of granules that have been aggregated by incubation with synexin and Ca2+ for ~40 min. (B-D) Vesicles of various sizes formed after further incubation of the preparation for ~15 min in the presence of 4 ug/ml arachidonic acid. Graticule marks are 10 um apart (139).
Figure 12:
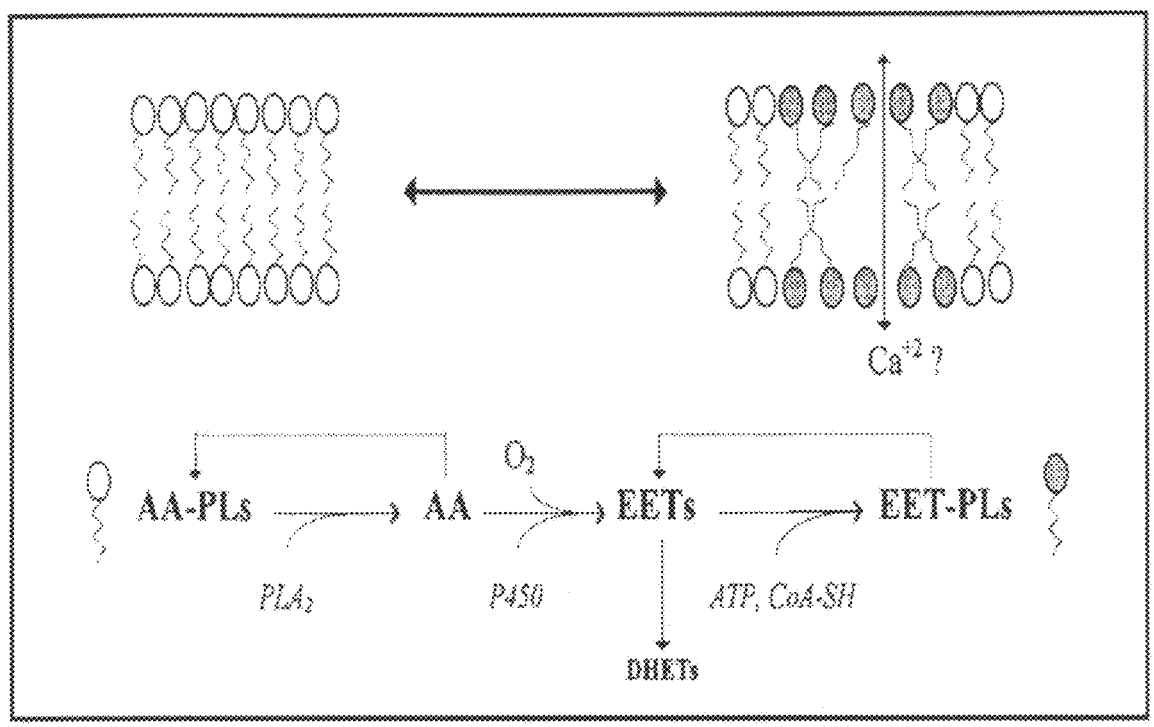
FIG. 12 shows an illustration from the work of Capdevila J H et al. in their discussion of Cytochrome P450 and membrane micro-environments (154). Cytochrome P450 enzymes are highly active and available in the liver. AA metabolites produced from the AA monooxygenase Cytochrome P450 pathway in the liver, and specifically those related to bile production, are expected to be released in relevant amounts during therapy and are expected to play a role in vesicle membrane fusion and SAMMV formation.
Figure 13:
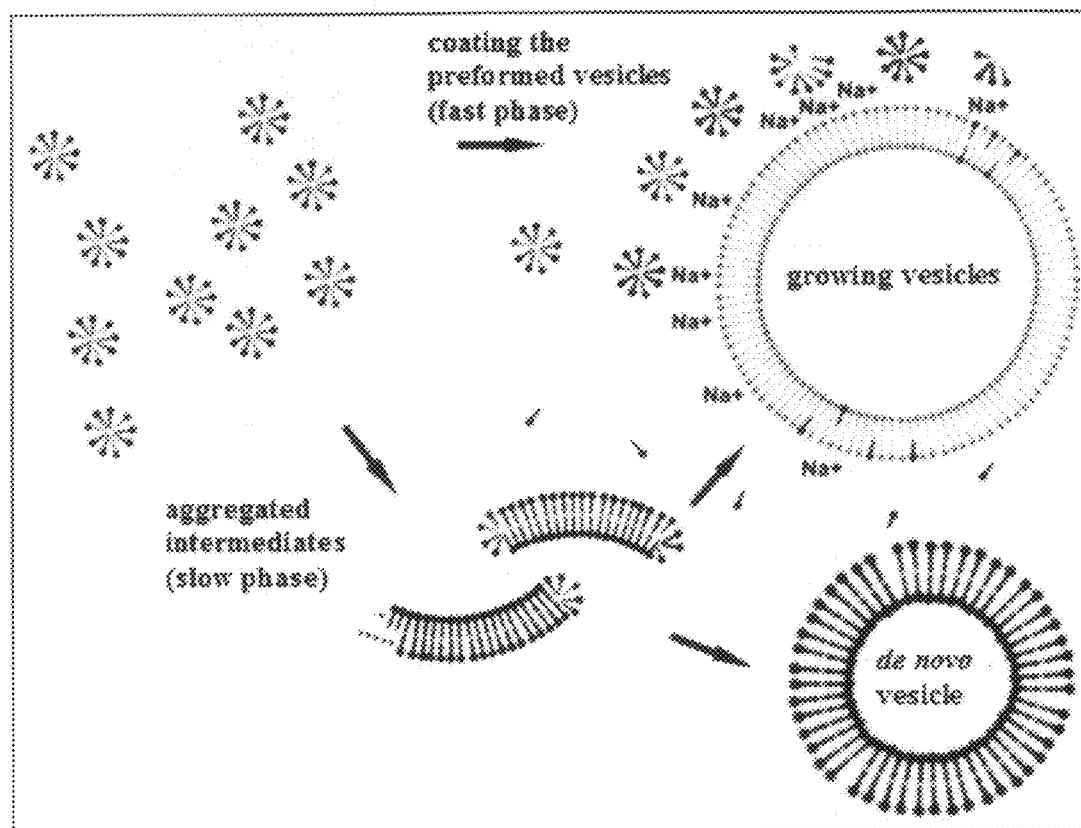
FIG. 13 is a diagram illustrating the proposed scheme of dynamic processes occurring during micelle addition to pre-formed fatty acid vesicles by Chen and Szostak (136). It is proposed that what occurs during Nanoveson™ therapy may be similar to this proposed scheme as preformed biliary vesicles enter the intestines when the intestinal content of phospholipids from bile is above the CMC and the MPB in the intestines, thus allowing for biliary preformed vesicle growth and the formation and aggregation of micelles, de novo vesicles and in turn SAMMVs.
Figure 14:
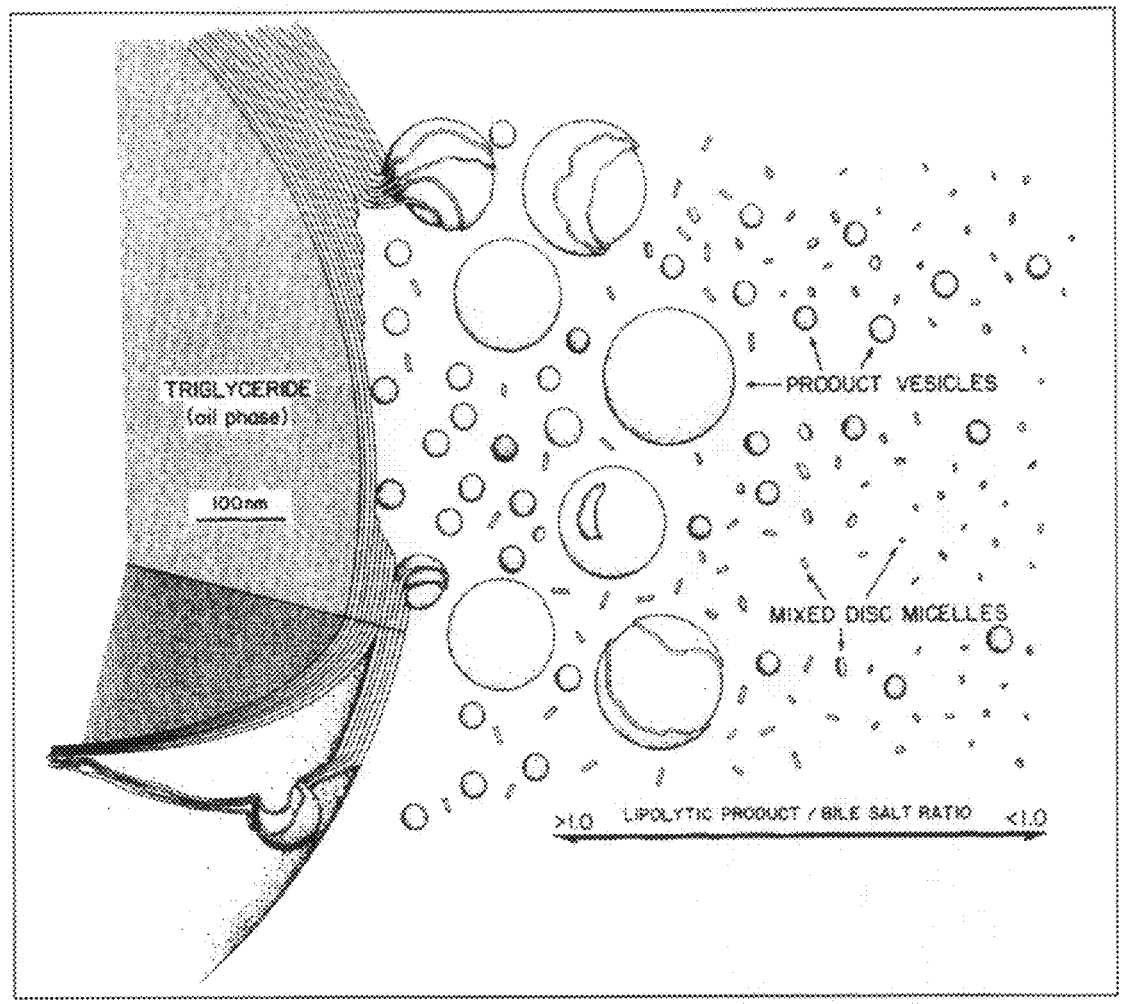
FIG. 14 shows accumulation of product lamellae and their dispersion into vesicles (130). As micelles aggregate they morph into vesicles. As vesicles absorb bile salts then can convert back into micelles. Phospholipids and bile salts contain the properties required to produce micelles and vesicles. Simple bile salt micelles can form, i.e., only containing bile salts, as opposed to mixed micelles. Simple phospholipid micelles can form. Vesicles membranes can contain just phospholipids or be mixed and contain bile salts, cholesterol and other lypolytic products. The charge of the surface of the vesicles is expected to attract the TAG and incorporate it into the vesicle for digestion.
Figure 15:
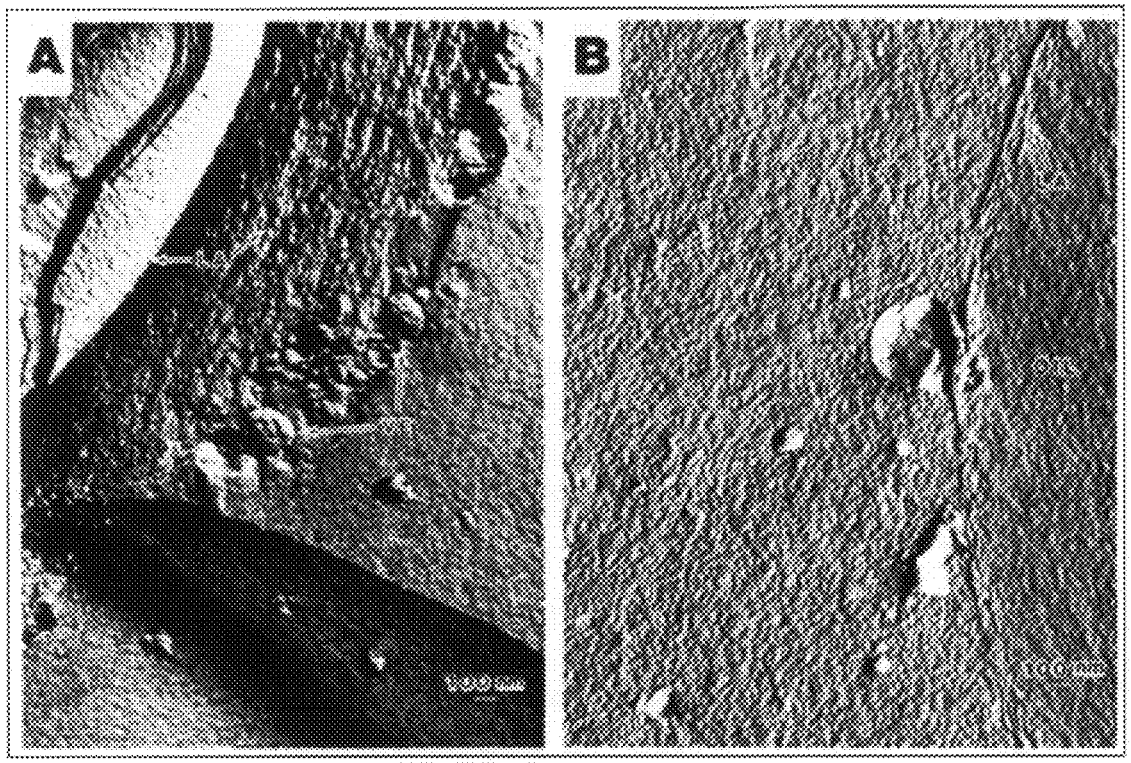
FIG. 15A) shows an image of vesicles (VE) during lypolytic product morphology of two systems containing lipase, bile salts and triglyceride and product lamellae (LA). It should be noted these are not phospholipid vesicles, but would be similar in form.
FIG. 15B) shows an image of vesicles evident in 42 nM pig gallbladder bile and pig pancreatic juice that would include phospholipids (130).
Figure 16:
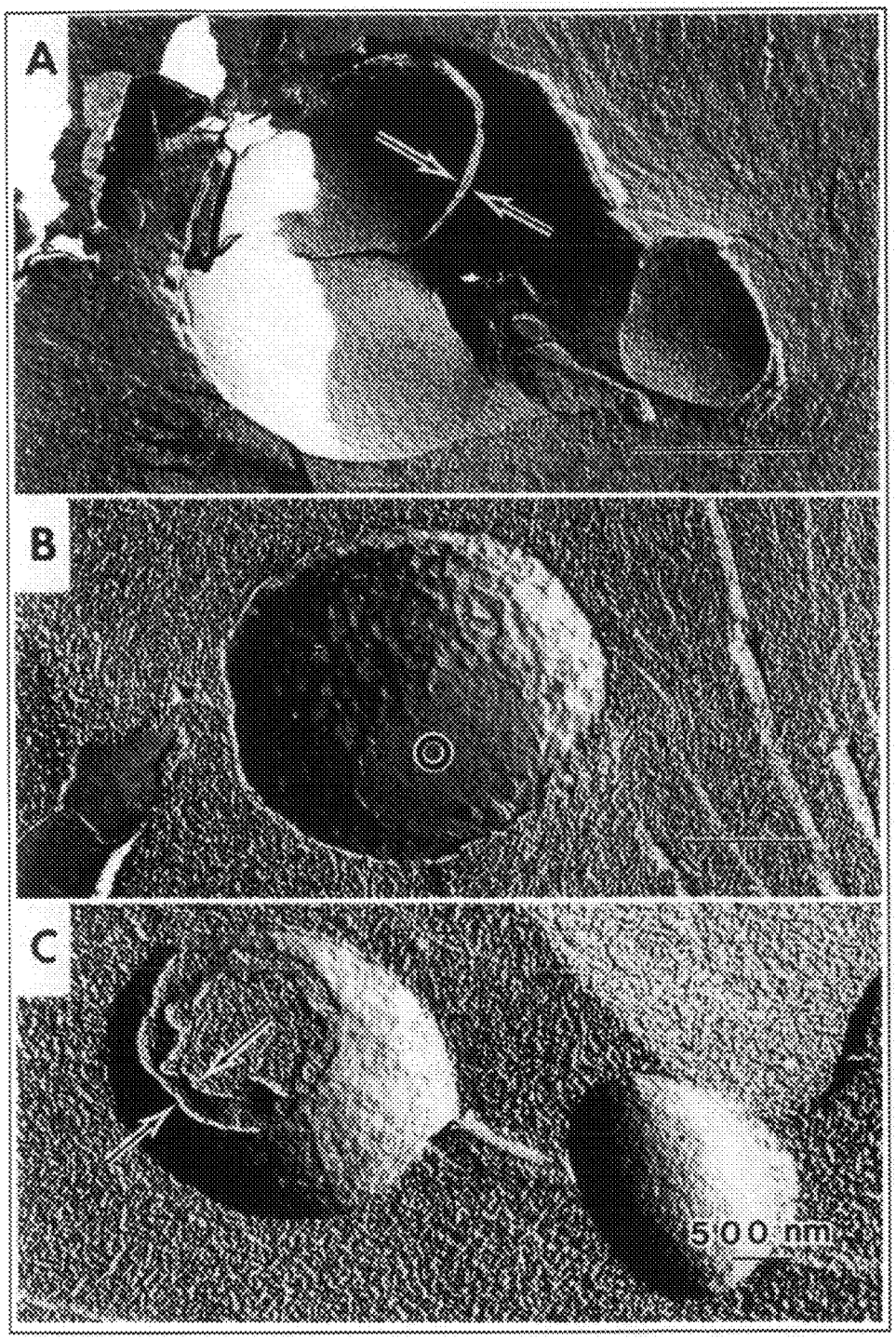
FIG. 16A) shows multilamellar product vesicle.
FIG. 16B) shows partially digested TAG droplet showing an oil core (O) and rough textured surface.
FIG. 16C) shows etched product vesicles as in A, showing an aqueous core and lamellae (130).

Substantial amounts of phospholipids, made largely from remodeled TAG, is sequestered in the SAMMVs. See FIG. 8 for more information on the amount of PL that is presently expected to be removed by Nanoveson™ therapy at different gram levels of SAMMV production. Current estimates are based on limited laboratory analysis to date, and need to be confirmed over statistically relevant number of patients, but represents a significant amount of TAG (fat) being removed from the liver, and is anticipated to be able to treat fatty liver in conjunction with dietary changes. If dietary changes are not made by the patients, it is not likely that Nanoveson™ therapy will ever be able to completely restore a healthy lipid balance to the liver and SAMMVs will continue to form with Nanoveson™ therapy.

Clinical trials will determine the benefit of Nanoveson™ therapy when there is insufficient levels of TAG to be declared fatty liver, but enough TAG to produce SAMMVs. It is expected that use of Nanoveson™ for removal of minimal levels of liver fat deposits may be beneficial, although certainly not to the extent of higher levels of liver fat and when NAFLD is present. Research and trials will also determine if Nanoveson™ therapy is beneficial when no SAMMVs are produced, and determine how much remodeled TAG as PL is being released in AQ when PL<CMC and/or <MPB and no SAMMVs are produced.

The amount of liver TAG remodeled into PL and removed in the SAMMVs can be significant. If 100 grams of SAMMVs are produced, it is estimated that 11 to 26 grams of PL from remodeled TAG can be removed from the liver, note the AQ/SAMMV ratio is key in this calculation. Note that these estimates, based on gram weight of SAMMVs, are subject to significant error. It may be that the greater the amount of SAMMVs produced, the lower the amount of PL content, thus a smaller amount of remodeled TAG than anticipated. However, it is expected that even if these ratios and numbers change significantly, there will still be a clinically significant amount of remodeled TAG in the form of PL removed from the liver by Nanoveson™ therapy.

Lipid Remodeling and the 10 PM Solution

The amount of fat taken orally in the 10 PM solution that is absorbed during Nanoveson™ therapy is expected to be limited; as long as SAMMVs are produced a great deal of the fat in the 10 PM solution is converted to micelles and vesicles and absorbed into the SAMMVs and excreted. However, the total amount absorbed is presently unknown. The amount of dietary fat in the 10 PM solution likely exceeds the maximum amount of fat that can be absorbed by the intestines in the time available in transit before excretion due to the cathartic action of the therapy; therefore, expulsion of much of the fat in the 10 PM solution takes place in the SAMMVs and AQ and goes unabsorbed. Nanoveson™ will explore adding ingredients that decrease the absorption of fat, such as additional phospholipids and potassium, that may increase the saponification and micellisation of the dietary fats and their binding and thus release in SAMMVs.

The fat that is absorbed from the 10 PM solution is primarily monounsaturated omega 9 fats and omega 3 fats; which replace saturated fats, polyunsaturated AA and polyunsaturated LA that is released and sequestered in the SAMMVs and excreted. Therefore, Nanoveson™, in addition to removing excess fat from the liver, also effectively acts as fatty acid or lipid remodeling and replacement therapy; i.e., replacing unhealthy amounts of fatty acids with a healthier balance of fatty acids. Once SAMMVs are no longer produced, fat absorption from Nanoveson™ therapy is expected to increase; therefore, therapies beyond a limited number for maintenance, when no SAMMVs are produced, may not be efficacious and will not likely be advised.

Non-Fatty Liver Nanoveson™ Therapy Formulation for Biomarkers and Diagnostics

If a patient does not have fatty liver or liver TAG deposits in hepatocytes that are high enough to convert sufficient TAG to PL that exceeds CMC and the MPB in the intestines SAMMVs are not expected to form. SAMMVs may also not form because there is a biliary tract obstruction and therefore sufficient PL is not released to form SAMMVs. Such potential causes of non-SAMMV formation, when fatty liver is suspected, will need to be carefully considered and evaluated by physicians.

Although fatty liver is prevalent in many liver diseases, there are liver diseases where excess TAG or fatty liver will not be present in sufficient quantity to release sufficient PL to form SAMMVs, but the biomarkers and diagnostics results would be helpful. The evidence presented on SAMMV formation indicates that is would be possible to add PL and free fatty acids such as AA to the 10 PM solution to force the vesicle fusion and formation of SAMMVs, when fatty liver does not exist. The reason for such a version of the product would be to force SAMMV formation in order to aggregate liver and biliary excretions for biomarkers and diagnosis purposes. If fatty liver is not present there may be other compounds such as DNA, bacteria, viruses, catecholamines, annexins, AA metabolites, etc. that will be established as biomarkers for the purpose of diagnosis. A version of Non-Fatty Liver Nanoveson™ therapy with added PL in the 10 PM Solution may prove valuable for biomarkers and diagnosis and as standard therapy.

Cholestatic Liver Diseases: Inspissated Bile (IB) and Plugs (IBPs)

In obstructive liver diseases, there can be formation of inspissated bile (IB) and inspissated bile plugs (IBPs) in the intrahepatic and extrahepatic biliary tract. IB and IBPs in these diseases include aggregates of vesicles and micelles constructed of bile components that form in the liver and biliary tract. Such disease will include cholelithiasis, cholestasia, cholestatic hepatitis, cholestatic jaundice, biliary stasis, etc. Such cholestatic liver diseases often progress to cirrhosis of the liver and liver failure. IB and IBPs of cholestatic liver disease if excreted during Nanoveson™ therapy may be partially or fully solubilized and then re-aggregate as SAMMVs in the intestines and incorporate newly formed micelles and vesicles in the intestines.

IBPs that form in the liver and biliary tract will be made of vesicles that contain different monomers and compounds, but have phospholipid membranes. SAMMVs that form in the intestines will have phospholipid membranes, but the contents inside the phospholipid vesicle membranes will be different, and are expected to include free fatty acids and potassium carboxylates.

It is hypothesized that Nanoveson™ therapy, due to the marginally increased biliary pressure combined with the large volume of bile production, is capable of forcing inspissated bile and certain sizes of bile plugs out of the biliary tract and into the intestines. This potential has significant implications for treating liver diseases that ultimately lead to the requirement for liver transplantation.

Before an actual inspissated bile plug forms, it will be preceded by inspissated bile that is caused by various stages of biliary stasis. IBPs block bile flow, thus exacerbating liver disease. Up stream in the biliary tract from inspissated bile there may tend to be fatty liver deposits, since these areas of the liver cannot release optimal amounts of bile and phospholipids. The literature suggests that IBPs in the common, cystic and hepatic biliary ducts, play a role in the pathogenesis of many different liver diseases, however there is not a great deal of detail available or research available on the formation and consistency of IB and IBPs and their full impact and relevance to liver disease.

A key aspect of the Nanoveson™ therapy method of action hypothesis is that it may be possible for some small IBPs to be removed by the marginally higher biliary pressure when combined with the high rate of bile flow required and produced by Nanoveson™ therapy. There is similarity between IBPs formed in the biliary tract and SAMMVs formed in the intestines, specifically in the fact that they are both partially formed from aggregated lipid micelles and vesicles. The phospholipid content is therefore similar. However, IBPs that form in the biliary tract would be expected to have higher percentage amounts of phospholipids since they would have taken longer to form and would have more multilamellar vesicles, i.e. vesicles with more membranes and more phospholipids. The full role played by IBPs, as well as intrahepatic bile nucleation and inspissation on the formation of SAMMVs in the small intestines during Nanoveson™ therapy is yet to be fully elucidated.

Cholestasis is a more advanced liver diseases than NAFLD. Obstruction of cholestasis can produce bile ductular proliferation, inspissated bile in bile ducts, portal tract edema, neutrophilic inflammation, and cholate stasis of periportal hepatocytes (41). It is expected that that biliary pressure created by the lipid fasting aspect of Nanoveson™ therapy will create marginally but clinically significant increased pressure in the liver, gallbladder and biliary tract. It is expected that IBPs, up to a certain size, can be expelled from the intrahepatic and extrahepatic biliary tract by Nanoveson™ therapy. The maximum size of bile plugs that can be expelled is unknown, and will likely vary with different patients. In cases of common bile duct distention due to biliary obstruction, larger bile plugs may be possible.

Inspissated bile obstructions that are expelled into the duodenum during Nanoveson™ therapy that are partially or fully solubilized in the intestines may be combined with the high phospholipid concentration in the intestinal aqueous solution to form SAMMVs. Intrahepatic nucleation and inspissation of bile phospholipids as aggregated vesicles and the existence of cellular debris may occur more frequently than is currently recognized in medicine and the research. Primary sclerosing cholangitis (PSC) leads to increased inspissated bile and bile plug blockage. Note that in the research of Bambha K et al at Mayo it is suggested that the prevalence of PSC in the United States, with its attendant medical burdens, is significantly greater than previously estimated (28).

Various stages of bile stasis, ranging from microscopic aggregates to relatively large mixed micelle aggregates of phospholipids and bile salts may be more common than expected, as liver disease appears to be proliferating. Biliary obstruction plays a role in the molecular pathogenesis of cholestasis and other liver disease (22). Inspissated bile syndrome has been observed in cystic fibrosis (127). Multiple Nanoveson™ therapies may potentially remove some biliary obstruction. A clinical trial for treatment of cholestasis is intended for Nanoveson™ therapy, and trials for other liver diseases that involve the various forms of obstruction are under consideration.

Clinical trials that establish Nanoveson™ as viable therapy for cholestasis and other obstructive and cholestatic liver diseases are desperately needed, and would represent a breakthrough in the treatment of liver disease. Nanoveson™ therapy in conjunction with established therapy with deoxycholic acid may prove more efficacious for treatment than deoxycholic acid alone.

Biliary Sludge, Biliary Casts and Liver Transplantation

Biliary sludge and biliary casts also have limited review and analysis in the literature. Cellular debris is the primary component of biliary sludge, which is a fundamentally different consistency than bile plugs. It may include connective tissue from destroyed bile duct walls (23). It has been clearly established that biliary sludge is a serious life-threatening problem post liver transplantation (23). Nanoveson™ may prove to be a potential treatment option for this life-threatening risk.

Clinical trials need to be conducted to provide evidence as to whether biliary sludge can be removed by the marginal bile pressure increase and rapid bile flow produced by Nanoveson™ therapy from non-transplant patients and transplant patients. Biliary sludge has been implicated in multiple liver and biliary tract diseases (24). It has been suggested by researchers that a better appreciation of the pathogenesis of sludge will assist in addressing biliary disorders (24). Nanoveson™ clinical trials may provide a basis for this appreciation but will pose substantially greater risk than less severe and less complicated indications.

SAMMV formation from Nanoveson™ therapy is expected to be increased in the presence of biliary sludge when biliary sludge is due to increased levels of biomolecules that cause fusion and aggregation of vesicles in the biliary tract, including AA, AA metabolites and other FA metabolites. Increased biliary pressure and lipid polymorphism of liver TAG into PL, as a result of Nanoveson™ therapy, forces biliary sludge into the intestines. Biliary sludge, once forced into the intestines and combined with the dietary products of the 10 PM Solution is expected to create an environment for vesicle growth and aggregation that forms SAMMVs in the intestines.

When biliary sludge has aggregated in the biliary tract it can form obturating feltlike or firm cast (23). Biliary sludge has been reported in up to 29% of patients that have undergone liver transplantation (23,86,87). The research presented may indicate that post transplantation biliary sludge may be caused by an increase load on the liver and biliary system to remove AA and AA fusogenic fatty acid metabolites and other fusogenic biomolecules from the body stores of such compounds post liver transplantation.

An important aspect of Nanoveson™ therapy related to biliary casts is that it may be possible for a patient to potentially excrete limited size biliary casts with Nanoveson™ therapy. The common bile duct is likely dilated due to the presence of the cast. The additional bile pressure and bile flow produced by Nanoveson™ therapy may force such material to pass into the duodenum. If such efficacy is proven, this would be a revolutionary mode of treatment for transplant patients that face the life-threatening complication of biliary casts.

The observations of Textor S C et al (31) on AA metabolite excretion post liver transplantation, when combined with the research of Creutz (144,145) regarding the fusogenic properties of AA and AA metabolites and other biomolecules, may help explain the formation of biliary sludge post liver transplantation. Biliary sludge would be expected to include, and may partially be caused by, excessive amounts of vesicle fusion and aggregation in the biliary tract. Liver transplantation may shift the patient's excretion pathway of AA metabolites from kidneys and lungs to the liver. The anticipated build up of AA in blood plasma, tissues and organs prior to transplantation would be expected to increase the load of AA an AA metabolite excretion in a newly transplanted liver as the biliary pathway for AA and AA metabolite excretion becomes available, which will increase the fusogenic compounds in bile above normal, thus causing biliary sludge post liver transplantation.

Nanoveson™ therapy could potentially be utilized to treat transplant patients with complications of biliary sludge and biliary casts to improve outcomes by preventing such complications. Gross et al at Mayo have conducted extensive research on quality of life issues before and after liver transplantation (29). Nanoveson™ therapy could theoretically have a relevant impact on the quality of life of transplant patients after transplantation, and may conceivably be able to extend the life of those awaiting transplantation.

It is possible that a non-transplant patient that has suffered from long term fatty liver disease has compromised whole body AA homeostasis. If such a patient begins Nanoveson™ they could develop biliary sludge following one or more initial Nanoveson™ therapies as the amount of fusogenic AA and metabolites and possible other fusogenic compounds processed by the liver increase. Additional Nanoveson™ therapies should address such cases of biliary sludge and may provide insight into biliary sludge for transplant patients.

Cirrhosis and Primary Biliary Cirrhosis

The origins of cirrhosis as alcoholic fatty liver are similar in many respects to NAFLD. The difference is that alcohol consumption triggers the buildup of fat in the liver that leads to cirrhosis as opposed to dietary and other causes of NAFLD. However, it is becoming evident that NAFLD can also lead to more advanced liver disease, including cirrhosis.

There is the potential for Nanoveson™ therapy to have a positive impact on outcomes for cirrhosis and its precursors, such as primary biliary cirrhosis. If Nanoveson™ therapy can reverse the buildup of stores of TAG in the liver for NAFLD, there is reason to believe that it could also do so for alcoholic liver disease and cirrhosis. This is an exciting prospect. Additional research is required to consider all the implications on this front, as with other targeted ailments. Treatment of cirrhosis would require patients to reverse destructive alcohol consumption patterns. Alcohol consumption interferes with the liver's ability to convert TAG to phospholipids and thus leads to its storage as TAG and subsequent long-term liver damage.

Kim W R and Dickson E R at the Mayo Clinic have developed the Mayo natural history model to depict patient survival for primary biliary cirrhosis in the absence of effective therapeutic intervention (30). Such a model would be useful as a tool to measure the effectiveness of Nanoveson™ therapy to improve the outcomes of primary biliary cirrhosis patients.

Arachidonic Acid (AA)

The intent is to pursue an FDA approved treatment option for NAFLD and other liver diseases, but the implications of Nanoveson™ go beyond liver disease due to its mechanism of action; i.e. the removal of targeted excess fatty acids in TAG, including AA and its precursors, from the liver and improvement of enterohepatic circulation. Many may view Nanoveson™ therapy impact on AA related diseases as the more important discovery if the method of action and efficacy is confirmed.

Linolenic acid (LNA) and Linoleic (LA) acid are the two essential fatty acids in humans. LA 18:2 is a polyunsaturated omega n-6 fatty acid and is the precursor to AA 20:4 n-6, i.e. the body can make AA out of LA. LNA 18:3 n-3 is a polyunsaturated omega n-3 fatty acid and is the precursor to eicosapentaenoic acid (EPA) 20:5n-3. Both AA and EPA are precursors for eicosanoids; but EPA is expected to play the minor role. AA and eicosanoid activity are critical for sustaining life; the problem comes when they are available in excess and in disproportionately high amounts relative to the other fatty acids. AA, and it precursor LA, are two of the fatty acids causing fatty liver.

Zhou and Nilsson reported that a 70-kg (154 lb.) human contains 50-100 g of AA (19); 100 g is equal to 3.52 ounces (19); this estimated AA human content is likely a typical Australian rather than a typical westerner. Estimates have not been located in the literature for total amounts of AA in the typical U.S. adult, but an obese individual on a western diet, or a lean individual with fatty liver, would be expected to have substantially greater stores of AA available for the AA cascade to drive inflammatory diseases.

Removing Clinically Significant Amounts of AA

The numbers presented on removing AA and LA with Nanoveson™ therapy should be considered very preliminary, as research and the number of samples thus far are very limited. When sufficient levels of TAG are present in the liver the TAG converts to enough PL at levels above the CMC so that SAMMVs are formed and AA is released in SAMMVs and AQ. The amount of potential AA removed from the body by a single Nanoveson™ treatment procedure is expected to be in the range of 1 to 1.5 grams of AA (see FIG. 10). This is a mid-range estimated when 50 to 75 grams of SAMMVs are released. This amount of AA represents as much as 2-3% of the human body content of AA based on reported total body stores of AA (19), but that total body estimate could be low. On the low end, the AA removal could be 100 mg or less per Nanoveson™ treatment. On the high end, there could be as much as 4 grams of AA removed per Nanoveson™ treatment. It should be noted that these estimates include a number of key assumptions. The amount of AA removed is dependent upon the amount of SAMMVs produced and the ratio of AA in the SAMMVs compared to AA in AQ. The removal of LA, a precursor for AA synthesis, may be in greater amounts than the removal of AA for most patients; and have an impact in future AA activity due to the LA being unavailable for conversion to AA.

Clinical trials are required to fully quantify and confirm the total amounts of AA and AA substrates removed by Nanoveson™ therapy. Clinical trials will confirm if the removal of these amounts of AA and AA substrates have the anticipated measurable and statistically significant effects for the treatment of AA cascade related diseases. Using the above numbers, a dozen Nanoveson™ treatments over an extended period, when SAMMVs are still being produced by Nanoveson™ therapy, could remove as much as 30 to 40 grams or more of AA from the body. These larger amounts are only expected to be applicable in patients with fatty liver and/or obesity. This amount of AA removed is expected to have a clinically significant impact on AA cascade related diseases as a treatment, and AA related disease prevention.

Clinical trials are required to provide confirming evidence that Nanoveson™ therapy is sequestering and removing statistically and clinically significant levels of both AA and its precursor LA from the human body. It is hopeful that levels of available AA in the liver, blood plasma, and tissue will be reduced, and documentable with blood plasma panels. With an understanding of the AA role in many diseases, the anticipation is that Nanoveson™ can treat and reduce the human body's susceptibility to diseases driven by the AA cascade, and reduce or reverse the damage done by inflammatory eicosanoid activity.

Restoring Whole Body Quantitative AA Homeostasis

The key to Nanoveson™ therapy related to AA driven diseases is that it does not just remove the AA during Nanoveson™ therapy, but is restores AA homeostasis over time by removing fat from hepatocytes, which impede optimal bile salts release and subsequent bile flow and enterohepatic lipid homeostasis functions. The research of Werner et al was extremely important to the implication of Nanoveson™ therapy research when they observed that their research results support the concept that biliary secretion of AA in the form of phospholipids quantitatively affects overall body AA homeostasis (45). This principal is crucial to the proposed efficacy of Nanoveson™ therapy to address AA related diseases. By removing excess AA stored in the liver in the form of liver TAG and improving enterohepatic circulation by ensuring the biliary tract is clear and optimally functional, it is hopeful that AA homeostasis can be obtained and maintained with Nanoveson™ therapy.

The AA Cascade

AA typically resides in the sn-2 position of a phospholipid. The AA cascade begins when AA is cleaved from a phospholipid by phospholipase A2, triggering the AA cascade and the production of eicosanoid byproducts. There are three primary pathways of AA oxidation: 1) cyclooxygenase; 2) 5-lipoxygenase; and 3) cytochrome p450 Monooxygenase. Prostaglandins and thromboxanes are produced by the cyclooxygenase pathways, COX1 and COX2 (49). Leukotrienes are produced by the 5-Lipoxygenase pathway (49). Monooxygenase is the less known pathway and produces three types of eicosanoids: 1) midchain conjugated dienols (5-, 8-, 9-, 11-, 12-, and 15-HETEs); 2) w-terminal hydroxylation forms C16-C20 alcohols of AA (16-, 17-, 18-, 19-, and 20-HETEs); and 3) olefin epoxidation (also called the epoxygenase reaction) results in the production of four cis-epoxyeicosatrienoic acids (14,15-, 11,12-, 8,9-, and 5,6-EETs), each of which can be formed as either the R,S or the S,R enantiomer. (60). Research indicates that activity of these eicosanoids produced from the AA cascade play a role in most inflammatory diseases, including gastrointestinal disease, cardiovascular disease, arthritis and cancer.

Considering the AA cascade and eicosanoid activity related to the role of the liver, it is interesting to note that Textor S C et al from the Mayo clinic observed that high levels of urinary eicosanoids in patients with liver disease fall rapidly after liver transplantation during Ciclosporin immunosuppression. The researchers concluded that renal vasoconstriction in humans may be associated primarily with suppression in renal prostacyclin excretion rather than stimulation of thromboxane (31). This research highlights the role played by liver function in inflammatory conditions and the liver's ongoing pursuit of AA homeostasis through ongoing enterohepatic circulation.

AA and Cancer

Butcher et al observed that there is suggestive evidence that dietary n-6 polyunsaturated fatty acid may increase the incidence of some types of tumors and that AA (52,53,54,55) therefore may play a more extensive role in growth than has hitherto been recognized (52,53,54,55,56,57,58,157,158,159,160,161,174).

Angiogenesis is a prerequisite for tumor growth and metastasis. Vascular endothelial cell proliferation, migration, and capillary formation are stimulated by angiogenic growth factors, which include eicosanoids synthesized from n-6 fatty acids like AA. Angiogenesis in solid tumors relates to poor prognosis and, in premalignant lesions, indicates potential for cancerous transformation (50). Genotoxic byproducts of both cylooxygenase and lipoxygenase-catalyzed AA metabolism are suspected to contribute to genetic instability and thus to malignant progression of tumor cells (51).

In 2006 Hughes-Fulford et al reported that there is increasing support to show that essential fatty acids stimulate cell growth and that data implicate AA as a growth mitogen (103). They observed that over the past 50 years, the dietary intake of omega 6 to omega 3 fatty acids has increased from a ratio of 2:1 to 25:1 in Western cultures and this may be a factor in the activation of latent prostate tumors (103, 105). Ghosh and Myers documented that AA was found to be an effective stimulator of human prostate cancer cell growth in vitro at micromolar concentrations (104). AA needs is metabolized through the 5-lipoxygenase pathway to produce 5-HETE series of eicosatetraenoids for its growth stimulatory effects on human prostate cancer cells (104).

Research on the connection between AA and cancer is accelerating. A large body of evidence demonstrates a close relationship between aberrant AA metabolism and many types of human cancers (48). Inhibiting cancer growth by preventing AA metabolism into eicosanoids has been the focus of much of the research. Nanoveson™ therapy approach is to target and reduce the size of the pool of free AA, improve enterohepatic homeostasis to ensure the ongoing release of AA and AA metabolites in bile, thereby preventing its availability for excessive and aberrant metabolism into inflammatory and cancer stimulating eicosanoids.

AA and Cardiovascular Disease

Park S C et al provide an excellent review of and literature references to the suggested connection between the development of hypertension, diabetes, and cardiovascular disease and AA metabolism, noting that as a member of the n-6 polyunsaturated fatty acids (PUFAs) that AA is a precursor of thromboxane A2 (TXA2), a potent promoter of platelet aggregation and vasoconstrictor (61-66). Changes in n-6 PUFAs and increases in AA production can contribute to platelet hyper-reactivity and aggregation by providing increased substrate for the production of TXA2 (61,67-69). Such changes may result in a state of dynamic vasoconstriction and exacerbate the development of heart failure (61,69-73). Risk factors associated with changes in PUFA metabolism that increase AA production and activation of platelets include obesity, diabetes and aging (61,71,72,74-82). Roman R J provides a thorough review of the emerging body of evidence for role of the cytochrome p450 monooxygenase pathway for AA metabolites in the form of epoxyeicosatrienoic acids (EETs), dihydroxyeicosatetraenoic acids (Di-HETEs) and hydroxyeicosatetraenoic acids (HETEs) and their control of cardiovascular function (83).

Progress is being made on understanding the relationships between the elevation of production of metabolites along the cytochrome P-450 monooxygenase pathway and the development of hypertension (83). Takase B et al found that abnormalities of AA metabolism accompany, and may play a role in the pathogenesis of acute myocardial infarction (84). Developing treatments for cardiovascular disease are focused on blocking the AA metabolite pathways or using them for drug delivery. The Nanoveson™ therapy approach to AA metabolite pathways for the treatment of cardiovascular disease is to sequester and remove AA and its precursor LA, thereby significantly reducing the levels of AA available for metabolism and cascade, and by restoring AA homeostasis.

Atherosclerotic Cardiovascular Disease (ASCVD) is a major killer and likely the most costly disease facing the world. Waddington et al observed that multiple AA metabolites were detected in all atherosclerotic plaques (106). Cai and Harrison identified AA pathway enzymes as reactive oxygen species (ROS) in vascular cells and as a source of endothelial dysfunction (107). Elinder et al summarized the powerful evidence of the direct links between AA metabolism and ASCVD in observing AA as a precursor to potent inflammatory mediators and platelet-activating eicosanoids can initiate, sustain, and potentiate inflammatory reactions during all stages of atherosclerosis development by attracting and activating immune-competent cells (108,109-118).

AA and Inflammation/Pain

The relationship between AA metabolism and its cyclooxygenase and lipoxygenase metabolite byproducts in inflammation and pain has been a focus of extensive medical research and pharmaceutical product development for years, and will therefore not be extensively reviewed here. AA and its metabolites (eicosanoids) are powerful mediators that organisms used to induce and suppress inflammation as part of an innate response to disturbances (85). Bogatcheva et al review the understanding of these responses relating to all three AA metabolic pathways; but focus on the all important inflammatory role of endothelial cells that form a semi-permeable barrier between the interior space of blood vessels and the underlying tissues; endothelium controls the processes of vascular tone, homeostasis, adhesion of platelets and leukocytes to the vascular wall (85). Research available on AA and its role in inflammation and pain is extensive in the literature.

AA and Gastrointestinal Diseases

The literature is replete with research concerning and highlighting the relationship between AA and gastrointestinal diseases. AA cascade eicosanoids are known to play a major role in gastrointestinal physiology and pathophysiology (121). There is a suggested relationship between the AA cascade into eicosanoids and inflammation in most gastrointestinal diseases including; Crohn's disease, gastritis, heartburn and ulcerative colitis. By reducing AA and restoring AA homeostasis, Nanoveson™ is a potential treatment option for such gastrointestinal diseases.

AA and Allergy and Asthma

The literature is also extensive regarding research reviewing and addressing the relationship between allergies and asthma and the AA cascade along the 5-Lipoxygenase pathway and leukotrienes activity. Paul O'Byrne, MD, noted that leukotrienes are derived from the 5-lipoxygenase pathway of AA metabolism, and increased production of leukotrienes has been demonstrated in patients who have asthma (122). The research of Jay Grossman, MD in are article in CHEST considering the relationship between allergies and asthma observed that the focus of study has shifted to the role of the AA metabolic pathway and other inflammatory mediators in the pathophysiology and treatment of upper and lower airway disease (123). Calabrese et al found that eosinophils retrieved from inflamed airways of asthmatics have a larger AA content than their blood counterpart and that the high levels of AA in these cells is primarily due to a remodeling of endogenous arachidonate pools with the accumulatin of this fatty acid in a TAG-associated pool (124). Black and Sharpe considered changes in the diet that have increased the intake of the AA precursor linoleic acid and observed that this may explain the increase in the prevalence of asthma, eczema and allergic rhinitis due to an increase in the synthesis of prostaglandin E2, which in turn can promote the formation of immunoglobulin E (125).

AA in Bile

Research has indicated that low rates of biliary phosphatidylcholine (PC) production is biased against release of bile PC rich in AA in bile acid-depleted rats (14). At high rates of PC production demand, PC production is not biased but more closely matches the composition of PCs in the liver (14). One possibility is that this AA selectivity is due to the fact that at low rates of biliary PC demand there is a higher relative proportion of PC re-circulated in the bile pool, which had its AA cleaved from the n-2 position by PPLA2 on prior passes through the intestines. New PC added to the bile pool during high demand for bile lecithin will more closely reflect the FA makeup of PC in the liver and PC remodeled from TAG stores. Nanoveson™ therapy research will need to monitor for potential bile acid depletion and its impact on AA content of bile PC. It may be that AA content of PC in SAMMVs will provide a marker and diagnostic tool for bile acid depletion requiring intervention with bile acid supplementation.

Zhou and Nilsson observed that bile PC tends to have a higher composition of AA than liver and plasma PC, and observed that AA makes up 6-8% of the fatty acids in PC in human bile (19). Research has indicated that it is expected that 70% to 80% of bile PC is sn-1 palmitoyl (palmitic) sn-2 oleoyl (oleic) (18:1) or linoleoyl (linoleic) (18:2). The third most abundant PC is sn-1 palmitoyl sn-2 arachidonyl (arachidonic) (20:4) AA (26). LA is the precursor to the formation of AA, therefore removal of LA is expected to reduce the body's ability to produce excess amounts of AA, and to assist in reducing the pool of available free AA.

Werner A, et al reported that human bile PL provide up to 1.7 grams of AA to the intestine per day (45,46); and that an average Western adult diet supplies 1.8 grams of AA daily (45,47), and noted that biliary PL secretion in the intestine provides a significant portion of enteral AA. This observation should be compared to Zhou and Nilsson observing that in the Australian diet the average intake of dietary AA is 130 mg/day in males and 96 mg/day in females (19); the difference is substantial. Zhou and Nilsson, observing the Australian diet, noted the secretion of 5-10 g of bile PC per 24 hours supplies about 150-350 mg of AA to the gut endogenously (19); also significantly less than reported by Werner for Western adults. If accurate, the western diet contains greater than ten times the AA; and the average Westerner generates more than 10 times the AA endogenously from the release of AA into bile. There is also an unknown amount of AA entering the gut lumen when mucosal cells are sloughed off during normal cell turnover (19).

AA Metabolites in Bile

It is also expected that bile includes a significant amount of AA metabolites in addition to the AA and linoleic precursor fatty acids in bile phospholipids and removed in the SAMMVs. Relationships with labs that can detect the level of AA metabolites in SAMMVs and in the AQ excreted with the SAMMVs are anticipated. Wang and Ballatori concluded that the AA metabolites from leukotriene metabolism in the form of LTD4 and LTE4 were the predominant leukotreine metabolites in human bile (59). The degree to which the cyclooxygenase and monooxygenase system metabolites are released in bile, has not been discovered in the literature. The cytochrome P450 monooxygenase system is involved in the production of bile salts in the liver (49) and potentially large amounts AA metabolites in the form of CYP450 will be included in SAMMVs and removed by Nanoveson™ therapy.

Huber et al observed that LTC4 and LTD4 catabolism into LTE4 might take place not only in blood circulation, but also in bile canaliculi (102). The amount of AA that has been metabolized and released in the form of AA metabolites, such as LTE4, during Nanoveson™ therapy in SAMMVs and AQ has yet to be determined. It is expected that relevant amounts of LTE4 are present both in SAMMVs and in AQ produced by Nanoveson™ therapy. LTE4 may play an important role along with the phospholipids in the formation of SAMMVs. Additional research will confirm or reject such a role.

Perhaps more important than the amount of LTE4 or CYP450 removed in SAMMVs, is that improving or restoring optimal enterohepatic circulation will allow for the ongoing release of AA metabolites in bile, not just during Nanoveson™ therapy. The amounts of AA metabolites and therefore AA released by improved ongoing enterohepatic circulation with Nanoveson™ therapy are expected to increase substantially, thus restoring overall body AA homeostasis.

Optimizing Bile Pool Enterohepatic Circulation

The focus of the present application has been on the amounts of liver TAG converted to PL and removed and the amount of AA and its precursors removed from the liver by Nanoveson™ therapy. Excess liver TAG and/or the AA cascade are drivers of the major diseases reviewed and many others not considered here. However, it is important to note that the amounts of these compounds removed by an individual Nanoveson™ treatment in SAMMVs and AQ are expected to be dwarfed by their ongoing metabolism removal from the effects of improved bile flow and enterohepatic circulation. Researchers have noted that recovery from TAG accumulation is accompanied by increased PL synthesis, remobilization of liver PL, and increased turnover of plasma phospholipids (120). Removing excess TAG from the liver with Nanoveson™ therapy is therefore expected to improve enterohepatic circulation and lipid synthesis.

Even minor improvement of enterohepatic circulation of the bile pool is expected to increase the removal of AA, AA substrates, improve phospholipid synthesis from liver TAG, and decrease fatty liver. Enterohepatic circulation may improve temporarily after Nanoveson™ therapy and then decline, requiring an additional treatment. After multiple Nanoveson™ treatments, permanent improvement is expected to be realized. When enterohepatic circulation of the bile pool is increased, the positive benefits from ongoing AA release and homeostasis are expected to be substantially greater than that achieved by a single Nanoveson™ treatment.

The key to expected long-term effectiveness of Nanoveson™ therapy to address disease is its improving and/or optimizing the enterohepatic circulation of the bile pool. It is hypothesized that in most liver diseases, the enterohepatic circulation of the bile pool is compromised in some manner. Some level of biliary stasis is likely present. It is possible that even a minor degree of biliary sludge or fatty liver can impact enterohepatic circulation and compromise liver function and AA homeostasis. In some cases, it may prove to be the affects of age and the accumulation in the biliary tract of minimal amounts of cellular debris and minimal liver TAG that has compromised bile pool circulation. It is anticipated that Nanoveson™ therapy will be established as the method for improving enterohepatic circulation and even restoring optimal enterohepatic circulation.

The Nanoveson™ therapy method of action hypothesis proposes that even mild forms of stasis or fatty liver can potentially compromise optimal biliary and plasma turnover of AA. In such cases, homeostasis of AA is disturbed and the deleterious effects of the AA cascade are set in motion in the form of AA driven inflammatory diseases such as cardiovascular disease, cancer and arthritis. The TAG and AA removal during Nanoveson™ therapy, which could be overestimated in the research presented in this application will be far less than amounts removed on an ongoing basis by improved enterohepatic circulation. Optimal enterohepatic circulation is expected to return the body to a state of AA homeostasis. Improvements in AA homeostasis should be indicated by changes in AA balances as indicated in fatty acid ratios in blood plasma panels that will be included in the clinical trial process.

EXAMPLES

Laboratory Results

In light of the fact that the active ingredients in Nanoveson™ therapy have a long history of safety and their sale is not restricted, since they are not new molecular compounds, Nanoveson™, LLC took the liberty to collect limited samples for analysis. It should be stressed that results discussed here are highly preliminary. The low number of samples "two" is emphasized. Nanoveson™, LLC engaged a major university laboratory, with comprehensive experience in testing phospholipids present in fecal matter, to conduct testing on SAMMV samples produced by Nanoveson™ therapy. The limited lipid testing done thus far confirms the primary and important aspects of Nanoveson™ therapy hypothesis.

The following is a summary of the methods utilized for extraction and quantification of phospholipids and fatty acid fractions from SAMMV samples by the lab. The SAMMV samples were homogenized in 0.9% NaCl in water; one volume of sample (by weight), to 9 volumes of saline (by volume). Polytron and sonicate were used to homogenize thoroughly, then 2 grams of the homogenate were extracted in the standard Folch extraction procedure, which is 2 grams (or ml) of sample, 3 ml of methanol, and 6 ml of chloroform.

Centrifuge was applied at 2500 rpm for 10 minutes, and the bottom layer was removed, which contained the lipid. An additional 6 ml of chloroform was added to the sample; vortex, centrifuge and remove (and pool with previous) bottom layer and dried under Nitrogen to remove the solvent, and the remaining material was then resuspended in a solvent mixture and injected HPLC.

Total phospholipids, phosphatidylcholine and lysophosphatidylcholine in SAMMVs were determined by HPLC-ELSD. The total fat was resuspended in choloroform/methanol/acetone/hexane (2.0/3.0/0.5/0.5, by volume) and filtered through a 4-mm Millex-FH filter (with hydrophobic PTFE membrane, 0.5-um pore size; Nihon Millipore Ltd., Yonezawa, Japan) to remove potential interfering substances that might decrease the sensitivity of the detector. Separation of lipids was achieved using HPLC (Waters 2690; Alliance, Milford, Mass. USA) equipped with an autosampler, a column heater and a normal phase column (YMC-Pack Diol 120 NP, 24 cm×4.6 mm inner diameter, 5-um particle size and 12-nm pore size; Kyoto, Japan) with a flow rate of 2 ml/min using a quaternary solvent system consisting of hexane/petroleum ether (97:3 by volume), methanol/triethylamine/acetic acid (765:15:13 by volume), acetone/triethylamine/acetic acid (765:15:13 by volume) and isopropanol/acetic acid (800:40 by volume).

The autosampler chamber and the column heater were kept at 18 and 35 degrees C., respectively. Lipid classes were detected and quantified using an evaporative light-scattering detector (model 2000; Alltech, Mandel Scientific, Guelph, Ontario, Canada) with a nitrogen flow rate of 1.8 mil/min and drift tube temperature at 60 degrees C. Analyses were conducted in the linear range of the detector with calibration curves constructed using authentic standards for each lipid class. Total phospholipid was calculated as the sum of the individual phospholipids. Total phosphorus in the SAMMV lipid extract was also quantified using the colorimetric method of the lab, with monobasic potassium phosphate as the standard.

Gas chromatography was used to analyze and determine the fatty acid fractions of PC, PI, TAG collected from the HPLC. The HPLC eluent was split, with 10% going to detector and 90% going to the fraction collector. Each fraction is collected and the solvent dried under Nitrogen gas. Fatty acids were derivatize using a mixture of boron trifluoride in methanol (Sigma) and heat at 100 C for 30 minutes to convert all fatty acids to fatty acid methyl esters, cool, add water then extract the FAME with hexane.

Samples were dried with Nitrogen to remove the hexane and concentrate the FAME, then re-suspended in a small amount of hexane. The FAME were then injected into the gas chromatographs (Agilent 6850) using an HP-88 column, 30 meter×0.25 mm inner diameter×0.20 micron film thickness and detected with a flame ionization detector. The oven of the GC was temperature programmed to separate the FAME and retention times of pure commercially available standards used as comparison to identify the sample FAME. Quantitation is performed by calculating the peak area of each individual fatty acid methyl ester (done automatically by the GC Chemstation software) and then calculating the % (by weight) of each fatty acid in the sample.

Limited preliminary lab testing indicates Nanoveson™ therapy releases clinically significant amounts of liver stores of TAG remodeled into phospholipids in the bile. These phospholipids, in the form of aggregated micelles and vesicles, are being sequestered and excreted from the body in the form of SAMMVs and AQ. Preliminary results indicate that when the levels of phospholipids are reduced by multiple Nanoveson™ treatments, the amount of phospholipids produced during Nanoveson™ therapy is <the CMC and/or MPB. Note that these assumptions are subject to error.

Based on Nanoveson™ therapy utilized to generated samples, the dietary lipids consumed in the 10 PM solution contained no phospholipids. It is possible that fractional amounts of phospholipids sloughed off the walls of the intestines, but such amounts would be minimal if at all. Limited laboratory results thus far provide preliminary evidence that the Nanoveson™ therapy hypothesis is accurate. Nanoveson™ therapy appears to remove clinically significant amounts of liver TAG converted to PL, and as a byproduct, significant amounts of AA are removed from the body.

Example

Sample #1

This sample of SAMMVs weighed 6.78 grams, and represented only a portion of the SAMMVs produced by Nanoveson™ therapy. This SAMMV sample was expected to be between a Type I and Type II Sample. The lipids discovered in this sample included FFA, TAG, and PLs. Of particular interest is the fact that this sample includes TAG, suggesting that the level of phospholipids was >CMC; thus providing for the production of micelles that reached the micellar phase boundary and produced vesicles that incorporated TAG (8 mg per gram of sample), with micelles and vesicles aggregated into the SAMMVs. This patient had participated in a number of therapies, and if the hypothesis is accurate, would be expected to have minimal amounts of TAG stores in the liver. The phospholipids (PL) identified in the sample include phosphatidylcholine (PC), sphyngomyelin (SPH), and lysophsophatidylcholine (LPC) and made up 0.8% of the total weight of the sample. The individual fatty acids in the PC included 6.5% AA by weight percent; within the percentage expected to be found in PC in bile. This sample also contained 14.9% LA (precursor to M) by weight percent.

Example

Sample #2

This sample of SAMMVs weighed 2.6 grams, and represented almost half of the SAMMVs produced by Nanoveson™ therapy. This SAMMV sample is expected to be a Type II Sample as described above. The lipids discovered in this sample included FFA, and PLs. Of particular interest was the fact that there was virtually no TAG (less than 1 mg per gram of sample). This is less than one percent of the lipids and one one-thousandth of the total sample, identified in this sample. It is a bit early to come to this conclusion, but it suggest that the level of phospholipids was <CMC or at least lower then Sample #1; preventing or reducing the production of micelles and vesicles for aggregation into SAMMVs in the intestines and absorption of TAG; thus suggesting the SAMMVs are composed of biliary micelles and vesicles of phospholipids and bile salts in the form of inspissated bile and bile plugs from the biliary tract and potassium carboxylate micelles, and the FFA that bound to the SAMMVs in the intestines. The higher the PL content, the more likely they are more biliary than intestinal in origin. The phospholipids (PL) identified in Sample #2 included phosphatidylcholine (PC), sphyngomyelin, lysophsophatidylcholine (LPC) and phosphatidylinositol (PI) and made up 1.8% of the total weight of the sample. The individual fatty acids attached to the PC included 9.3% AA by weight percent; above the 6-8% percentage of AA expected to be found in PC in bile based on research in the literature. This sample also contained PC with 7.2% LA (precursor to M) by weight percent. Other factors may explain the lack of TAG in Sample #2 relative to Sample #1; such as differences in gastric lipase or other digestive lipase activity; i.e., gastric lipase may have been more thorough. However, it is clear that the PC in the sample was biliary in origin due to the AA content.

How TAG binds to SAMMVs, theoretically through its incorporation in vesicles, is not fully understood. It is expected to be due to the surface charge binding properties of the vesicles and the fact that pH in the AQ is expected to be below the bile salt CMpH, thus encouraging aggregation of the vesicles. It is also possible that the TAG in Sample #1 is coming from some source other than vesicles, but this research has not discovered another explanation to date. Type I SAMMVs as depicted on the SAMMV Type Chart may have significantly higher amounts of TAG in them than Sample #1 above. Such samples will be documented during clinical trials.

PC is the most abundant phospholipid in bile and in the samples. Both samples also included the phospholipids SPH, LPC, and PI. Of these, only PI was analyzed for AA content and was 1.5% AA in both samples. When Nanoveson™ research is expanded, if the SPH is found to have significant amounts of AA, it will increase the amounts of AA that can be removed by Nanoveson™ therapy. The LPC and the PI were less than one-tenth of one percent of the total samples.

Example

Samples #3 and #4

Additional samples were also analyzed to confirm intestinal vs. biliary formation of the SAMMVs. Sample #3 consisted of ~7.5 grams of SAMMVs that were relatively large dense SAMMVs with individual SAMMVs of 0.5 cm to 1.5 cm diameter sizes. Sample #4 represented the ~1 gram core of a large ~1.5 cm SAMMV from Sample #3 SAMMVs. Laboratory analysis revealed that the 18:3n3 fatty acids in the 10 PM solution were present in equal quantities in both Sample#3 and Sample#4, representing exactly 11.1 percent of the total free fatty acids in each sample. It should be noted that FFA represented ~22.5% of both samples. It should noted that if the Sample#4 core was formed in the liver or biliary tract it would be expected to have no FFA and virtually no 18:3n3 fatty acids that were in the 10 PM solution. Very small amounts of 18:3n3 FFA from PL broken down by lipase would be possible. The large amount of 18:3n3 and consistency in the #4 core with #3 indicate intestinal formation through micelle and vesicle fusion and aggregation. It should also be noted that these samples exhibited fusogenic and aggregation activity, even after PL was broken down with such breakdown expected to be due to exposure to lipase products from higher temperature, suggesting the presence of AA metabolites and their anticipated fusogenic properties (139).

As already noted, Ahmed A et al. (169) (American Family Physician, 2000; 61:1673-80, 1687-8) observed that gallstones in the gallbladder are up to 90 percent cholesterol stones (more than 50 percent cholesterol) or mixed (20 to 50 percent cholesterol). The remaining 10 percent are pigmented stones, which have less than 20 percent cholesterol. The examples/samples of SAMMVs presented above were only ~1% cholesterol, including cholesterol esters and free cholesterol; suggesting SAMMVs are not gallstones, but the product of lipid polymorphism and nanobiotechnology fusion and aggregation.

Sample #1 and #2 were not acidified prior to laboratory analysis in order to extract the fatty acids from the potassium carboxylate soaps and/or other soaps in SAMMVs, as discussed earlier. Samples #3 and #4 were approximately 4 percent soaps by HPLC. The samples are primarily expected to be digestion products in the form of monoglyceride, diglyceride, free fatty acids, glycerol and other digestive products. Nanoveson™ research is primarily focusing on the phospholipid and other membrane content of SAMMVs. Future research will evaluate this additional content and seek to quantify, document and provide details on all SAMMV content.

The primary focus of the present application are the membranes of the vesicles that make up a small percentage of the total SAMMVs. SAMMV cores are expected to largely contain AQ in the form of 10 PM solution digestive products of hydrolysis such as diglycerides/diacylglycerol (DAG) and monoglycerides/monoacylglycerols, in addition to the free fatty acids and potassium carboxylates. The intent of these examples/samples was not to provide full analysis of SAMMV products of digestion, but to confirm the Nanoveson™ therapy hypothesis of monolayer and bilayer vesicle membrane fusion and aggregation to form SAMMVs. A full consideration and quantification of all digestion products in SAMMVs is required.

These examples/samples provide evidence in support of Nanoveson™ therapy hypothesis. They are admittedly limited in terms of delivering statistical validity, but that was not the intent of the laboratory analysis. The purpose was to provide useful evidence for the basic premise of the Nanoveson™ therapy method of action hypothesis with actual SAMMV samples, and serve to assist in strategy and planning for more encompassing research and clinical trials; and to demonstrate some of the methodology to be utilized in Nanoveson™ research. Note that minimal samples provide a great deal of room for error and misinterpretation. There could be other reasons for the results observed, but the evidence that supports the explanation provided by the invention is promising for the advent of applied lipid polymorphism and nanobiotechnology with nanoscale micelle and vesicle aggregation for treating NAFLD, comorbid diseases, other liver diseases, and AA driven diseases.

These samples also indicate the diagnostic potential of Nanoveson™ therapy. By providing standardized active Nanoveson™ treatment ingredients and doses to patients, and creating standard biomarker lipid panels, it is anticipated that diagnostic tests for liver disease and other lipid related diseases will be forthcoming.

Biomarkers and Diagnostic Tests

There is a significant and growing need for non-invasive and cost effective biomarkers and diagnostic tests for liver diseases and other diseases. SAMMV formation occurs due to the biochemistry produced by the interaction of compounds in the intestines from a clinically significant amount of rapid liver lipid polymorphism and bile release during Nanoveson™ therapy. SAMMVs sequester metabolic compounds released by the liver during therapy and therefore provide a rich source of biomarkers and important clinical data related to the patient's liver condition and liver related disease states. The biomarkers sequestered in SAMMVs and in AQ can be used to design diagnostic tests. Nanoveson™ therapy in conjunction with existing diagnostic tools and biomarkers, such as lipid panels, blood panels for lipids and fatty acids, ultrasounds and other diagnostic tools will serve to develop and establish disease treatment protocols.

The amount of the following content and their ratios to other content found in SAMMVs and AQ produced by Nanoveson™ therapy will provide biomarkers for diagnostic tests; phospholipids, specific phospholipid bound fatty acids, fatty acids, AA, AA metabolites, catecholamines, annexins, choline, DNA, bacteria, cholesterol, bile salts, TAG, yeast, fungi, viruses, parasites, pancreatic enzymes, other enzymes, and any additionally discovered SAMMV biomolecule or other content. Biomarkers and diagnostic tests for fatty liver, NAFLD, NASH, ALD, fibrosis, cirrhosis, cholestatic liver diseases, other liver diseases, lipid disorders, insulin resistance, metabolism disorders, AA driven inflammatory disorders and diseases, cystic fibrosis, ASCVD, drug metabolism, and various other diseases and disorders are anticipated to be established. The total amount of and ratio of potassium carboxylates and other digestive compounds in SAMMVs produced from partial digestion of therapy dietary lipids and as compared to biliary released compounds will also provide for biomarkers and relevant clinical data on the patient's digestive health.

Liver disease poses particularly daunting hurdles for biomarkers and diagnostic testing, as liver biopsies can be dangerous and prohibitively expensive and are currently the primary means of testing for serious liver diseases. An example of the diagnostic potential is in the samples presented in this research, the amount of AA in Sample #2 over the anticipated normal range of 6 to 8 percent at 9.3 percent in human bile may well indicate some level of NAFLD, NASH, fibrosis, cirrhosis or other disease state. The amount and type of AA metabolites in SAMMVs, be they LTD4, LTE4, CYP450 or others, offer potential to determine the state of various AA driven diseases. Catecholamines and annexins may prove to be biomarkers for NAFLD, NASH, ALD, fibrosis, cirrhosis, etc. Cholesterol amounts in SAMMVs may correlate with various cardiovascular diseases or other diseases. The ratio of phospholipids to the total weight of SAMMV will determine the degree of intestinal or biliary formation of the SAMMVs and potentially determine the amount of fatty liver, fibrosis and cirrhosis.

Clinical trials will include phospholipid, TAG, fatty acid, AA, AAM, CAT, AX and other biomolecule panels provided by SAMMVs and possibly the AQ excreted with them, as well as blood plasma lipid panels. These panels offer the opportunity to establish normal ranges and biomarkers for Nanoveson™ therapy and SAMMVs. Such panels may allow determination of the disease state and/or cause of inspissated bile and bile plugs, i.e., biliary SAMMVs, which help to form intestinal SAMMVs. The potential exist to establish non-invasive diagnostic tests and biomarkers with such lipid panels. Lipid panels that include fatty acid makeup of PL, AA metabolites, and other SAMMV content will provide a rich source of data that will provide for the establishments of biomarker standards. Such panels and established standards may identify specific liver diseases or states of diseases, depending on the ratios of the particular phospholipids and their makeup of fatty acids, other lipids and AA metabolites. Partnerships with labs that can develop, standardize and commercialize such diagnostic tests and biomarkers are anticipated. The use of the Nanoveson™ therapy for diagnostic tests and biomarkers may require total fasting from all solid foods and lipids by the patient for a period of 24 or more hours before therapy.

There is also the opportunity to develop blood plasma panels that measure and establish anticipated or normal plasma lipid ratios for patients utilizing Nanoveson™ therapy. The intent is to couple such panels with liver enzyme and metabolic syndrome panels to measure patient status and expected progress from a series of Nanoveson™ treatments. Standards need to be established for non-evasive blood plasma lipid panel tests and processes in addition to various diagnostic tests and biomarkers based on Nanoveson™ therapy and the biochemistry of SAMMV formation.

Methods of Use for the Invention

The use and method of action of Nanoveson™ therapy to treat NAFLD and other liver disease related to liver TAG deposits have been reviewed in detail. It will therefore not be reviewed extensively here; simply refer to this paper in its entirety. However, to summarize, the Nanoveson™ therapy method of action in treating fatty liver diseases is to trigger the conversion of liver TAG to phospholipids in bile, sequester the phospholipids in SAMMVs and excrete them through the cathartic effect. The therapy can be used to increase the rate of enterohepatic circulation and the ongoing conversion of liver TAG to PL for bile, which facilitates improved ongoing lipid synthesis to treat and prevent fatty liver on an ongoing basis. This method of action will treat liver TAG deposits related to NAFLD, cirrhosis, PBC and other liver diseases.

AA Cascade Diseases Use and Method of Action

Summarizing the AA cascade disease related Nanoveson™ therapy method of action; research has established that enterohepatic circulation is the human body's mechanism for maintaining and regulating quantitative levels of AA. Compromised enterohepatic circulation due to biliary stasis is expected to be more prevalent in developed countries than presently understood. By removing TAG deposits in the liver, improving bile flow and restoring more optimal enterohepatic circulation, and thereby restoring the body's ability to remove AA and maintain AA homeostasis, Nanoveson™ therapy reduces the availability of AA for AA cascade driven diseases. Nanoveson™ therapy, by improving ongoing enterohepatic circulation, will reduce the amount of and AA and the ratio of AA relative to other fatty acids in tissue and blood plasma. Lowering the AA ratio to n-3 and other n-6 fatty acids will treat high AA ratio and AA cascade related diseases. Improving enterohepatic circulation with Nanoveson™ therapy and increasing the intake of n-3 fatty acids is expected to be more effective at lowering AA ratios and treating AA cascade driven diseases than increasing n-3 fatty acids alone. Through this AA homeostasis improvement method of action Nanoveson™ therapy will treat and have positive outcome on arthritis, cancer, gastrointestinal diseases and heart disease related to the AA cascade and the aberrant affects of excessive amounts of AA in the form of free AA and lipid bound AA.

Cardiovascular Use and Method of Action—TAG, LDL, HDL and AA

The method of action for Nanoveson™ therapy in treating elevated TAG, high LDL and low HDL is by removing stores of liver TAG, removing biliary obstruction and reducing biliary stasis; therefore improving and increasing the liver's ability to perform ongoing lipid metabolism and ongoing phospholipid synthesis. With a higher rate of enterohepatic circulation, the liver is able to take in larger amounts of TAG in HDL, convert it to phospholipids in bile, and use bile flow and enterohepatic circulation to remove and regulate the body's lipid and fatty acid balances; therefore, HDL synthesis increases as the liver is able to metabolize more inbound lipid products. With greater amounts of TAG being metabolized as phospholipids, less LDL synthesis is required to export TAG from the liver and the liver adjust the LDL balances and synthesis. By removing TAG deposits in the liver and by increasing and improving the rate of enterohepatic circulation and the viscosity of bile, the liver is better able to mange lipid balances and ASCVD related lipid levels are expected to improve, with expected improvement to cardiovascular disease outcomes. Improvement of enterohepatic circulation and phospholipid synthesis provides for quantitative regulation of whole body AA balances, thus reducing the body's AA stores for the AA cascade of eicosanoids that drive ASCVD inflammation. Reducing the ratio of AA fatty acid in tissue and blood plasma will treat the AA driven causes of ASCVD inflammation.

Diabetes—Insulin Resistance Use and Method of Action

Research has demonstrated that Fatty Liver is comorbid with insulin resistance. The connection is not completely understood, but is likely related to the compromised lipid synthesis of fatty liver, particularly phospholipid synthesis. More optimal phospholipid synthesis would be expected to maintain blood plasma phospholipid ratios, which are going to influence the phospholipid makeup and ratios in virtually all tissue and cell membranes. The phospholipid membranes of cells and their impact on the functioning of cell membranes play a critical role in the flow of nutrients and other substances into and out of the cell. It is suspected that less than ideal ratios and distributions of the fatty acids between n-3 and n-6 fatty acids in the phospholipids that make up cell membranes have an impact on cell insulin resistance and sensitivity. By improving lipid, particularly phospholipid synthesis, Nanoveson™ therapy is expected to create a more optimal ratio of fatty acids in phospholipid membranes of cells and improve cell insulin sensitivity found in diabetes; specifically by decreasing the amount of AA in phospholipids in cell membranes. Other aspects of fatty liver that make it comorbid with diabetes will also involve the method of action of Nanoveson™ therapy and have a positive impact on diabetes and the ability to treat diabetes.

Cholestatic and Obstructive Liver Diseases Use and Method of Action

Nanoveson™ therapy's method of action for treatment of cholestatic and obstructive liver diseases is by producing an increase in bile production and the rate of bile flow in conjunction with marginally increased biliary pressure. The therapy is able to force inspissated bile, inspissated bile plugs, biliary debris, biliary sludge, and biliary casts, out of the biliary tract and into the duodenum, thus assisting in restoring liver, biliary function and bile flow.

Weight Loss Use and Method of Action

By improving enterohepatic circulation and phospholipid synthesis, there is an anticipated positive impact by increasing metabolism and use of the body's stores of lipids. By speeding up metabolism Nanoveson™ therapy is able to have a positive outcome on weight loss objectives. Nanoveson™ therapy has potential as a co-therapy with other weight loss treatments in addition to dietary changes and exercise.

Drug Metabolism Testing

There is a significant and growing need for new and improved methods for drug metabolism testing and biomarkers. The liver is the primary organ for drug metabolism. Nanoveson™ therapy, by producing the fusion and aggregation of biomolecules into the micelle and vesicle membranes and cores aggregated in SAMMVs, including pharmaceutical compounds, is expected to provide a method for testing the metabolism of existing and prospective drug compounds.

Nanoveson™ as Co-Therapy

Nanoveson™ offers unique potential for use in conjunction with other therapies for particular diseases, such as cancer and chemotherapy treatment. Destroying cancer cells with chemotherapy while removing AA as a substrate required for cancer cell growth may be a winning combination. Treatment with statins in conjunction with Nanoveson™ therapy may increase cardiovascular benefits. In the case of cystic fibrosis, supplementing with lipids due to deficiency, while removing inspissated bile to improve enterohepatic circulation and phospholipid synthesis, may prove more effective than individual forms of therapy.

Nanoveson™ as Contraindication Option

Physicians are increasingly faced with established medication contraindication issues for patients facing major chronic diseases. This is often the case with ASCVD when the standard therapy is contraindicated for "liver problems" due to elevated liver enzymes and ultrasounds that suggest fatty liver. More often than not, physicians are likely taking what is perceived as the lesser of two evils, explaining the risk to patients, but prescribing the standard therapy. Patients desire an option, but there is no option. Nanoveson™ therapy has the potential to be "the" contraindication option for many major diseases. The potential size of this contraindication market alone is significant and growing.

Nanoveson™ as Primary Therapy

The fact that Nanoveson™ has significant potential as a co-therapy and as a contraindication option should not obscure the possibility that it may become the primary and preferred therapy by many physicians and patients for indicated diseases. As a treatment regimen, Nanoveson™ therapy appears somewhat simple, but as described in this paper, the biochemistry at work is a highly complex use of the principles of lipid polymorphism to treat disease.

Nanoveson™ therapy is truly a new and fascinating way to treat major deadly diseases that will likely change many aspects of medicine, as we now know it if its efficacy is confirmed. Many physicians and patients will not choose Nanoveson™ as a therapy option. However, many physicians and millions of patients will recognize the advantages of utilizing the principles of applied lipid polymorphism as a treatment option, due to effectiveness of the treatment and the minimal and short-term expected side effects, as compared to standard established therapy. In cases where Nanoveson™ therapy may prove to be the only approved therapy, it will be an easy choice.

CONCLUSION

The preliminary evidence indicates that the Nanoveson™ therapy invention produces TAG conversion to PL released as bile. The PL is sequestered in SAMMVs and exits the body in clinically significant quantities. By default, the removal of clinically significant amounts of AA from the liver is also taking place. In the same way bile acid sequestrates remove cholesterol, and the body then moves more cholesterol to the liver for removal, Nanoveson™ therapy causes additional AA to be moved to the liver from blood, tissue and organs for removal, thus reducing body stores of AA. It is hypothesized that enterohepatic circulation and phospholipid synthesis can be optimized and AA homeostasis can be established by repeated Nanoveson™ therapy.

The invention claimed is:

1. A method of treatment of fatty liver disease involving an excess of triglyceride stores in the liver and/or an imbalance of ratios of omega 6 to omega 3 fatty acids, consisting of administering to a human patient in need thereof an oral dose with an only active ingredient of about 100±30 grams of lipids in the form of dietary triglycerides in the liquid form of oil in an amount effective to trigger the release of cholecystokinin (CCK) into the duodenum thus triggering a demand for bile exceeding the amount of bile available in the bile pool of the gall bladder and biliary tract and therefore generating a release of bile phospholipids, including phosphatidylcholine, from remodeled stores of triglycerides in the liver of the patient, with the amount of triglyceride remodeled into phospholipid and the amount of phospholipid released sufficient to exceed the critical micelle concentration (CMC) and the micellar phase boundary (MPB) in the intestines in an amount effective to cause the formation of sequestered and aggregated mixed micelles and vesicles (SAMMVs) in the intestines of the patient which are then eliminated via the bowels of the patient, and optionally adding a therapy dose consisting of phospholipid (PL) and/or free fatty acids to the oral dose of lipids or as a separate dose to force the formation of SAMMVs when they otherwise do not form or do not form in sufficient quantities, due to insufficient liver triglyceride deposits available for conversion to PL or other causes for more effective therapy, biomarker or diagnostic purposes and optionally administering to said patient effective doses of choline to insure sufficient quantities of choline required for the remodeling of liver triglycerides into phospholipids during therapy and/or to prevent choline deficiency due to therapy, and optionally administering to said patient a cathartic.

2. The method of claim 1, wherein the lipids comprise fatty acids selected from the group consisting of monounsaturated fatty acids, n-3 polyunsaturated fatty acids, n-6 polyunsaturated fatty acids, n-9 monosaturated fatty acids, and mixtures of any of the foregoing, in the form of dietary triglyceride.

3. The method of claim 1, further comprising orally administering to said patient a cathartic in an amount effective to empty the intestines prior to the administration of said oral dose of lipids.

4. The method of claim 1, further comprising orally administering to said patient a dose of magnesium in an amount effective to perform a function selected from the group consisting of: a) acting as a cathartic to empty the intestines prior to the administration of said oral dose of lipids, b) contributing to vesicle membrane fusion and aggregation to form SAMMVs, and c) both a and b.

5. The method of claim 1, wherein the oral dose of lipids is selected from the group consisting of dietary triglyceride.

6. The method of claim 5, wherein the oral dose of lipids further comprises omega-3 fatty acids.

7. The method of claim 1, further comprising having the patient abstain from ingesting substantially any lipids for about 24 hours prior to administration of an effective dose of a cathartic.

8. The method of claim 1, further comprising repeating the treatment.

9. The method of claim 1, wherein the treatment is selected from the group consisting of, treatment of liver triglyceride deposits related to non-alcoholic fatty liver disease (NAFLD), treatment of NAFLD, treatment of non-alcoholic steatohepatitis (NASH), treatment to reduce the amount of arachidonic acid (AA) and the ratio of AA relative to other fatty acids in tissue and blood plasma, and treatment to lower the ratio of arachidonic acid (AA) to n-3 and other n-6 fatty acids.

10. A method of treatment of claim 1, comprising pretreatment of the patient by administering a first dose of a cathartic at about dinner time;

administering a second dose of a cathartic about 2 hours after said first dose;
and then about 2 hours after the second dose of cathartic administering an oral dose of lipids in an amount effective to trigger cholecystokinin (CCK) release in the duodenum to generate a major release of bile phospholipids from remodeled stores of triglycerides in the liver, thereby causing the formation of sequestered and aggregated mixed micelles and vesicles (SAMMVs) which are then eliminated via the bowels of the patient,
wherein the patient begins the day treatment begins by abstaining from ingesting any lipids.

11. The method of claim 1 wherein the treatment has actions selected from the group consisting of:
remodeling of the liver of stores of triglycerides and phosphatidic acid to produce phospholipids (lecithin) for bile due to excessively high demand for bile; wherein remodeling occurs when liver stores of triglyceride consisting of three fatty acids attached to a glycerol molecule backbone undergo transformation into new molecular structures in the form of a phospholipid consisting of two fatty acids attached to a glycerol backbone (a diglyceride), attached to phosphate and choline, and when liver stores of phosphatidic acid, a small phospholipid, is transformed into phospholipids required for bile with the incorporation of choline,
excretion of the bile phospholipids into the biliary canaliculus to form bile, and into the duodenum to mix with oral dose of lipids,
rapid formation of mixed micelles and vesicles containing medium and long-chain fatty acids in the phospholipids,
release of bile and release of an amount of bile phospholipids from the liver that is substantially above the normal amount of phospholipids in the circulating bile pool,
conversion of clinically significant amounts of stored liver triglyceride (fatty liver) is converted into phospholipids for release through the hepatocyte membrane and into vesicles and micelles for aggregation and elimination in the SAMMVs and aqueous solution (AQ),
release of increased phospholipids (PL) on an ongoing basis with improved enterohepatic circulation,
release of a large amount of phospholipids in the bile which pushes the concentration of phospholipids in the small intestines beyond the critical micelle concentration (CMC), which creates an environment where lipid micelles can form rapidly,
increase in the rate of enterohepatic circulation,
ongoing conversion of liver triglyceride to phospholipids for bile, which facilitates improved ongoing lipid synthesis to treat and prevent fatty liver on an ongoing basis,
formation of lipid micelles caused by the amount of phospholipids released in the bile, after the concentration of phospholipids in the intestines is pushed beyond the CMC, which then pushes the concentration of micelles in the intestines beyond the micellar phase boundary (MPB); with the MPB being the level of concentration of a compound at which the CMC has been exceeded to a degree that micelles have formed and have reached a degree of concentration at which they can transform into vesicles, which creates an environment where vesicles can form and aggregate rapidly,
reduction of the pH in the small and/or large intestines to a point where pancreatic phospholipase A2 is suspended, or substantially decreased, such that the pH is below about 5.8, and the AA in the sn-2 postion is therefore not cleaved but remains bound to the phospholipid in the SAMMV or in AQ and is excreted, reduction of the pH in the small and/or large intestines to a level below about the bile salt critical micelle pH (CMpH) of 6.0 causing the bile acids to precipitate out of phospholipid bilayers, micelles, vesicles and SAMMVs to increase the rate of aggregation and excretion of SAMMVs and phospholipids, improvement in the lymphatic system circulation and drainage due to improved peristalsis as a result of changes in the fatty acid ratios in lymph and lymphoid organs, and a reduction of (AA) ratios in lymphoid organs, removal of amounts of cholesterol in the SAMMVs and AQ, and from improved ongoing enterohepatic circulation that will be clinically significant enough to provide a clinically significant effect in cholesterol related diseases, release of AA metabolites, catecholamines and annexins from hepatic cells into bile, thereby promoting fusion and aggregation of micelles and vesicles and thus facilitating formation of from about 1 to about 200 or more grams of SAMMVs in the intestines of the patient, which are then eliminated via the bowels of the patient within 24 hours.

12. The method of claim 1, wherein the oral dose of lipids or a separate therapy dose comprises the addition of phospholipid (PL) and/or free fatty acids to force the formation of SAMMVs when they otherwise do not form or do not form in sufficient quantities, due to insufficient liver triglyceride deposits available for conversion to PL or other causes, for more effective therapy.

13. The method of claim 1, further comprising administering to said patient effective doses of choline to insure sufficient quantities of choline required for the remodeling of liver triglycerides into phospholipids during therapy, and/or to prevent choline deficiency due to therapy.

14. The method of claim 1, where the fusion and aggregation of pharmaceutical and drug compounds and other biomolecules into micelle and vesicle membranes and cores in SAMMVs provide the creation of biomarkers and therefore a method for testing drug metabolism, safety and efficacy.

15. The method of claim 1, further comprising repeating the treatment every two weeks or as established by clinical trials until no SAMMVs form with the treatment, with the implication that triglyceride stores and other fusogenic compounds in the liver have been reduced and ongoing enterohepatic circulation has been optimized to improve ongoing lipid synthesis in the liver.

16. The method of claim 9, wherein the treatment is treatment of NAFLD.

17. The method of claim 9, wherein the treatment is treatment of liver triglyceride deposits related to non-alcoholic fatty liver disease (NAFLD).

18. The method of claim 9, wherein the treatment is treatment to reduce the amount of arachidonic acid (AA) and the ratio of AA relative to other fatty acids in tissue and blood plasma.

19. The method of claim 9, wherein the treatment is treatment to lower the ratio of arachidonic acid (AA) to n-3 and other n-6 fatty acids.

* * * * *